US011001626B2

(12) United States Patent
Geng et al.

(10) Patent No.: US 11,001,626 B2
(45) Date of Patent: May 11, 2021

(54) METHODS, DEVICES, KITS AND COMPOSITIONS FOR DETECTING TAPEWORM

(71) Applicant: IDEXX Laboratories, Inc., Westbrook, ME (US)

(72) Inventors: Jinming Geng, Scarborough, ME (US); David Allen Elsemore, South Portland, ME (US)

(73) Assignee: Idexx Laboratories, Inc., Westbrook, ME (US)

(*) Notice: Subject to any disclaimer, the term of this patent is extended or adjusted under 35 U.S.C. 154(b) by 0 days.

(21) Appl. No.: 16/591,329

(22) Filed: Oct. 2, 2019

(65) Prior Publication Data
US 2020/0102378 A1    Apr. 2, 2020

Related U.S. Application Data

(60) Provisional application No. 62/746,805, filed on Oct. 17, 2018, provisional application No. 62/741,849, filed on Oct. 5, 2018, provisional application No. 62/740,100, filed on Oct. 2, 2018.

(51) Int. Cl.
*G01N 33/563* (2006.01)
*G01N 33/53* (2006.01)
*C07K 16/18* (2006.01)

(52) U.S. Cl.
CPC ......... *C07K 16/18* (2013.01); *G01N 33/5308* (2013.01); *G01N 33/563* (2013.01); *C07K 2317/33* (2013.01)

(58) Field of Classification Search
None
See application file for complete search history.

(56) References Cited

U.S. PATENT DOCUMENTS

| | | | |
|---|---|---|---|
| 2,797,182 | A | 6/1957 | Guthrie et al. |
| 5,726,010 | A | 3/1998 | Clark |
| 7,523,637 | B2 | 4/2009 | Roth et al. |
| 7,736,660 | B2 | 6/2010 | Elsemore et al. |
| 7,951,547 | B2 | 5/2011 | Elsemore et al. |
| 7,993,861 | B2 | 8/2011 | Elsemore et al. |
| 7,993,862 | B2 | 8/2011 | Elsemore et al. |
| 8,097,261 | B2 | 1/2012 | Elsemore et al. |
| 8,105,795 | B2 | 1/2012 | Elsemore et al. |
| 8,232,092 | B2 | 7/2012 | Ho et al. |
| 8,268,574 | B2 | 9/2012 | Elsemore et al. |
| 8,367,808 | B2 | 2/2013 | Elsemore et al. |
| 8,580,518 | B2 | 11/2013 | Elsemore et al. |
| 8,895,294 | B2 | 11/2014 | Elsemore et al. |
| 9,040,245 | B2 | 5/2015 | Elsemore et al. |
| 9,063,129 | B2 | 6/2015 | Elsemore et al. |
| 9,103,823 | B2 | 8/2015 | Elsemore et al. |
| 9,212,220 | B2 | 12/2015 | Elsemore et al. |
| 9,239,326 | B2 | 1/2016 | Geng et al. |
| 9,739,714 | B2 | 8/2017 | Moll et al. |
| 9,746,469 | B2 | 8/2017 | Elsemore et al. |
| 9,919,313 | B2 | 3/2018 | Lowe et al. |
| 10,429,388 | B2 | 10/2019 | Elsemore et al. |
| 2008/0311557 | A1 | 12/2008 | Elsemore et al. |
| 2014/0274778 | A1 | 9/2014 | Tsao et al. |
| 2016/0145327 | A1 | 5/2016 | Geng et al. |
| 2017/0343544 | A1 | 11/2017 | Elsemore et al. |

FOREIGN PATENT DOCUMENTS

| | | |
|---|---|---|
| WO | 2008/156648 A1 | 12/2008 |
| WO | 2008/156650 A2 | 12/2008 |
| WO | 2009/143067 A2 | 11/2009 |
| WO | 2009/143079 A2 | 11/2009 |
| WO | 2009/143080 A2 | 11/2009 |
| WO | 2009/143081 A2 | 11/2009 |
| WO | 2009/143083 A2 | 11/2009 |
| WO | 2010/068310 A1 | 6/2010 |

OTHER PUBLICATIONS

Allan, J.C., et al., "Immunodiagnostic Tools for Taeniasis", Acta Tropica, 2003, vol. 87, pp. 87-93, doi:10.1016/S0001-706X(03)00059-7.
Allan, J.C., et al., "Coproantigens in Taeniasis and Echinococcosis", Parasitology International, 2006, vol. 55, pp. S75-S80, doi:10.1016/j.parint.2005.11.010.
Beugnet, F., et al., "Occurrence of Dipylidium caninum in Fleas from Client-Owned Cats and Dogs in Europe Using a New PCR Detection Assay", Veterinary Parasitology, 2014, vol. 205, pp. 300-306, doi:10.1016/j.vetpar.2014.06.008.
Bohórquez, A., et al., "Differential Diagnosis of Equine Cestodosis Based on E/S and Somatic Anoplocephala Perfoliata and Anoplocephala Magna Antigens", Veterinary Parasitology, 2012, vol. 190, pp. 87-94, doi:10.1016/j.vetpar.2012.06.001.
Bohórquez, A., et al., "Coprologically Diagnosing Anoplocephala Perfoliata in the Presence of A. Magna", Veterinary Parasitology, 2014, pp. 1-21, doi:10.1016/j.vetpar.2014.04.023. (Manuscript).
Casaravilla, C., et al., "Production and Characterization of Monoclonal Antibodies Against Excretory/Secretory Products of Adult Echinococcus Granulosus, and their Application to Coproantigen Detection", Parasitology International, 2005, vol. 54, pp. 43-49, doi:10.1016/j.parint.2004.08.006.
Casaravilla, C., et al., "Characterization of Carbohydrates of Adult Echinococcus Granulosus by Lectin-Binding Analysis", The Journal of Parasitology, Feb. 2003, vol. 89(1), pp. 57-61.

(Continued)

*Primary Examiner* — Padmavathi Baskar
(74) *Attorney, Agent, or Firm* — McDonnell Boehnen Hulbert & Berghoff LLP

(57) ABSTRACT

Methods, devices, kits and compositions for detecting the presence or absence of one or more tapeworm coproantigens in a sample are disclosed herein. The methods, devices, kits and compositions of the present invention may be used to confirm the presence or absence of tapeworm in a fecal sample from a mammal and may also be able to distinguish between different tapeworm species and in the presence of one or more infections with helminths (such as roundworm, hookworm, whipworm and heartworm), *Giardia* and parvovirus. Confirmation of the presence or absence of tapeworm in the mammal may be made, for example, for the purpose of selecting an optimal course of treating the mammal and/or for the purpose of determining whether the mammal has been rid of the infection after treatment has been initiated.

41 Claims, 20 Drawing Sheets

(56) References Cited

OTHER PUBLICATIONS

Cui, S-J., et al., "Proteomic Characterization of Larval and Adult Developmental Stages in Echinococcus Granulosus Reveals Novel Insight into Host—Parasite Interactions", Journal of Proteomics, 2013, vol. 84, pp. 158-175, doi:10.1016/j.jprot.2013.04.013.

Deplazes, P., et al., "Detection of Taenia Hydatigena Copro-Antigens by ELISA in Dogs", Veterinary Parasitology, 1990, vol. 36, pp. 91-103.

Elayoubi, F.A., et al., "Partial Characterisation of Carbohydrate-Rich Echinococcus Granulosus Coproantigens", International Journal for Parasitology, 2003, vol. 33, pp. 1553-1559, doi:10.1016/S0020-7519(03)00198-X.

Ito, A., et al., "Culinary Delights and Travel? A Review of Zoonotic Cestodiases and Metacestodiases", Travel Medicine and Infectious Disease, 2014, pp. 1-10, doi:10.1016/j.tmaid.2014.06.009.

Kania, S.A., et al., "Anoplocephala Perfoliata Coproantigen Detection: A Preliminary Study", Veterinary Parasitology, 2005, vol. 127, pp. 115-119, doi:10.1016/j.vetpar.2004.10.003.

Kouguchi, H., et al., "Echinococcus Multilocularis: Two-Dimensional Western Blotting Method for the Identification and Expression Analysis of Immunogenic Proteins in Infected Dogs", Experimental Parasitology, 2010, vol. 124, pp. 238-243, doi:10.1016/j.exppara.2009.09.016.

Lahmar, S., et al., "Screening for Echinococcus Granulosus in Dogs: Comparison Between Arecoline Purgation, CoproELISA and CoproPCR with Necropsy in Pre-Patent Infections", Veterinary Parasitology, 2007, vol. 144, pp. 287-292, doi:10.1016/j.vetpar.2006.10.016.

Nakao, M., et al., "State-of-the-Art Echinococcus and Taenia: Phylogenetic Taxonomy of Human-Pathogenic Tapeworms and its Application to Molecular Diagnosis", Infection, Genetics and Evolution, 2010, vol. 10, pp. 444-452, doi:10.1016/j.meegid.2010.01.011.

Proudman, C.J., et al., "Use of Excretory/Secretory Antigens for the Serodiagnosis of Anoplocephala Perfoliata Cestodosis", Veterinary Parasitology, 1996, vol. 61, pp. 239-247.

Shin, J.W., et al., Humoral Immune Response to Dipylidium Caninum Infection of Stray Dogs in Taiwan, Veterinary Parasitology, 2002, vol. 104, pp. 351-356.

Soriano, S.V., et al., "First Study About the Development of Adult Echinococcus Canadensis G6 Genotype of Goat Origin in Experimentally Infected Dogs", Veterinary Parasitology, 2016, pp. 1-25, doi:10.1016/j.vetpar.2016.08.008.

Tighe, P.J., et al., "ELISA in the Multiplex Era: Potentials and Pitfalls", Prot. Clin. Appl., 2015, vol. 9, pp. 406-422, doi:10.1002/prca.201400130.

Traversa, D., et al., "A Comparison of Coprological, Serological and Molecular Methods for the Diagnosis of Horse Infection with Anoplocephala Perfoliata (Cestoda, Cyclophyllidea)", Veterinary Parasitology, 2008, vol. 152, pp. 271-277, doi:10.1016/j.vetpar.2007.12.032.

Virginio, V.,et al., "Excretory/Secretory Products from In Vitro-Cultured Echinococcus Granulosus Protoscoleces", Molecular and Biochemical Parasitology, 2012, pp. 1-8, doi:10.1016/j.molbiopara.2012.01.001.

Waterkeyn, J., et al., "Sequence Analysis of a Gene Family Encoding Taenia ovis Vaccine Antigens Expressed During Embryogenesis of Eggs", Molecular and Biochemical Parasitology, 1997, vol. 86, pp. 75-84.

Yang, D., et al., "Expression of the Tpanxb1 Gene from Taenia pisiformis and its Potential Diagnostic Value by Dot-ELISA", Journal of Parasitology, Apr. 2014, vol. 100(2), pp. 246-250, doi:10.1645/13-304.1 (Abstract only).

Zarlenga, D.S., et al., "A Taenia crassiceps cDNA Sequence Encoding a Putative Immunodiagnostic Antigen for Bovine Cysticercosis", Molecular and Biochemical Parasitology, 1994, vol. 67, pp. 215-223.

Barbecho, J.M., et al., "Comparative Performance of Reference Laboratory Tests and In-Clinic Tests for Giardia in Canine Feces", Parasites & Vectors, Aug. 1, 2018, vol. 11(1), pp. 444-447, doi:10.1186/s13071-018-2990-6.

Abd-Eldaim, et al., "Detection of Feline Panleukopenia Virus Using a Commercial ELISA for Canine Parvovirus", Vet Ther., 2009, vol. 10(4), pp. E1-E6 (Abstract only).

Bailey, "The Raising of a Polyclonal Antiserum to a Protein", Methods Mol. Biol., 1994, vol. 32, pp. 381-388.

Dean, "Preparation and Characterization of Monoclonal Antibodies to Proteins and Other Cellular Components", Methods Mol. Biol., 1994, vol. 32, pp. 361-379 (Abstract).

Dean, "Preparation and Testing of Monoclonal Antibodies to Recombinant Proteins", Methods Mol. Biol., 1998, vol. 80, pp. 23-37.

Drenckhahn, et al., "Production of Polyclonal Antibodies against Proteins and Peptides", Methods Cell Biol., 1993, vol. 37, pp. 7-56.

Fu, et al., "Comparison of Multiplex Immunoassay Platforms", Clin. Chem., Feb. 2010, vol. 56(2), pp. 314-318, doi:10.1373/clinchem.2009.135087.

Gullick, "Production of Antisera to Synthetic Peptides", Methods Mol. Biol., 1994, vol. 32, pp. 389-399.

Morrison, "In Vitro Antibodies: Strategies for Production and Application", Annu. Rev. Immunol., 1992, vol. 10, pp. 239-265.

Olson, et al., "Prevalence and Diagnosis of Giardia Infection in Dogs and Cats Using a Fecal Antigen Test and Fecal Smear", Can. Vet. J., Jun. 2010, vol. 51(6), pp. 640-642.

Wright, et al., "Genetically Engineered Antibodies: Progress and Prospects", Crit. Rev. Immunol., 1992, vol. 12(3-4), pp. 125-168.

U.S. Appl. No. 13/182,573, filed Jul. 14, 2011.

U.S. Appl. No. 13/289,459, filed Nov. 4, 2011.

PCT Invitation to Pay Additional Fees, from the International Searching Authority, for International Patent Application PCT/US2019/054317, dated Dec. 16, 2019, pp. 1-3.

Guezala, M-C., et al., "Development of a Species-Specific Coproantigen ELISA for Human Taenia Solium Taeniasis", Am. J. Trop. Med. Hyg., Sep. 2009, vol. 81(3), pp. 433-437.

Allan, et al., "Coproantigen Detection for Immunodiagnosis of Echinococcosis and Taeniasis in Dogs and Humans", Parasitology, Apr. 1992, vol. 104(2), pp. 347-356.

Lloyd, et al., "The Role of IgA Immunoglobulins in the Passive Transfer of Protection to Taenia Taeniaeformis in the Mouse", Immunology, May 1978, vol. 34(5), pp. 939-945.

International Search Report, from the International Searching Authority, for International Application No. PCT/US19/54317, dated Feb. 6, 2020, pp. 1-4.

Written Opinion, from the International Searching Authority, for International Application No. PCT/US19/54317, dated Feb. 6, 2020, pp. 1-13.

Adolph, C., et al., "Diagnostic Strategies to Reveal Covert Infections with Intestinal Helminths in Dogs", Veterinary 2017, vol. 247, pp. 108-112.

Boufana, B.S., et al., "Evaluation of Three PCR Assays for the Identification of the Sheep Strain (Genotype 1) of Echinococcus granulosus in Canid Feces and Parasite Tissues", Am. J. Trop. Med. Hyg., 2008, vol. 78(5), pp. 777-783.

Buishi, I., et al., "Canine Echinococcosis in Turkana (North-Western Kenya): A Coproantigen Survey in the Previous Hydatid-Control Area and an Analysis of Risk Factors", Annuals of Tropical Medicine & Parasitology, 2006, vol. 100 (7), pp. 601-610.

Craig, P.S., et al., "Prevention and Control of Cystic Echinococcosis", Lancet Infect. Dis., Jun. 2007, vol. 7, pp. 385-394.

Craig, P., et al., "Intestinal Cestodes", Curr. Opin. Infect. Dis., 2007, vol. 20, pp. 524-532.

Craig, P., et al., "Echinococcus Granulosus: Epidemiology and State-of-the-Art of Diagnostics in Animals", Veterinary Parasitology, 2015, vol. 213, pp. 132-148.

De, S., et al., "Detection of Canine Echinococcosis", Asian Pacific Journal of Tropical Medicine, 2010, pp. 519-522.

Drake, J., et al., "Innovative Multicenter Analyses of Tapeworm Prevalence in Western European Dogs", SEVC (Southern European Veterinary Conference), 2018, Madrid, Spain, [last accessed Oct. 1, 2018] (Abstract only).

(56) References Cited

OTHER PUBLICATIONS

Lahmar, S., et al., "Screening for Echinococcus granulosus in Dogs: Comparison Between Arecoline Purgation, coproELISA and coproPCR with Necropsy in Pre-Patent Infections", Veterinary Parasitology, 2007, vol. 144, pp. 287-292.
Li, T., et al., Taeniasis/Cysticercosis in a Tibetan Population in Sichuan Province, China, Acta Tropica, 2006, vol. 100, pp. 223-231.
Torgerson, P.R., et al., "Echinococcosis Diagnosis and Diagnostic Interpretation in Population Studies", Trends in Parasitology, 2009, vol. 25(4), pp. 164-170.
Cestode Diagnostics, University of Salford, pp. 1-2. [Last accessed Oct. 1, 2018, (www.star.salford.ac.uk/page/Cestode_Diagnostics)].

METHODS, DEVICES, KITS AND COMPOSITIONS FOR DETECTING TAPEWORM

CROSS-REFERENCE

This application claims the benefit of priority from U.S. Provisional Application Ser. No. 62/740,100, filed Oct. 2, 2018; 62/741,849, filed Oct. 5, 2018; and 62/746,805, filed Oct. 17, 2018, all which are incorporated by reference in their entirety.

BACKGROUND OF THE INVENTION

1. Field of the Invention

The present invention relates to compositions, devices, kits and methods for the detection of and distinguishing between tapeworm species in mammals. More particularly, the present invention relates to antibodies and antibody compositions, devices, kits, and methods for detecting the presence or absence of tapeworm species in a sample from a mammal and for distinguishing between tapeworm antigens.

2. Description of the Prior Art

Parasitic worm infections are common in animals and, if not diagnosed and treated, can cause serious disease or death. Current methods for diagnosis of parasitic worm infections primarily involve microscopic examination of fecal samples, either directly in fecal smears or following concentration of ova and parasites by flotation in density media or by sedimentation. Despite this procedure's high adoption, the method has significant shortcomings. These microscopic methods are time consuming and require specialized equipment. In addition, the accuracy of results of these methods is highly dependent upon the skill and expertise of the operator. For example, the presence of tapeworm is determined by looking for eggs or proglottids, but these are excreted intermittently and in small numbers. Not surprisingly, tapeworm infection is often not diagnosed on routine fecal examination.

Stool handling is disagreeable and hazardous. Sanitary and inoffensive procedures for processing stool are awkward and often complex. Such procedures may include weighing, centrifuging and storing, and are difficult except in a clinical laboratory equipped with a suitable apparatus, protective equipment, and a skilled technician. Therefore, any reduction in the number of steps required to perform a fecal test and any reduction in contact between test operator and the test material is desirable. Clinical laboratories have been using the immunoassay methods for the detection of various viruses, bacteria and non-helminth parasites and organisms in feces. However, there remains a need for a simple immunoassay method for the detection of a parasitic worm infection in feces, whole blood or in serum.

SUMMARY OF THE INVENTION

In one aspect, the invention is directed to an isolated antibody that can specifically bind to a tapeworm coproantigen such as *Taenia* coproantigen, e.g., *Taenia pisiformis* coproantigen or *Taenia taeniaeformis* coproantigen, or a *Dipylidium caninum* coproantigen. The antibody can be detectably labeled or attached to a solid support.

In one embodiment, the isolated antibody specifically binds to *Taenia pisiformis* coproantigen. The antibody does not specifically cross-react with one or more coproantigens selected from the group of: tapeworm *Taenia taeniaeformis*, tapeworm *Dipylidium*, hookworm (e.g., *Ancylostoma*), roundworm (*Toxocara*), whipworm (e.g., *Trichuris*), *Giardia* and parvovirus; the tapeworm *Dipylidium* is *Dipylidium caninum*; the hookworm is *Ancylostoma caninum* or *Ancylostoma tubaeforme*; the roundworm is *Toxocara canis* or *Toxocara cati*; the whipworm is *Trichuris vulpis* or *Trichuris felis*; the *Giardia* is *Giardia lamblia*; and the parvovirus is feline parvovirus or canine parvovirus.

In another embodiment, the isolated antibody specifically binds to *Taenia taeniaeformis* coproantigen. The antibody does not specifically cross-react with one or more coproantigens selected from the group of: tapeworm *Taenia pisiformis*, tapeworm *Dipylidium*, hookworm (e.g., *Ancylostoma*), roundworm (*Toxocara*), whipworm (e.g., *Trichuris*), *Giardia* and parvovirus; the tapeworm *Dipylidium* is *Dipylidium caninum*; the hookworm is *Ancylostoma caninum* or *Ancylostoma tubaeforme*; the roundworm is *Toxocara canis* or *Toxocara cati*; the whipworm is *Trichuris vulpis* or *Trichuris felis*; the *Giardia* is *Giardia lamblia*; and the parvovirus is feline parvovirus or canine parvovirus In other embodiments, the isolated antibody binds to *Dipylidium caninum* coproantigen. The antibody does not specifically cross-react with one or more coproantigens selected from the group of: tapeworm *Taenia*, tapeworm *Dipylidium*, hookworm (e.g., *Ancylostoma*), roundworm (*Toxocara*), whipworm (e.g., *Trichuris*), *Giardia* and parvovirus where the tapeworm *Taenia* is *Taenia pisiformis* or *Taenia taeniaeformis*; the hookworm is *Ancylostoma caninum* or *Ancylostoma tubaeforme*; the roundworm is *Toxocara canis* or *Toxocara cati*; the whipworm is *Trichuris vulpis* or *Trichuris felis*; the *Giardia* is *Giardia lamblia*; and the parvovirus is feline parvovirus or canine parvovirus.

In another aspect, the invention is directed to an immunocomplex comprising a tapeworm coproantigen and one or more antibodies specifically bound to the tapeworm coproantigen. In one embodiment, the tapeworm coproantigen can be the coproantigen from *Taenia pisiformis, Taenia taeniaeformis, Taenia crassiceps* or *Dipylidium caninum*. In another embodiment, the antibody is obtained by immunization with a whole extract of the tapeworm, E/S material of the tapeworm, Worm Wash of the tapeworm, or TCA soluble material of the tapeworm. In another embodiment, the antibody is specifically bound to a tapeworm coproantigen from a sample such as a fecal sample obtained from a tapeworm-infected mammal. In some embodiments, the mammal is further infected with one or more of roundworm, whipworm and hookworm and the antibody does not specifically bind to any antigen from the one or more of roundworm, whipworm, or hookworm that may be present in the sample. In some embodiments, the antibody can be detectably labeled or bound to a solid support.

In another aspect, the invention is directed immunocomplex comprising a tapeworm coproantigen, an antibody specifically bound to the tapeworm coproantigen, and a lectin bound to the tapeworm coproantigen. The lectin can bind specifically to one specific type of carbohydrate or can bind to two or more carbohydrates on the tapeworm coproantigen.

In another aspect, the invention provides a device for specifically binding and isolating helminthic antigens from a sample, for example coproantigens from a fecal sample, the device comprising a solid support, wherein the solid support has immobilized thereon one or more antibodies selected from the group consisting of (a) a first antibody capable of specifically binding coproantigen from a first tapeworm, but not coproantigen from a second tapeworm or coproantigen from a third tapeworm; (b) a second antibody capable of specifically binding the coproantigen from the second tapeworm, but not the coproantigen from the first tapeworm or the coproantigen from the third tapeworm; and (c) a third antibody capable of specifically binding the coproantigen from the third tapeworm, but not the coproantigen from the first tapeworm or the coproantigen from the second tapeworm. The device, may be, but is not limited to being, for example, an ELISA device, such as a lateral flow immunoassay device or microtiterplate device. Samples that may be tested for tapeworm by the device include, but are not limited to being, feces, digestive tract mucous, urine, whole blood, serum, mammary milk and whole tissue, such as tissue from mammary gland, intestine, liver, heart, lung, esophagus, brain, muscle, and eye, for example. The device further may include, but need not include, one or more reagents for the detection of one or more of the group consisting of: one or more helminthic worm parasites, non-worm parasites, one or more viruses, one or more fungi, one or more protozoa, and one or more bacteria. In some embodiments, the solid support further has immobilized thereon one or more antibodies selected from: (i) an antibody capable of specifically binding a roundworm coproantigen, but not a coproantigen derived from the group consisting of whipworm, hookworm, tapeworm, *Giardia* and parvovirus; (ii) an antibody capable of specifically binding a whipworm coproantigen, but not a coproantigen derived from the group consisting of roundworm, hookworm, tapeworm, *Giardia* and parvovirus; (iii) an antibody capable of specifically binding a hookworm coproantigen, but not a coproantigen derived from the group consisting of whipworm, roundworm, tapeworm, *Giardia* and parvovirus; (iv) an antibody capable of specifically binding *Giardia* coproantigen, but not coproantigen selected from the group consisting of roundworm coproantigen, whipworm coproantigen, hookworm coproantigen, tapeworm *Taenia* coproantigen, tapeworm *Dipylidium* coproantigen, and parvovirus coproantigen; and (v) an antibody capable of specifically binding parvovirus coproantigen, but not coproantigen selected from the group consisting of roundworm coproantigen, whipworm coproantigen, hookworm coproantigen, tapeworm *Taenia* coproantigen, tapeworm *Dipylidium* coproantigen, and *Giardia* coproantigen. In embodiments, the hookworm is *Anyclostoma*, the roundworm is *Toxocara* and the whipworm is *Trichuris*. In other embodiments, the hookworm is *Ancylostoma caninum* or *Ancylostoma tubaeforme*; the roundworm is *Toxocara canis* or *Toxocara cati*; the whipworm is *Trichuris vulpis* or *Trichuris felis*; the *Giardia* is *Giardia lamblia*; and the parvovirus is feline parvovirus or canine parvovirus.

In some embodiments, the solid support has immobilized thereon two or more antibodies, three or more antibodies, four or more antibodies, five or more antibodies, six or more antibodies, seven or more antibodies or or eight or more antibodies to allow for multiplexing.

In another aspect, the invention provides a device for detecting the presence or absence of one or more tapeworm coproantigens from a fecal sample; the device comprising a solid support, a lectin and one or more antibodies selected from the group consisting of: (a) a first antibody capable of specifically binding a coproantigen from a first tapeworm species, but not a coproantigen from a second tapeworm species or a coproantigen from a third tapeworm species; (b) a second antibody capable of specifically binding the coproantigen from the second tapeworm species, but not the coproantigen from the first tapeworm or the coproantigen from the third tapeworm species; and (c) a third antibody capable of specifically binding the coproantigen from the third tapeworm species, but not the coproantigen from the first tapeworm species or the coproantigen from the second tapeworm species, wherein the solid support has immobilized thereon one or more lectins or one or more antibodies. In some embodiments, the lectin is immobilized on the solid support. In other embodiments, the first, second and third antibodies are immobilized on the solid support. In other embodiments, the device further comprising one or more species of tapeworm antigen, wherein the one or more species of tapeworm antigen are specifically bound to the antibodies. In some embodiments, the first tapeworm species is *Taenia pisiformis*, the second tapeworm species is *Taenia taeniaeformis*, and/or the third tapeworm species is *Dipylidium caninum*.

In yet another aspect, the invention provides a method of detecting the presence or absence of one or more helminthic antigens in a sample, for example coproantigens from a fecal sample, the method comprising: (a) contacting a sample from a mammal with one or more antibodies selected from the group consisting of: (i) a first antibody capable of specifically binding coproantigen from a first tapeworm, but not coproantigen from a second tapeworm or coproantigen from a third tapeworm; (ii) a second antibody capable of specifically binding the coproantigen from the second tapeworm, but not the coproantigen from the first tapeworm or the coproantigen from the third tapeworm; and (iii) a third antibody capable of specifically binding the coproantigen from the third tapeworm, but not the coproantigen from the first tapeworm or the coproantigen from the second tapeworm; (b) forming antibody-coproantigen complexes in the presence of the coproantigens, if any, in the sample; and (c) detecting the presence or absence of the antibody-coproantigen complexes, if any. The coproantigens of tapeworm can include coproantigens of *Taenia* species, e.g., *Taenia pisiformis* and *Taenia taeniaeformis*; and *Dipylidium* species, e.g., *Dipylidium caninum*. In one embodiment, the step of detecting the presence or absence of the complexes further includes the step of providing a lectin that binds to at least one of the complexes. In some embodiments, the lectin can be detectably labeled or immobilized onto a solid support. In other embodiments, the first, second and third antibodies are detectably labeled or immobilized on a solid support. In some embodiments, the first, second and third antibodies can be immobilized on a solid support and the lectin can be detectably labeled. In other embodiments, first, second and third antibodies can be detectably labeled and the lectin can be immobilized on a solid support.

In another embodiment, wherein prior to the step of contacting the fecal sample from a mammal with at least one antibody, the method further comprising the step of contacting the fecal sample with one or more lectins. The one or more lectins can be detectably labeled or immobilized onto a solid support. Alternatively, the first, second and third antibodies can be detectably labeled or immobilized on a solid support. In one embodiment the first, second and third antibodies can be immobilized on a solid support and the one or more lectins can be detectably labeled. In another embodiment, the first, second and third antibodies can be detectably labeled and the one or more lectins can be immobilized on a solid support.

In one aspect, the method is carried out to test a fecal mammalian sample for tapeworm coproantigen. The method, however, is not limited to being carried out to test a fecal sample. In addition to feces, the sample therefore may be, but is not limited to being whole blood, serum, mammary milk and whole tissue, such as tissue from mammary gland, intestine, liver, heart, lung, esophagus, brain, muscle, and eye, for example.

In yet another aspect, the invention provides a method of diagnosing whether a mammal is infected with one or more parasitic worms, the method comprising the steps of: (a) contacting a sample from a mammal with one or more antibody selected from the group consisting of: (i(i) a first antibody capable of specifically binding coproantigen from a first tapeworm, but not coproantigen from a second tapeworm or coproantigen from a third tapeworm; (ii) a second antibody capable of specifically binding the coproantigen from the second tapeworm, but not the coproantigen from the first tapeworm or the coproantigen from the third tapeworm; and (iii) a third antibody capable of specifically binding the coproantigen from the third tapeworm, but not the coproantigen from the first tapeworm or the coproantigen from the second tapeworm; (b) forming antibody-coproantigen complexes in the presence of the coproantigens, if any, in the sample; (c) detecting the presence or absence of the antibody-coproantigen complexes, if any; and (d) diagnosing the mammal as having: (i) a first tapeworm infection if a first tapeworm antibody-coproantigen complex is present; (ii) a second tapeworm infection if a second tapeworm antibody-coproantigen complex is present; and (iii) a third tapeworm infection if a third tapeworm antibody-coproantigen complex is present. In one embodiment, two or more antibodies, three or more antibodies, four or more antibodies, five or more antibodies, six or more antibodies, seven or more antibodies or eight or more antibodies are selected. In some embodiments, the step of detecting the presence or absence of the complexes further includes the step of providing one or more lectins that binds to at least one of the complexes. In some embodiments, the lectin can be detectably labeled or immobilized onto a solid support. In other embodiments, the first, second and third antibodies are detectably labeled or immobilized on a solid support. In some embodiments, the first, second and third antibodies can be immobilized on a solid support and the lectin can be detectably labeled. In other embodiments, first, second and third antibodies can be detectably labeled and the lectin can be immobilized on a solid support.

In another embodiment, wherein prior to the step of contacting the fecal sample from a mammal with at least one antibody, the method further comprising the step of contacting the fecal sample with one or more lectins. The lectin can be detectably labeled or immobilized onto a solid support. Alternatively, the first, second and third antibodies can be detectably labeled or immobilized on a solid support. In one embodiment the first, second and third antibodies can be immobilized on a solid support and the lectin can be detectably labeled. In another embodiment, the first, second and third antibodies can be detectably labeled and the lectin can be immobilized on a solid support.

In a further aspect, the invention provides a method of diagnosing and treating a mammal infected with one or more parasitic worms, the method comprising the steps of: (a) contacting a sample from a mammal with at least one antibody selected from the group consisting of: (i(i) a first antibody capable of specifically binding coproantigen from a first tapeworm, but not coproantigen from a second tapeworm or coproantigen from a third tapeworm; (ii) a second antibody capable of specifically binding the coproantigen from the second tapeworm, but not the coproantigen from the first tapeworm or the coproantigen from the third tapeworm; and (iii) a third antibody capable of specifically binding the coproantigen from the third tapeworm, but not the coproantigen from the first tapeworm or the coproantigen from the second tapeworm; (b) forming antibody-coproantigen complexes in the presence of the coproantigens, if any, in the sample; (c) detecting the presence or absence of the antibody-coproantigen complexes, if any; and (d) diagnosing the mammal as having: (i) a first tapeworm infection if a first tapeworm antibody-coproantigen complex is present; (ii) a second tapeworm infection if a second tapeworm antibody-coproantigen complex is present; and (iii) a third tapeworm infection if a third tapeworm antibody-coproantigen complex is present; and (e) administering an effective amount of one or more therapeutic agents to treat the mammal having the first, second, or their tapeworm infection or combination thereof. In one embodiment, two or more antibodies are selected. In other embodiments, step (e) further includes one or more additional therapeutic agents to treat infection by one or more helminthic worm parasites, one or more non-worm parasites, one or more viruses, one or more fungi, one or more protozoa, or one or more bacteria. In other embodiments, step (e) further includes one or more therapeutic agents to control, repel or kill an intermediate host of a platyhelminthic worm parasite, helminthic worm parasite, non-worm parasite, virus, fungus, or bacterium. Representative examples of intermediate hosts include fleas and canine chewing lice which can carry tapeworm eggs.

In further embodiments of the above methods, step (a) group further consists of: (i) an antibody capable of specifically binding a roundworm coproantigen, but not a coproantigen derived from the group consisting of whipworm, hookworm, tapeworm, *Giardia* and parvovirus; (ii) an antibody capable of specifically binding a whipworm coproantigen, but not a coproantigen derived from the group consisting of roundworm, hookworm, tapeworm, *Giardia* and parvovirus; (iii) an antibody capable of specifically binding a hookworm coproantigen, but not a coproantigen derived from the group consisting of whipworm, roundworm, tapeworm, *Giardia* and parvovirus; (iv) an antibody capable of specifically binding *Giardia* coproantigen, but not coproantigen selected from the group consisting of roundworm coproantigen, whipworm coproantigen, hookworm coproantigen, tapeworm *Taenia* coproantigen, tapeworm *Dipylidium* coproantigen, and parvovirus coproantigen; and (v) an antibody capable of specifically binding parvovirus coproantigen, but not coproantigen selected from the group consisting of roundworm coproantigen, whipworm coproantigen, hookworm coproantigen, tapeworm *Taenia* coproantigen, tapeworm *Dipylidium* coproantigen, and *Giardia* coproantigen. In some embodiments, the hookworm is *Anyclostoma*, the roundworm is *Toxocara* and the whipworm is *Trichuris*. In other embodiments, the hookworm is *Ancylostoma caninum* or *Ancylostoma tubaeforme*; the roundworm is *Toxocara canis* or *Toxocara cati*; the whipworm is *Trichuris vulpis* or *Trichuris felis*; the *Giardia* is *Giardia lamblia*; and the parvovirus is feline parvovirus or canine parvovirus. Thus, the fecal sample is contacted with at two or more antibodies, three or more antibodies, four or more antibodies, five or more antibodies, six or more antibodies, seven or more antibodies or eight or more antibodies to allow for multiplexing.

In further embodiments of the above methods, step (d) diagnosing further comprises: a roundworm infection if a roundworm antibody-coproantigen complex is present; a whipworm infection if a whipworm antibody-coproantigen complex is present; a hookworm infection if a hookworm antibody-coproantigen complex is present; a *Giardia* infection if a *Giardia* antibody-coproantigen complex is present; and a parvovirus infection if a parvovirus antibody-coproantigen complex is present.

In some embodiments, the step of detecting the presence or absence of the complexes further includes the step of providing one or more lectins that binds to at least one of the complexes. In some embodiments, the lectin can be detectably labeled or immobilized onto a solid support. In other embodiments, the first, second and third antibodies are detectably labeled or immobilized on a solid support. In some embodiments, the first, second and third antibodies can be immobilized on a solid support and the lectin can be detectably labeled. In other embodiments, first, second and third antibodies can be detectably labeled and the lectin can be immobilized on a solid support.

The method may also be used to test for and distinguish between environmental contamination with tapeworm. Environmental samples that may be tested for tapeworms by the device include, but are not limited to soil, decomposing material, or fecal matter from residential settings including yards, gardens, sand boxes, playgrounds. Testing locations may also include parks, beaches, forests, farms, or other locations exposed to fecal material from dogs, cats, or other mammalian hosts of tapeworms. Feces from indoor and outdoor litter boxes may also be tested.

In yet another aspect, the present invention includes a kit for carrying out one or more steps of the method of the invention. The kit may optionally include, for example, the device and one or more of the compositions of the present invention and instructions for carrying out the method of the present invention. The kit may further optionally include, for example, one or more indicator reagents, one or more antibody labeling compounds, one or more antibodies, one or more antigen capture reagents, one or more inhibitors, and one or more wash reagents to be used as part of the device and/or to be used in carrying out the method.

BRIEF DESCRIPTION OF THE DRAWINGS

In FIG. 19, columns 1 through 12 are an image of a single microtiter plate, and columns 13 and 14 are an image of another, separate microtiter plate.

In FIG. 20, columns 1 through 12 are an image of a single microtiter plate.

DETAILED DESCRIPTION OF THE PREFERRED EMBODIMENTS OF THE INVENTION

I. Introduction

Figure 1:
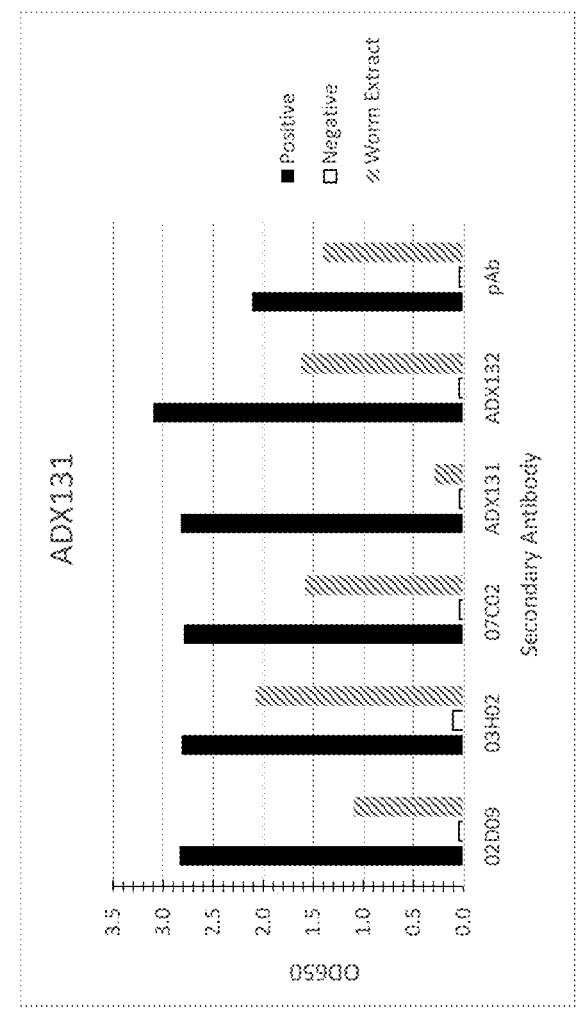
FIG. 1 shows the OD determinations of antibody ADX131 against worm extract and fecal extract from canines that are negative or positive for tapeworm infection by following the method of the present invention as shown in Example 1A. Positive=Fecal extract (FEX) from *T. pisiformis* infected dog; Negative=FEX from dog not infected with *T. pisiformis*; Worm Extract=*T. pisiformis* worm extract (WE).

The present invention is generally directed to methods, devices, and kits for detecting and distinguishing between tapeworm species in a fecal sample obtained from a mammal. The present invention relates to tapeworm coproantigens from a variety of tapeworm species including *Taenia pisiformis, Taenia taeniaeformis*, and *Dipylidium caninum*. In particular, the present invention relates methods, devices and kits for detecting tapeworm infection and distinguishing between two or more tapeworm species.

The present invention provides a superior alternative to the existing microscopic inspection techniques. This is true because the present invention provides devices, kits and methods for detecting the presence or absence of tapeworm in a sample from a mammal that: (1) are both easy to use and yield consistently reliable results; (2) allow for the absence or presence of a specific tapeworm species in a mammal to be confirmed regardless of whether that mammal is infected with one or more tapeworm species and/or other helminthic worm parasites such as hookworm, roundworm, whipworm and/or heartworm; (3) can detect tapeworm prior to the time that the ova and protoglottids first appear in the infected host's feces; and (4) can distinguish between different tapeworm species as well as helminthic worm parasites such as roundworm, whipworm and hookworm infections.

The present invention is based in part on the discovery of unexpected properties of compositions specific to tapeworm infections. Specifically, it was determined that antibodies raised against tapeworm specific polypeptides (or raised against an extract of whole tapeworm, E/S material of the tapeworm, Worm Wash of the tapeworm, or TCA soluble material of the tapeworm) can be used to capture, detect, and distinguish between tapeworm antigens from different species in a mammal. The specificity for each type of tapeworm species is surprising because tapeworms are related cesotodes, and an antibody raised against a protein isolated from any one of these tapeworm species would be expected to crossreact with one or more of the other tapeworms species, host antigens, or other host components.

It was further determined that this antibody can be used to capture and detect tapeworm antigens in a mammal before eggs and protglottids are visible in feces. This ability to detect tapeworm so soon after infection, and before the appearance of any ova in the feces of the infected mammal, is surprising because ova and protglottides generally do not appear in the feces of an infective host until weeks after the host becomes infected.

The present invention therefore includes methods, devices, and kits that use antibodies and/or fragments thereof to specifically capture and detect and distinguish between antigen of different tapeworm species in a mammal. The ability of the present invention to detect and diagnose a specific tapeworm species even when one or more other tapeworm species or different worm types are also present allows the mammal's caregiver the opportunity to optimally select a treatment for ridding the tapeworm as well as other worms such as roundworm, whipworm and/or hookworm from the mammal. Further, the ability of the present invention to, in some cases, detect tapeworm before eggs and protglottids appear in feces provides the possibility that the caregiver may begin such treatment before the mammal becomes severely sickened. An intervention prior to appearance of ova and protglottids in the feces would also greatly reduce or eliminate the possibility that the infestation is spread to other animals or humans.

II. Definitions and Uses of Term

The term "compositions of the invention" refers to all of the nucleic acids, polypeptides, glycoproteins, carbohydrates, glycolipids, antibodies, and mixtures that include one or more of those nucleic acids, polypeptides, glycoproteins, carbohydrates, glycolipids, and antibodies and one or more other compounds, that can be used to detect the presence or absence of tapeworm in a sample obtained from a mammal by carrying out the method of the present invention that are explicitly described, implicitly encompassed or otherwise disclosed herein.

"A sample from a mammal" in which tapeworm can be detected by the present invention includes all bodily components and extracts thereof, such as any fluid, solid, cell or tissue, that are capable of tapeworm antigen. Exemplary samples therefore include, but are not limited to being, feces, milk, whole blood and portions thereof, including serum, and further include tissue extracts, including tissue from mammary gland, intestine, liver, heart, lung, esophagus, brain, muscle, and eye, for example. The sample may be taken directly from the mammal or the sample may be taken from anything that has contacted the mammal. For example, the sample may be fresh or decaying fecal droppings from the mammal. As another example, the sample may include soil, dirt, sand, plant material, or any other material that may be mixed with bodily components that may be left behind by a mammal, such as feces, for example. As such, the sample may be taken from an environmental source, including soil, decomposing material, or fecal matter from forests, farms, or residential settings, including litter boxes, yards, gardens, sand boxes, playgrounds, parks, and beaches. No matter the origin or the content of the sample, this sample sometimes is referred to herein as the "sample", the "mammalian sample", the "test sample" or the "sample under test".

As used herein, "nucleic acid" is synonymous with, and therefore is used interchangeably with, "gene", "DNA", "cDNA", "EST", "polynucleotide", "oligonucleotide", "polynucleic acid", "RNA" and "mRNA". A nucleic acid may be in double-stranded form or it may be in single-stranded form. Further, a nucleic acid is either naturally isolated, such as from a whole tapeworm or a portion thereof, for example, or it is artificially synthesized, either in a recombinant host organism or by any other artificial means known to the skilled artisan, such as by employing a PCR-based technique, by creating a transgenic organism that synthesizes the nucleic acid, by using a DNA synthesizing machine, or by any another molecular-based technique, for example.

"Polypeptide", "peptide" and "protein" are synonymous terms that are used interchangeably herein to refer to a polymer of amino acid residues. A polypeptide, peptide and protein of the present invention may be either naturally isolated, such as from a whole tapeworm or from a portion of tapeworm for example, or artificially synthesized, either in a recombinant host organism or by any other artificial means known to the skilled artisan. A polypeptide, peptide and protein of the present invention may be glycosylated.

The term "antibody" or "antibody of the present invention" refers to any antibody that is able to specifically bind to one or more antigens for the particular worm without binding to antigens from the other worms. For example antibodies to the one tapeworm species are able to specifically bind to the antigens of the tapeworm species, but not to any antigens from different tapeworm species. The antibodies of the present invention may be raised against one or more immunogenic polypeptides, glycoproteins, carbohydrates, or glycolipids of the present invention. Unless otherwise stated, it is to be understood that the antibody of the present invention may include a mixture of two or more different types of antibody. For example, the antibody may be a mixture of two types of antibodies, wherein one of the two types specifically binds to one particular antigen and the other of the two types specifically binds to some other antigen.

The term "first antibody" as used herein means one or more antibodies capable of specifically binding a coproantigen from a first tapeworm species, but not coproantigen from a second tapeworm species or coproantigen from a third tapeworm species.

The term "second antibody" as used herein means one or more antibodies capable of specifically binding the coproantigen from the second tapeworm species, but not the coproantigen from the first tapeworm species or the coproantigen from the third tapeworm species.

The term "third antibody" as used herein means one or more antibodies capable of specifically binding the coproantigen from the third tapeworm species, but not coproantigen from the first tapeworm species or the coproantigen from the third tapeworm species.

The "immunogenic polypeptide of the present invention" and, more simply, "the polypeptide of the present invention", is an immunogen against which the antibodies of the present invention may be raised. All "polypeptides of the present invention" are immunogenic and therefore may be used to elicit an immune response in a host animal to produce the antibodies of the present invention. Unless otherwise stated, it is to be understood that the polypeptide of the present invention may be one component of a mixed composition of a plurality of components.

An "immunogen" is any agent, such as the immunogenic extract, polypeptide, glycoprotein, carbohydrate, or glycolipid of the present invention, for example, that is capable of eliciting an immune response in an animal that is exposed to that agent.

The term "tapeworm", as used herein, refers to platyhelminths worm parasites such as intestinal tapeworms which includes the genera *Taenia* and *Dipylidium*. Thus, the term "tapeworm", as used herein, does not refer to the entirety of the class cestoda, but rather to the subclass eucestoda, including the order pseudophyllidea. Representative examples of tapeworm include *Taenia pisiformis, Taenia taeniaeformis, Taenia crassiceps, Dipylidium caninum, Diphyllobothrium mansonoide, Diphyllobothrium latum,* and *Spirometra erinaceieuropaei*.

A "tapeworm coproantigen" or a "coproantigen from tapeworm" is any tapeworm product that is present in the feces of a mammal having a tapeworm infection and that may be specifically bound by one or more of the antibodies of the invention. For example, a tapeworm coproantigen may be, but is not limited to being, one or more of the polypeptides of the invention.

The term "roundworm", as used herein, refers to helminths such as intestinal roundworms of the order Ascaridida, which includes the genera *Toxocara, Toxascaris, Baylisascaris, Ascaridia, Parascaris, Ascaris, Anisakis,* and *Pseudoterranova*. Exemplary roundworms therefore include *Toxocara canis, Toxocara cati* and *Toxascaris leonina*. Thus, the term "roundworm", as used herein, does not refer to the entirety of the phylum Nematoda. Therefore, "roundworm" does not include any member of the genera *Ancylostoma, Uncinaria, Necator, Trichuris, Wuchereria, Brugia* or *Dirofilaria*.

A "roundworm coproantigen" or a "coproantigen from roundworm" is any roundworm product that is present in the feces of a mammal having a roundworm infection and that may be specifically bound by one or more of the antibodies of the invention. For example, a roundworm coproantigen may be, but is not limited to being, a novel C-terminal 7 kD isoform of DIV6728, which is a excretory/secretory protein of *T. canis*, is present in feces of *T. canis*-infected canines as early as 38 days after the canines first became infected with the *T. canis*. Therefore, a "roundworm coproantigen" may be this novel C-terminal 7 kD isoform of DIV6728 (which is referred to herein as "Copro6728") that has been observed in canine feces as discussed in U.S. Pat. No. 7,951,547.

The term "whipworm", as used herein, refers to helminths such as intestinal whipworms of the genera *Trichuris* and *Trichocephalus*. Exemplary whipworms therefore include *Trichuris vulpis, Trichuris campanula, Trichuris serrata, Trichuris felis, Trichuris suis, Trichuris trichiura, Trichuris discolor* and *Trichocephalus trichiuris*. Further, the term "whipworm", as used herein, does not refer to the entirety of the phylum Nematoda. For example, "whipworm" does not include any member of the genera *Ancylostoma, Uncinaria, Necator, Toxocara, Toxascaris, Ascaris, Wuchereria, Brugia* or *Dirofilaria*.

A "whipworm coproantigen" or a "coproantigen from whipworm" is any whipworm product that is present in the feces of a mammal having a whipworm infection and that may be specifically bound by one or more of the antibodies of the invention. For example, a whipworm coproantigen may be, but is not limited to being, "DIV6901" or "DIV6902, hereinafter, this particular antibody is referred to as "anti-DIV6901" or "anti-DIV6902" as discussed in U.S. Pat. No. 7,951,547.

The term "hookworm," as used herein, refers to helminthes such as intestinal hookworm of the genera *Ancylostoma, Necator* and *Uncinaria*. Exemplary hookworms therefore include *Ancylostoma caninum, Ancylostoma braziliense, Ancylostoma duodenal, Ancylostoma ceylanicum, Ancylostoma tubaeforme* and *Ancylostoma pluridentatum, Necator americanus,* and *Uncinaria stenocephala*. Further, the term "hookworm," as used herein, does not refer to the entirety of the phylum Nematoda. For example, "hookworm" does not include any member of the genera *Trichuris, Trichocephalus Toxocara, Toxascaris, Ascaris, Wuchereria, Brugia* or *Dirofilaria*.

A "hookworm coproantigen" or a "coproantigen from hookworm" is any hookworm product that is present in the feces of a mammal having a hookworm infection and that may be specifically bound by one or more of the antibodies of the invention. For example, a hookworm coproantigen may be, but is not limited to being, a novel N-terminal 28 kDa isoform of ASP5, which is a excretory/secretory protein of *Ancylostoma*, present in feces of *Ancylostoma*-infected canines as early as 9 days after the canines first became infected with the *Ancylostoma*. Therefore, a "hookworm coproantigen" may be this novel N-terminal 28 kDa isoform of ASP5 (which is referred to herein as "CoproASP5") that has been observed in canine feces as discussed in U.S. Pat. No. 7,951,547.

The term "*Giardia*", as referred herein, refers to protozoans of the genus *Giardia*. Exemplary *Giardia* species therefore include *Giardia lamblia*, also known as *Giardia intestinalis*.

A "*Giardia* coproantigen" or "coproantigen of *Giardia*" is any *Giardia* product that is present in the feces of a mammal having a *Giardia* infection and that may be specifically bound by one or more of the antibodies of the invention.

"Lectins" are proteins that recognize and bind specific monosaccharide or oligosaccharide structures (carbohydrates). A lectin usually contains two or more binding sites for carbohydrate units. The carbohydrate-binding specificity of a certain lectin is determined by the amino acid residues that bind the carbohydrate. The binding strength of lectins to carbohydrates can increase with the number of molecular interactions. The dissociation constant for binding of lectins to carbohydrates is about $K_d$ of $10^{-5}$ to $10^{-7}$. Lectins can be labeled with any type of label known in the art, including, for example, fluorescent, chemiluminescent, radioactive, enzyme, colloidal metal, radioisotope and bioluminescent labels.

In embodiments of the invention, lectins used are those that specifically bind tapeworm coproantigen. In embodiments of the invention lectins that specifically bind O-glycosylated proteins are useful in the invention. Such lectins include, for example, ECL lectin (*Erythina cristagalli*), GSL I (*Griffonia Simplicifolia* Lectin I), GSL II (*Griffonia Simplicifolia* Lectin II), jacalin, LCA lectin (*Lens culinaris*), RCA 123 (*Ricinus Communis*), and PSA lectin (*Phaseolus vulgaris* leucoagglutinin), WGA (wheat germ agglutinin) and sWGA (succinylated wheat germ agglutinin). Lectins are commercially available from, e.g., Vector Laboratories, Burlingame, Calif., USA.

Lectins can be used that specifically bind to carbohydrates on human, canine, feline, equine, bovine, ovine, or simian tapeworm antigens.

"Specific for", "specifically binds", and "stably binds" means that a particular composition of the invention, such as an antibody, polypeptide, or oligonucleotide of the present invention, for example, recognizes and binds to one or more other agents with greater affinity than to at least one other agent. As one example, an antibody of the present invention is said to be "specific for", to "specifically bind", and to "stably bind" tapeworm antigens whenever that antibody is able to recognize and bind to those roundworm antigens with greater affinity than to any other antigens from a non-tapeworm parasitic worm. Such binding specificity can be tested using methodology well known in the art, for example, ELISA or a radioimmunoassay (RIA). Based on information observed regarding the binding specificity of a particular composition of the invention, the method of the present invention can be carried out under conditions that allow that composition to bind to (and therefore to allow the detection of such binding to) a particular agent or agents, but not to significantly bind other agents, while those conditions are maintained. As one example, the method of the present invention can be carried out under conditions that allow an antibody of the present invention to bind to (and therefore to allow the detection of such binding to) one or more antigens of a species of tapeworm antigens present in a particular sample, but not significantly to any antigen from other tapeworm species or other helminthic worm species may be present in that sample, thereby allowing for the distinction between species of tapeworms and roundworm, whipworm and hookworm.

"Detecting tapeworm" means detecting one or more tapeworm-specific products, including one or more of the polypeptides, antibodies and nucleic acids of the present invention, or one or more tapeworm antigens, for example. The presence of one or more such tapeworm products in a sample from a mammal is indicative that the mammal has a tapeworm infection, regardless of whether any whole tapeworm organism or ovum thereof is also present in that sample. Conversely, the absence of one or more such tapeworm products a sample from a mammal is indicative that the mammal does not have a tapeworm infection.

"Treatment" means the administration of a therapeutic agent to a patient by any suitable administration route to reduce or eliminate parasitic worms (helminths) or other internal parasites from the body either by controlling, stunning or killing them and/or that reduces or eliminates infestation by intermediate hosts such as insects, e.g. fleas, which can transmit infection with parasitic worms or other internal parasites, without causing significant damage to the patient.

III. Antibodies of the Invention

The present invention further includes antibodies and antigen-binding fragments thereof that are raised against and that specifically bind all or part of one or more polypeptides of the present invention, and also includes compositions that include said antibodies and antigen-binding fragments thereof. When contacted to a sample obtained from a mammal, these antibodies and antigen-binding fragments are able to specifically bind to a particular helminthic worm antigen. For example the tapeworm antibodies and antigen-binding fragments are able to specifically bind tapeworm antigens present in the sample, but are not able to specifically bind any antigen from other worms such as roundworm, hookworm or whipworm that may be present in the sample. The antibodies of the present invention are suitable for being used only to capture one or more tapeworm antigens, only to detect one or more tapeworm antigens, or more preferably, to both capture and detect one or more tapeworm antigens.

The antibodies of the present invention may belong to any antibody class, including for example, IgG, IgM, IgA, IgD and IgE, and may be prepared by any of a variety of techniques known to the skilled artisan. (See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68(1992); Harlow and Lane, *Antibodies: A Laboratory Manual*, Cold Spring Harbor Laboratory (1988); and *Making and Using Antibodies: A Practical Handbook*, Howard and Kaser, eds., CRC Press (2006), each one of which is incorporated herein by reference in its entirety.)

In one technique, the polypeptide of the invention is introduced into a host animal, such as into rabbit, mouse, rat, guinea pig, goat, pig, cow, sheep, donkey, dog, cat, chicken, or horse, for example. An enhanced immune response may be elicited in the host animal by associating the polypeptide with a carrier and/or by exposing the host to an adjuvant, but it is to be understood that the present invention does not require that the polypeptide be associated with a carrier or that the host be exposed to the adjuvant. An exemplary carrier that may be used for this purpose is bovine serum albumin, bovine thyroglobulin, and soybean trypsin inhibitor. Exemplary adjuvants include Freund's complete or incomplete adjuvant and MDL-TDM adjuvant. Regardless of whether the polypeptide is associated with such a carrier or whether the host is exposed to an adjuvant, booster immunizations optionally may be made with the host animal being bled one or more times thereafter. Polyclonal antibodies (pAbs) that specifically bind the polypeptide may then be purified from antisera obtained from the bleed or bleeds. Such purification may be achieved, for example, by employing affinity chromatography techniques that involve associating the polypeptide to a solid support. Such affinity chromatography techniques are well known by the skilled artisan.

In several embodiments, the tapeworm antibody of the present invention is an antibody that is raised in rabbit by immunizing that host animal with extract of whole tapeworm, E/S material of the tapeworm, Worm Wash of the tapeworm, or TCA soluble material of the tapeworm, as described below.

It is also to be understood that the antibodies of the invention optionally may be polyclonal or monoclonal antibodies (mAbs), single chain antibodies (scFv), chimeric antibodies, and fragments thereof. Monoclonal antibodies that are specific for the polypeptide of interest may be obtained and purified, for example, by preparing cell lines that generate antibodies having the desired specificity to the polypeptide of interest. Cell lines of this kind may be derived from cells of a particular type (e.g., spleen cells) that are isolated from a host animal that had previously been immunized with the polypeptide as described before. In such a case, these cells could then be immortalized, for example, by fusing them with myeloma cells by carrying out any one of a variety of fusion techniques known to the skilled artisan. In one exemplary technique, the cells from the immunized host animal are co-incubated with their fusion partner, e.g., the myeloma cells, in the presence of a detergent for a short period of time before being plated on a medium that supports the growth of hybrid cells (but not the myeloma fusion partner). Such selection may be achieved, for example, by using hypoxanthine, aminopterin, and thymidine (HAT). When hybrid cells emerge during selection, in perhaps one or two weeks after commencing the selection process, single hybrid colonies (and their supernatants) are tested for their ability to bind the polypeptide or polypeptides against which the host animal was immunized. Hybrid colonies having the most optimal binding specificity would represent the best candidates from which monoclonal antibodies may be isolated. These monoclonal antibodies, for example, may be isolated directly from the supernatant (i.e., medium) in which these colonies are grown by employing any one of a variety techniques known to the skilled artisan.

The antibodies of the invention also may be a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F$_v$ fragments. In addition to production and purification from animals or mammalian cells, antibodies, antibody fragments, or non-antibody scaffolds can be selected based upon various in vitro technologies, including phage display, ribosomal display, or bacterial display.

Antibodies, including secondary antibodies, may be labeled with any type of label known in the art, including, for example, fluorescent, chemiluminescent, radioactive, enzymes, colloidal particles, radioisotopes and bioluminescent labels. In various embodiments of the invention, the one or more of the antibodies of the invention are labeled with an enzyme, a colloidal particle, a radionuclide or a fluorophor. The particulate label can be, for example, a colored latex particle, dye sol, or gold sol conjugated to an antibody.

IV. Methods, Devices and Kits of the Invention

A. Devices and Kits of the Invention

The present invention, in one aspect, is a detecting the presence or absence of one or more tapeworm antigens from a sample, the device comprising a solid support, wherein the solid support has immobilized thereon one or more antibodies selected from the group consisting of (a) a first antibody capable of specifically binding coproantigen from a first tapeworm, but not coproantigen from a second tapeworm or coproantigen from a third tapeworm; (b) a second antibody capable of specifically binding the coproantigen from the second tapeworm, but not the coproantigen from the first tapeworm or the coproantigen from the third tapeworm; and (c) a third antibody capable of specifically binding the coproantigen from the third tapeworm, but not the coproantigen from the first tapeworm or the coproantigen from the second tapeworm; and optionally, (d) one or more types of *Giardia* coproantigen, roundworm coproantigen, whipworm coproantigen, and/or hookworm coproantigen, wherein the one or more types of roundworm coproantigen, whipworm coproantigen, and hookworm coproantigen are specifically bound to the antibodies. See U.S. Pat. No. 7,951,547, which is incorporated by reference in its entirety. The device is arranged to aid specifically binding and isolating tapeworm coproantigens from any *Giardia*, roundworm, whipworm and hookworm antigen in a sample from a mammal.

In one aspect, the device includes a solid support, wherein one or more antibodies of the invention are immobilized on the solid support. The solid support may be, but is not limited to being, the inner, bottom surface of a well of a microtiter plate, a microparticle, the channels of a microfluidic device, a cartridge, a membrane, or a substrate that is included as part of a lateral flow device, for example. An exemplary microtiter plate is an Immulon 1B 96-well plate (which is commercially available from Thermo Scientific of Milford, Mass.), but it is to be understood that the skilled artisan will recognize that a large variety of other microtiter plates that are not the Immulon 1B 96-well plate allow for the immobilization of antibodies thereon, and therefore would be suitable for providing the solid support of the present invention.

An exemplary lateral flow device is the lateral flow device that is described in U.S. Pat. No. 5,726,010, which is incorporated herein by reference in its entirety. The device for performing a lateral flow assay may be a SNAP® device, which is commercially available from IDEXX Laboratories, Inc. of Westbrook, Me. However, it is to be understood that the skilled artisan will recognize that a large variety of other lateral flow devices that are not SNAP® devices or described by U.S. Pat. No. 5,726,010 allow for the immobilization of an antibody thereon, and therefore would be suitable for being used as the device of the present invention. These devices can include, for example, lateral flow devices that use colloidal gold technology.

Antibodies used in the device of the invention may be immobilized on the solid support by any methodology known in the art, including, for example, covalently or non-covalently, directly or indirectly, attaching the antibodies to the solid support. Therefore, while these antibodies may be attached to the solid support by physical adsorption (i.e., without the use of chemical linkers), it is also true that these antibodies may be immobilized to the solid support by any chemical binding (i.e., with the use of chemical linkers) method readily known to one of skill in the art.

In some embodiments, the first antibody can be raised against a whole extract of the first tapeworm species, E/S material of the first tapeworm species, Worm Wash material of the first tapeworm species, or TCA soluble material of the first tapeworm species; (b) the second antibody can be raised against a whole extract of the second tapeworm species, E/S material of the second tapeworm species, Worm Wash material of the first tapeworm species, or TCA soluble material of the second tapeworm species; or (c) the third antibody can be raised against a whole extract of the third tapeworm species, E/S material of the third tapeworm species, Worm Wash material of the first tapeworm species, or TCA soluble material of the third tapeworm species.

In some embodiments, the solid support further has immobilized thereon one or more antibodies selected from: an antibody capable of specifically binding a roundworm coproantigen, but not a whipworm or hookworm coproantigen; an antibody capable of specifically binding a whipworm coproantigen, but not a roundworm or hookworm coproantigen; an antibody capable of specifically binding a hookworm coproantigen, but not a whipworm or roundworm coproantigen; an antibody capable of specifically binding *Giardia* coproantigen, but not coproantigen selected from the group consisting of roundworm coproantigen, whipworm coproantigen, hookworm coproantigen, tapeworm *Taenia* coproantigen, tapeworm *Dipylidium* coproantigen, and parvovirus coproantigen; and an antibody capable of specifically binding parvovirus, but not coproantigen selected from the group consisting of roundworm coproantigen, whipworm coproantigen, hookworm coproantigen, tapeworm *Taenia* coproantigen, tapeworm *Dipylidium* coproantigen, and *Giardia* coproantigen. In embodiments, the hookworm is *Anyclostoma*, the roundworm is *Toxocara* and the whipworm is *Trichuris*. In other embodiments, the hookworm is *Ancylostoma caninum* or *Ancylostoma tubaeforme*; the roundworm is *Toxocara canis* or *Toxocara cati*; the whipworm is *Trichuris vulpis* or *Trichuris felis*; the *Giardia* is *Giardia lamblia*; and the parvovirus is feline parvovirus or canine parvovirus.

It is also to be understood that the solid support may be any suitable material for the immobilization of the antibodies of the invention. For example, the solid support may be beads, particles, tubes, wells, probes, dipsticks, pipette tips, slides, fibers, membranes, papers, natural and modified celluloses, polyacrylamides, agaroses, glass, polypropylene, polyethylene, polystyrene, dextran, nylon, amylases, plastics, magnetite or any other suitable material readily known to one of skill in the art. In some embodiments, the solid support may comprise a plurality of particles, microparticles, chips or beads. The plurality of particles, microparticles, chips or beads may be attached to the device, or be loosely associated with the device. The plurality of particles, microparticles, chips or beads may be situated on the surface of the device or within the device. The plurality of particles, microparticles or beads may be stationary on or within the device, or they may be able to move within or through the device.

The device optionally may include one or more labeled antigen capture reagents that may be mixed with a sample from a mammal prior to application to a device of the invention. When the labeled capture antigen reagent is included, the labeled antigen capture reagent may or may not be deposited or dried on a solid surface of the device. "Antigen capture reagent" refers to any compound that is specific for the antigen or antigens of interest. The labeled antigen capture reagent, whether added to the mammalian sample or pre-deposited on the device, may be, for example, a labeled antibody specific for a roundworm antigen, including, but not limited to, the antibodies of the present invention.

The device also may optionally include a liquid reagent that transports (such as when the device is a SNAP® device, for example), or otherwise facilitates removal of (such as when the device includes a microtiter plate, for example), unbound material (e.g., unreacted portions of the mammalian sample, such as, for example, unreacted portions of fecal extract, and unbound antigen capture reagent) away from the reaction zone (solid phase). The liquid reagent may be a wash reagent and serve only to remove unbound material from the reaction zone, or it may include a detector reagent and serve to both remove unbound material and facilitate antigen detection. For example, in the case of an antigen capture reagent conjugated to an enzyme, the detector reagent includes a substrate that produces a detectable signal upon reaction with the enzyme-antibody conjugate at the reaction zone (solid phase). Alternatively, in the case of a labeled antigen capture reagent conjugated to a radioactive, fluorescent, or light-absorbing molecule, the liquid reagent acts merely as a wash solution facilitating detection of complex formation at the reactive zone by washing away unbound labeled reagent.

The liquid reagent may further include a limited quantity of an "inhibitor", i.e., a substance that blocks the development of the detectable end product. A limited quantity is defined as being an amount of inhibitor sufficient to block end product development until most or all excess, unbound material is transported away from the second region, at which time detectable end product is produced.

The device of the present invention may also include various binding reagents immobilized at locations distinct from the antigen capture reagent or reagents. For example, an immunoreagent (an antibody, antigen or polypeptide) that recognizes a species-specific (e.g., roundworm-specific) antibody portion of a labeled antibody or antigen capture reagent, or an enzyme portion of an enzyme-labeled reagent, can be included as a positive control to assess the viability of the reagents within the device. For example, a positive control may be an anti-horseradish peroxidase antibody that has been raised in, for example, goat or mouse. Additionally, a reagent, e.g., an antibody, isolated from a non-immune member of the species from which the antibody portion of the antigen-antibody complex was derived can be included as a negative control to assess the specificity of immunocomplex (i.e., antigen-antibody complex) formation.

In addition to being designed to specifically binding and isolating tapeworm coproantigens in a mammalian sample, the device of the invention optionally may be designed to allow one or more other diagnostic tests to be performed. For example, the solid support may also include reagents for the detection of one or more helminthic worms such as roundworm, whipworm, heartworm and hookworm, one or more non-worm parasites, one or more viruses (such as parvovirus), one or more fungi, one or more protozoa (such as *Giardia*), or one or more bacteria. The reagents for the detection of one or more non-worm parasites, one or more viruses, one or more fungi, one or more protozoa, or one or more bacteria may be, for example, one or more antibodies or one or more antigens recognized by antibodies specific for one or more non-worm parasites, one or more viruses, one or more fungi, one or more protozoa, or one or more bacteria.

In one embodiment, the device of the present invention is a microtiter plate that includes a plurality of wells, wherein each well includes a solid support having one or more antibodies of the invention immobilized thereupon.

The microtiter plate may be used in conjunction with a method of the present invention to detecting the presence or absence of one or more helminthic coproantigens in a sample. For example, a tapeworm infection may be diagnosed in a mammal by detecting one or more tapeworm antigens with an antibody that is immobilized on the solid support. In one embodiment, the antigens that are detected are coproantigens. "Coproantigens" are any product or products of gastrointestinal parasites such as tapeworms that are present in a fecal sample from the host species (e.g., a dog or cat) and that can specifically bind to antibodies. Coproantigens therefore may be whole worm, worm eggs, worm fragments, or products secreted, excreted or shed from worm or a combination thereof.

In addition to the microtiter plate, there are a large number of other alternative approaches for performing multiple immunoassays in parallel (i.e., multiplex immunoassays) which are known in the art. Typically, multiplex immunoassays can be performed in a single vessel, in a composition or device where the components of the multiple immunoassays are in fluid communication. These technologies may be based on arrays, microarrays, and/or microbeads or microparticles. In arrays or microarrays, the capture reagents are typically spotted or otherwise deposited in discreet areas of a single device, such as a membrane. In bead-based approaches, capture reagents for each assay are attached to beads, where the beads of each assay are distinguishable from the beads of the other assays. The distinguishing may occur by color of light, physical position, barcode, or the like. See, for instance, Tighe, P. J., Ryder, R. R., Todd, I. and Fairclough, L. C. (2015), ELISA in the multiplex era: Potentials and pitfalls. Prot. Clin. Appl., 9: 406-422. doi: 10.1002/prca.201400130).

A multitude of such multiplexing platforms are commercially available. Examples include Luminex® (see, e.g., U.S. Pat. No. 7,523,637); πCode™ MicroDiscs (Plexbio, see, e.g., US Pat. Appl. No. US2014/0274778); Barcoded Magnetic Beads and methods and instruments for running assays therewith (e.g., Applied BioCode, Inc., Santa Fe Springs, Calif., USA; magnetic barcoded chips (e.g., Applied BioCode, Inc.; e.g., U.S. Pat. No. 8,232,092); microfluidic tests strips (e.g., LumiraDx®, U.S. Pat. No. 9,919,313); and planar light deck technologies such as LightDeck® (mBio®, U.S. Pat. No. 9,739,714). Additional multiplex immunoassay technologies include the MULTI-ARRAY (Meso Scale Diagnostics, Rockville, Md., USA), the Bio-Plex® Multiplex System (Bio-Rad, Hercules, Calif., USA), the Access 2 (Beckman Coulter, Atlanta, Ga.); and the ProcartaPlex® and ProQuantum® technologies (ThermoFisher Scientific, Waltham, Mass., USA) (see Fu Q, Zhu J, Van Eyk J E. *Comparison of multiplex immunoassay platforms*. Clin Chem. 2010 February; 56(2):314-8. doi: 10.1373/clinchem.2009.135087).

In another aspect of the invention, the device for detecting the presence or absence of one or more tapeworm coproantigens from a fecal sample comprises a solid support, one or more lectins and one or more antibodies selected from the group consisting of: (a) a first antibody capable of specifically binding a coproantigen from a first tapeworm species, but not a coproantigen from a second tapeworm species or a coproantigen from a third tapeworm species; (b) a second antibody capable of specifically binding the coproantigen from the second tapeworm species, but not the coproantigen from the first tapeworm or the coproantigen from the third tapeworm species; and (c) a third antibody capable of specifically binding the coproantigen from the third tapeworm species, but not the coproantigen from the first tapeworm species or the coproantigen from the second tapeworm species. In one embodiment, the solid support has immobilized thereon one or more antibodies, two or more antibodies, three or more antibodies, four or more antibodies, five or more antibodies, six or more antibodies, seven or more antibodies, or eight or more antibodies. The labeled lectin can bind to the carbohydrates on the tapeworm coproantigen captured by the immobilized antibodies for detection purposes. In another embodiment, the lectin can be immobilized on the solid support. The immobilized lectin can capture tapeworm coproantigen, if present, and the resulting complex can be detected by one or more labeled antibodies. In another embodiment, the device further comprises one or more species of tapeworm antigen, wherein the one or more species of tapeworm antigen are specifically bound to the antibodies.

The invention further includes assay kits (e.g., articles of manufacture) for detecting and distinguishing between different species of tapeworm in a mammalian sample. In some embodiments, the assay kits can further detect and distinguish co-infection with helminthic worms such roundworm, whipworm and/or hookworm in the mammalian sample. A kit therefore may include one or more devices and/or compositions of the present invention. For example, the kit may include anti-tapeworm antibodies and means for determining binding of the antibodies to tapeworm antigens and means for determining binding of the antibodies to tapeworm antigens. In one particular example, such a kit includes the device having an immobilized anti-tapeworm antibody to one or more different species of tapeworm, one or more antigen capture reagents (e.g., a non-immobilized labeled antigen capture reagent and an immobilized antigen capture reagent) and wash reagent, as well as detector reagent and positive and negative control reagents, if desired or appropriate. Other components such as buffers, controls, and the like, known to those of ordinary skill in art, may be included in such test kits. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

The present kit may further include instructions for carrying out one or more methods of the present invention, including instructions for using any device and/or composition of the present invention that is included with the kit.

B. Methods of the Invention

The present invention further includes methods for using one or more of the devices, kits and/or compositions of the present invention to detect the presence or absence of one or more tapeworm antigens in a sample. The methods therefore may be carried out to detect the presence or absence of one or more species of tapeworm in a sample, such as, for example, a fecal sample, that is obtained from a mammal, including, but not limited to, a canine, feline, porcine, bovine or human. Further, the methods may be carried out to detect one or more of helminthic worms such as roundworm, whipworm, hookworm and heartworm, non-worm parasites such as *Giardia*, and viruses such as parvovirus in the sample.

In the methods of the present invention, detection of one or more species of tapeworm, may be accomplished by detecting the presence or absence of one or more tapeworm antigens. When the sample under test for tapeworm coproantigens is feces, the soluble portion of the feces may be collected by any protocol known in art. For example, in addition to the specific protocol described in the Example section herein, the soluble portions of the sample generally may be collected by using filtration, extraction, centrifugation, or simple mixing followed by gravimetric settling. The skilled artisan will recognize that there are a variety of ways of extracting and preparing non-fecal samples from a mammal as well. For example, the sample may be a bodily fluid that is naturally excreted or otherwise released by the mammal or that is artificially obtained from the mammal. Such artificial extraction may be carried out by milking the mammal or by injecting a syringe into the mammal and drawing the fluid into the syringe. Once obtained, the fluid optionally may be fractionated (for example, serum may be fractionated from whole blood as then used as the sample). As another example, the sample may be obtained by swabbing the mammal, such as the oral cavity of the mammal, for example. As yet another example, tissue sections may be obtained by biopsy.

The methods include contacting the mammalian sample with one or more antibodies specific for tapeworm coproantigens under conditions that allow an antigen/antibody complex, i.e., an immunocomplex, to form. That is, an antibody specifically binds to a coproantigen present in the sample. The skilled artisan is familiar with assays and conditions that may be used to detect such antigen/antibody complex binding. For example, the antigen/antibody complex may be detected using a secondary antibody that binds to the antigen/antibody complex. The formation of a complex between antigen and antibodies in the sample may be detected using any suitable method known in the art.

Further, the relative amount of antibody-antigen complexes that are formed in one particular reaction may be measured with respect to those formed in any other reaction by any methodology known in the art for achieving that goal. When it is determined that a sample under test has a specific tapeworm antibody-antigen complexes, it can be concluded, based upon the specific complexes formed, that a specific tapeworm is present in the host mammal and which tapeworm is present (tapeworm species *Taenia pisiformis* and *Dipylidium caninum* for instance). When this is true, it may be concluded that the mammal from which the test sample was obtained harbors an intestinal tapeworm infection. The conclusions that the mammal being tested harbors an intestinal tapeworm infection may be made by a clinician at a diagnostic service provider or by a caregiver of the mammal, such as the mammal's veterinarian, for example. When a caregiver of a mammal determines (or is otherwise informed that) a mammal harbors a tapeworm infection and which tapeworm is present, the caregiver may then subject the mammal to a course of treatment that is optimally designed to rid the mammal of the tapeworm specifically, rather than of a parasitic worm infection generally. Further, the present invention can be used to confirm that any animal that has received treatment for the specific tapeworm infection has been rid of that infection. A caregiver who learns that a sample includes both tapeworm and roundworm, but not hookworm, for example, could use that knowledge to treat the mammal from which the sample was taken specifically for tapeworm by administering to that mammal a drug optimally effective against tapeworm and a second drug optimally effective against roundworm. Absent such knowledge, the caregiver may, for example, otherwise treat the mammal with a drug that is optimally effective against only tapeworm, only roundworm, or neither tapeworm nor roundworm (in such cases, the mammal would be at risk of receiving suboptimal treatment). In addition, humans who may come in contact with the infested animal or its excretions may be advised to take precautions against acquiring the parasite or parasites. In this context, it is important to determine the worm species with high specificity worms can cause significant disease (e.g., larval migrans) in humans.

A patient suffering from infections with intestinal parasites may be treated with certain therapeutics known to eliminate the parasites from the patient. Thus, a patient whose feces is found to contain coproantigen from an intestinal parasite may be treated with an appropriate therapeutic with the goal of reducing or eliminating the intestinal parasite.

Patients suffering from infections with intestinal parasitic worms such as tapeworms, hookworms, whipworms and/or roundworms can be treated with de-worming drugs, also known as anthelmintics (or anthelminthics). Such anthelmintics are widely known to those skilled in the art. Anthelmintics for the treatment of tapeworms include, without limitation praziquantel, nitazoxanide, albendazole, epsiprantel, fenbendazole, or combinations thereof. Anthelmintics may be administered by a variety of suitable routes, including orally, parenterally, such as subcutaneously, intravenously, intramuscularly or interperitoneally, or topically (cutaneously), such as directly on to exposed skin surface, to a patient in the treatment and/or prevention of intestinal parasites.

*Giardia* is a microscopic parasite that causes the diarrheal illness known as Giardiasis. *Giardia*, including *Giardia intestinalis, Giardia lamblia* and *Giardia duodenalis*, is found on surfaces or in soil, food, or water that has been contaminated with feces from infected humans or animals. *Giardia* coproantigen can be detected with a number of commercially available tests, including VetScan® Canine *Giardia* Rapid Test (Abaxis, Union City, USA), Anigen® Rapid CPV-CCV-*Giardia* Antigen Test (BioNote, Seoul, Korea), SNAP® *Giardia* Test (IDEXX, Westbrook, Me., USA) and *Giardia* Antigen by ELISA test (IDEXX), ProSpecT® *Giardia/Cryptosporidium* Microplate Assay (Thermo Fisher Scientific, Waltham, Mass., USA) and Witness® *Giardia* Test (Zoetis, Parsippany, N.J., USA) (Barbecho J M, Bowman D D, Liotta J L. Comparative performance of reference laboratory tests and in-clinic tests for *Giardia* in canine feces. *Parasit Vectors*. 2018 Aug. 1; 11(1):444 doi: 10.1186/s13071-018-2990-6. PMID: 30068364; PMCID: PMC6090814.)

Therapeutics for the treatment of *Giardia* infections are widely known to those skilled in the art. *Giardia* infections may be treated with a one or more of several drugs including fenbendazole, albendazole, metronidazole, tinidazole, nitazoxanide, paromomycin, quinacrine, and furazolidone, febantel, pyrantel pamoate, praziquantel or combinations thereof. These drugs may be administered by a variety of suitable routes, including orally, parenterally, such as subcutaneously, intravenously, intramuscularly or interperitoneally, or topically (cutaneously), such as directly on to exposed skin surface, to a patient in the treatment and/or prevention of *Giardia*.

Intermediate hosts may be involved in transmitting one or more worm or non-worm parasites, fungi, viruses and bacteria to the patient and thus a successful therapeutic intervention includes strategies to control or prevent reinfection. For instance, as tapeworm infections can be transmitted by intermediate hosts such as fleas and canine chewing lice, a successful therapeutic intervention in the case of tapeworm infection includes strategies to control any intermediate host (e.g., flea) infestation that may be present on the patient. Thus, controlling intermediate hosts such as fleas aids in preventing reinfection of the patient with tapeworm. Therapeutics for the treatment or control of flea infestation are well known to those skill in the art and include selamectin, fipronil, imidacloprid, indoxacarb, pyrethrin, permethrin, flumethrin, spinosad, nitenpyram, afoxolaner, fluralaner, saralane, nitenpyram, methoprene, pyriproxyfen, and lufenuron, or combinations thereof. Flea control agents may be administered by a variety of suitable routes including orally, parenterally, such as subcutaneously, intravenously, intramuscularly or interperitoneally, or topically (cutaneously), such as directly on to exposed skin surface, to a patient. Representative suitable flea control forms includes sprays, powders, collar, oral compositions, or topical treatments.

The steps of the method of the present invention may include applying a mammalian sample to a device of the invention, which includes a (a) first antibody capable of specifically binding coproantigen from a first tapeworm, but not coproantigen from a second tapeworm or coproantigen from a third tapeworm; (b) a second antibody capable of specifically binding the coproantigen from the second tapeworm, but not the coproantigen from the first tapeworm or the coproantigen from the third tapeworm; and (c) a third antibody capable of specifically binding the coproantigen from the third tapeworm, but not the coproantigen from the first tapeworm or the coproantigen from the second tapeworm to form antibody-coproantigen complexes in the presence of the coproantigens, if any, in the sample; and detecting the presence or absence of the antibody-coproantigen complexes, if any.

In some embodiments, the device can further include one or more antibodies selected from: an antibody capable of specifically binding a roundworm coproantigen, but not a whipworm or hookworm coproantigen; an antibody capable of specifically binding a whipworm coproantigen, but not a roundworm or hookworm coproantigen; an antibody capable of specifically binding a hookworm coproantigen, but not a whipworm or roundworm coproantigen; an antibody capable of specifically binding *Giardia* coproantigen, but not coproantigen selected from the group consisting of roundworm coproantigen, whipworm coproantigen, hookworm coproantigen, tapeworm *Taenia* coproantigen, tapeworm *Dipylidium* coproantigen, and parvovirus coproantigen; and an antibody capable of specifically binding parvovirus, but not coproantigen selected from the group consisting of roundworm coproantigen, whipworm coproantigen, hookworm coproantigen, tapeworm *Taenia* coproantigen, tapeworm *Dipylidium* coproantigen, and *Giardia* coproantigen. In embodiments, the hookworm is *Ancyclostoma*, the roundworm is *Toxocara* and the whipworm is *Trichuris*. In other embodiments, the hookworm is *Ancylostoma caninum* or *Ancylostoma tubaeforme*; the roundworm is *Toxocara canis* or *Toxocara cati*; the whipworm is *Trichuris vulpis* or *Trichuris felis*; the *Giardia* is *Giardia lamblia*; and the parvovirus is feline parvovirus or canine parvovirus.

In one embodiment, the step of detecting the presence or absence of the antibody-coproantigen complexes, if any, further includes the step of providing one or more lectins that binds to at least one of the complexes. The lectin can be detectably labeled or immobilized onto a solid support. Alternatively, the first, second and third antibodies can be detectably labeled or immobilized on a solid support. In one embodiment the first, second and third antibodies can be immobilized on a solid support and the lectin can be detectably labeled. In another embodiment, the first, second and third antibodies can be detectably labeled and the lectin can be immobilized on a solid support.

In another embodiment, the step of contacting the fecal sample from a mammal with one ore more antibodies further includes the step of contacting the fecal sample with one or more lectins. The lectin can be detectably labeled or immobilized onto a solid support. Alternatively, the first, second and third antibodies can be detectably labeled or immobilized on a solid support. In one embodiment, the first, second and third antibodies can be immobilized on a solid support and the lectin can be detectably labeled. In another embodiment, the first, second and third antibodies can be detectably labeled and the lectin can be immobilized on a solid support.

The antibodies and lectins may be directly or indirectly attached to a solid support or a substrate such as a microtiter well, antibody-immobilizing portion of a SNAP® device, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). All of these substrate materials may be used in suitable shapes, such as films, sheets, or plates, or they may be coated onto or bonded or laminated to appropriate inert carriers, such as paper, glass, plastic films, or fabrics. Suitable methods for immobilizing antibodies, peptides and lectins on solid phases include ionic, hydrophobic, covalent interactions and the like.

The methods of the present invention do not require the use of solid phases or substrates, however. The skilled artisan will recognize that there are a number of ways that the present method may be carried out to detect the presence or absence of roundworm without involving the use of solid phases or substrates. In just one example, immunoprecipitation methods that do not require the use of solid phases or substrates may be carried out.

In some embodiments of the invention, the antigen/antibody complex is detected when an indicator reagent, such as an enzyme conjugate, which is bound to the antibody, catalyzes a detectable reaction. Optionally, an indicator reagent including a signal generating compound may be applied to the antigen/antibody complex under conditions that allow formation of a detectable antigen/antibody/indicator complex. Optionally, the antibody may be labeled with an indicator reagent prior to the formation of an antigen/antibody complex.

The formation of an antigen/antibody complex or an antigen/antibody/indicator complex in some of the methods of the present invention specifically may be detected by, e.g., radiometric, enzymatic, chemiluminescent, colorimetric, turbidimetric, fluorometric, photometric, size-separation, surface plasmon resonance, or precipitation methods. Detection of an antigen/antibody complex also may be accomplished by the addition of a secondary antibody that is coupled to an indicator reagent including a signal generating compound. Indicator reagents including signal generating compounds (labels) associated with a polypeptide/antibody complex may be detected using the methods described above and may include chromogenic agents, catalysts such as enzyme conjugates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Methods of the invention include, but are not limited to those based on competition, direct reaction or sandwich-type assays, including, but not limited to ELISA, RIA, immunofluorescent assays (IFA), hemagglutination (HA), fluorescence polarization immunoassay (FPIA), and microtiter plate assays (i.e., any assay done in one or more wells of a microtiter plate). One assay of the invention includes a reversible flow chromatographic binding assay, which may be performed, for example, by using a SNAP® device. See U.S. Pat. No. 5,726,010.

In some embodiments, the method of the invention facilitates sandwich or competition-type specific binding assays. In a sandwich assay, antigen capture reagents are immobilized in a reactive zone. These antigen capture reagents may specifically bind to antigens in the sample being tested for tapeworm. Following binding of the antigen from the sample, the antigen capture reagent/antigen complex is detected by any suitable method. For example, the complex may be reacted with labeled specific binding reagents (e.g., an enzyme-antibody conjugate) and antigen detected (e.g., upon reaction with substrate).

In other embodiments of the method of the present invention, a competition assay is performed. In a competition assay, antigen capture reagents are immobilized at the reactive zone and are contacted simultaneously with antigen from a sample and labeled antigen (e.g., an antigen-enzyme conjugate). The amount of label detected at the reactive zone is inversely proportional to the amount of antigen in the sample.

In some embodiments of the method, antibodies specific for tapeworm coproantigens are attached to a solid phase or substrate. A sample potentially including an antigen from tapeworm is added to the substrate. Antibodies that specifically bind tapeworm antigens are added. The antibodies may be the same antibodies used on the solid phase or they may be from a different source or species. Further, these antibodies may be linked to an indicator reagent, such as an enzyme conjugate. Wash steps may be performed prior to each addition. A chromophore or enzyme substrate may be added and color may be allowed to develop. The color reaction may be stopped and the color may be quantified using, for example, a spectrophotometer, and/or the color may be subjectively assessed by the human eye.

In other embodiments of the method, antibodies specific for tapeworm coproantigens are attached to a solid phase or substrate. A sample potentially including a tapeworm antigen is added to the substrate. Second anti-species antibodies that specifically bind the coproantigens are added. These second antibodies are from a different species than are the solid phase antibodies. Third anti-species antibodies that specifically bind the second antibodies and that do not specifically bind the solid phase antibodies are added. The third antibodies may include an indicator reagent, such as an enzyme conjugate. Wash steps may be performed prior to each addition. A chromophore or enzyme substrate may be added and color may be allowed to develop. The color reaction may be stopped and the color may be quantified using, for example, a spectrophotometer, and/or the color may be subjectively assessed by the human eye.

In a specific example, the method of the present invention is performed in conjunction with a device that is a lateral flow assay device by adding a prepared mammalian sample to a flow matrix of the device at a first region (a sample application zone). The prepared sample is carried in a fluid flow path by capillary action to a second region of the flow matrix where a particulate label capable of binding and forming a first complex with an antigen in the sample exists. The particulate label can be, e.g., a colored latex particle, dye sol, or gold sol conjugated to an antibody specific for a roundworm antigen. The first complex is carried to a third region of the flow matrix where an antibody that specifically binds a roundworm antigen is immobilized at a distinct location. A second complex is formed between the immobilized antibody and the first complex. The particulate label that is part of the second complex can be directly visualized by the human eye.

Each specific worm antibody may be an immobilized antigen capture reagent in a reaction zone (solid phase). A second antigen capture reagent, i.e., a second specific tapeworm antibody that has been conjugated to a label, either may be added to the sample before the sample is added to the device, or the second antigen capture reagent can be incorporated into the device. For example, the labeled antigen capture reagent may be deposited and dried on a fluid flow path that provides fluid communication between a sample application zone and the solid phase. Contact of the labeled antigen capture reagent with the test sample can result in dissolution of the labeled antigen capture reagent.

In one embodiment of the method of the present invention, specific worm coproantigen is detected by ELISA. Specific examples of the ELISA method of the present invention is described in the Example section included herein. Although the present invention is described with respect to those specific ELISA methods, however, it is to be understood that those of ordinary skill in the art will recognize that alternative, additional or substitute ELISA steps may be used without deviating from the basic goal achieved through this method of the invention.

In another embodiment of the present invention, tapeworm coproantigen is detected by using a lateral flow device, such as a SNAP® device, for example.

Further, the methods of the invention for detection of tapeworm infection can be combined with other diagnostic assays to detect the presence of other organisms or conditions. For example, assays of the invention can be combined with reagents that detect one or more helminthic worms, non-worm fecal parasites, one or more viruses, one or more fungi, one or more protozoa, one or more bacteria, one or more blood-borne parasites or occult blood or a combination thereof. By providing two or more unique binding sites in a single assay device (such as, for example, two unique spots on a SNAP® assay device), the present invention allows for detection of two or more organisms from a single sample. In one embodiment, there are three unique spots for detection of past or present infection or infestation from three organisms (the spots being either antigen or antibody binding reagents) from a single sample (i.e., the same individual sample is exposed to the three capture reagents on a single device). In yet another embodiment, there are four unique spots for detection of past or present infection or infestation from four organisms (the spots being either antigen or antibody binding reagents) from a single sample (i.e., the same individual sample is exposed to the four capture reagents on a single device. It is to be understood, however, that the same device may include more than four unique spots and/or allow for the detection of more than four organisms.

The reagents for the detection of one or more helminthic worms, non-worm parasites, one or more viruses, one or more fungi, one or more protozoa, or one or more bacteria may be, for example, one or more antibodies or one or more antigens recognized by antibodies specific for one or more helminthic worms, non-worm parasites, one or more viruses, one of more fungi, or one or more bacteria. In some embodiments, the reagents can include one or more antibodies or one or more antigens recognized by antibodies specific for one or more helminthic worm parasites (e.g., roundworm, whipworm, hookworm, and heartworm), non-worm parasites, one or more viruses (e.g., parvovirus such as canine parvovirus or feline parvovirus), one or more fungi, one or more protozoa (e.g., *Giardia* such as *Giardia lamblia*) or one or more bacteria.

The method further may optionally include using one or more nucleic acids from tapeworm, including, but not limited to, the nucleic acids of the present invention, to determine the presence or absence of one or more tapeworm species in a mammalian sample. Such use of these nucleic acids for determining the presence of the helminth may be carried out before, after or concomitantly with the carrying out of any other aspects of the method, including the detection of one or more tapeworm species by antibody. Therefore, in one aspect, after one or more tapeworm species is detected or not detected in a particular sample and the mammal from which the sample was obtained is diagnosed as either having or not having a tapeworm infection, the sample (or a later-obtained sample from the diagnosed mammal) may be tested for the presence or absence of any one or more of the nucleic acids, including any one or more nucleic acids of the invention. Anyone failing to detect a specific helminth in a particular mammal by using one or more nucleic acids (after the helminth had been detected by using one or more antibodies) would need to take into consideration the possibility that the antibodies had detected helminthic coproantigen prior to the appearance of detectable helminthic nucleic acid in the sample. In such an instance, the mammal's caregiver may elect to ignore the observation that the nucleic acid had failed to detect the helminth and proceed with treating the mammal specifically for helminth infection based on the observation that the antibodies had in fact detected helminth. In another aspect, the nucleic acids are used to determine the presence or absence of helminths in a particular mammal, and then the presence or absence of helminths is further evaluated by using the antibodies of the present invention. Detection of one or more helminthic nucleic acids may be carried out by using any nucleic acid detection techniques known to the skilled artisan. For example, such detection may be carried out by performing a PCR-based technique, such as, but not limited to, for example, a real-time PCR-based technique. Exemplary PCR-based techniques are described in, e.g., *PCR Protocols* (*Methods in Molecular Biology*), 2$^{nd}$ ed., Bartlett and Stirling, eds., Humana Press (2003); and Sambrook and Russell, *Molecular Cloning: A Laboratory Manual*, Cold Spring Harbor Laboratory Press (2001); each one of which is incorporated herein by reference in its entirety.

The present invention is specifically described with reference to the following Examples; however, it is not to be construed as being limited thereto.

Example A

Unless otherwise indicated, the following materials and techniques were used to generate data described in one or more of Examples 1-5 as described below.

Preparation of Worm Extracts of *Taenia pisiformis* and *Dipylidium caninum*.

*Taenia pisiformis* and *Dipylidium caninum* worm extracts were purchased from Antibody systems, Inc. Hurst, Tex., U.S.A. The worm extracts were centrifuged at 10,000 g for 30 minutes at 4° C. Supernatant were collected, dialyzed into PBS, pH 7.0 (membrane molecular weight cutoff 12-14 kD, Part 132678, Spectrum, Repligen, Waltham Mass., USA) and protein concentration were determined with Bradford assay.

Preparation of Worm Extracts of *Taenia taeniaeformis*.

*Taenia taeniaeformis* were obtained from Ross University School of Veterinary Medicine, Saint Kitts. The whole worms were washed several times with cold PBS, pH 7.0, to remove any fecal materials and mucus from the hosts in room temperature and homogenized at 4° C. with a tissue grinder until no obvious tissue chunks were visible to the naked eye. The homogenized materials were transferred to a 50 ml Falcon tube and the grinder was rinsed 2-3 times with cold PBS, pH 7.0. The homogenized tapeworm, together with the rinses of the grinder, were centrifuged at 10,000 g for 30 min at 4° C. and the supernatants were collected before dialyzed into PBS, pH 7.0 (membrane molecular weight cutoff 12-14 kD, Part 132678, Spectrum, Repligen, Waltham Mass., USA). Protein concentration was determined with Bradford assay.

Preparation of *Dipylidium caninum* TCA Soluble Fraction.

This antigen was prepared by disrupting worms in an aqueous buffer solution (phosphate buffer, pH, 7.2), centrifuging to remove insoluble and particulate components, adding of 30% trichloroacetic acid (TCA) dropwise to a final concentration of 15%, stirring for another 15 min at 18-27° C. after all the TCA added, sitting on the bench for another 45 minutes undisturbed at 18-27° C., centrifuging to remove insoluble components, dialyzing against an aqueous buffer solution (0.01 M phosphate buffer, pH 7.2) with Spectrapor I dialysis tube, MWCO: 6-8 K, and lyophilizing with a lyophilizer.

Preparation of Worm Wash.

Frozen raw worm specimen were rinsed 4 times in PBS buffer at pH7.2. The buffer solutions from the first 3 rinse steps were discarded. The buffer solution from the fourth rinse step was centrifuged at 10,000 g for 20 minutes, and the supernatant was collected. The supernatant was concentrated using an iCON Concentrator (MWCO: 20 mL/9K; Thermo Scientific). The resulting concentrate was termed "Worm Wash" (WW).

Preparation of E/S Material.

The Excreted/Secreted (E/S) materials were collected by keeping the tapeworms alive in a T-150 flask with tissue culture medium (EMEM with D-glucose, Gentamicin and Fungizone, pH 7.2-7.3) in a 37° C. incubator with 5% CO2 for two weeks. Briefly, living tapeworms were washed several times with warmed medium to remove any fecal residues, placed in a T-150 Tissue culture flask with 100 ml warmed medium (EMEM). The viability of the tapeworms was verified daily and the medium was changed three times a day. The used media were pooled and concentrated with an Icon Concentrator (MWCO: 9 K; Thermo Scientific), and the resulting concentrated E/S material was used for antibody production.

Polyclonal Antibody (pAb) Preparation.

Polyclonal antibodies were raised with Specific Pathogen Free (SPF) rabbits at SDIX, LLC (Windham, Me., U.S.A.). The immunogens were whole worm extracts (*Dipylidium caninum* and *Taenia pisiformis* from Antibody Systems Inc., Hurst, Tex.; *T. taeniaeformis* from IDEXX Laboratories, Inc.) or E/S material (IDEXX Laboratories, Westbrook, Me.). Briefly, rabbits were challenged subcutaneously with the same immunogen in different adjuvants four times over a period of 50 days. Serum was collected at the end of the immunization procedure.

Monoclonal Antibody (mAb) Preparation.

Murine monoclonal antibodies were produced according to standard procedures unless otherwise noted. Briefly, 3-5 Balb/c mice were immunized with the immunogen, and spleen cells harvested after completion of the immunization schedule. Spleen cells were fused with myeloma cells. Through several rounds of screening, and selecting with HAT medium, isotyping and subcloning, specific hybridoma cell lines secreting the desired mAb secreted were obtained.

Antibody Purification and Isolation.

Both rabbit polyclonal antibody and murine monoclonal antibody were purified with Protein G Sepharose 4 Fast Flow (Thermo Fisher Scientific) affinity chromatography using AKTA purification system. Briefly, rabbit serum or TCF (terminal culture fluid) were diluted with the washing buffer, loaded on to the Protein G column. The column was washed with washing buffer thoroughly before the antibody being eluted from the column. The eluted antibody was neutralized with 1 M Tris buffer, pH 8.0, then dialyzed into 10 mM PBS, pH 7.2, and stored in −20° C. for future usage.

Fecal Extract Preparation.

Samples from fresh, unpreserved canine or feline fecal samples (1 gram) were suspended in 4 ml of diluent solution ("diluent solution" is 0.05 M Tris base; 1 mM EDTA; 0.45% Kathon; 16 mg/ml gentamicin sulfate; 0.05% Tween-20; 40% fetal bovine serum; 10% rabbit serum; and 5% mouse serum). The suspension was centrifuged at 4000 rpm for 20 minutes to produce a first supernatant. The first supernatant was centrifuged at 10000 g for 10 minutes to produce a second supernatant, which is referred to herein as "fecal extract."

ELISA Assays.

Purified polyclonal Ab or monoclonal Ab (100 μl/well and 3 μg/ml) was immobilized by physical adsorption on Immulon 1B 96-well plates overnight at 4° C. The plates were then blocked with 1% BSA in 0.1M Tris pH 7.0 at 4° C. overnight, followed by drying at room temperature. Approximately 100 μl of fecal extract was added to each well and allowed to incubate at room temperature for one hour. The wells were then washed five times with a PBS-Tween-20 solution according to standard methods known to those of ordinary skill in the art. In a separate reaction vessel, free rabbit pAb (a different antibody, in case of mAb, against the same target was used) was labeled with horseradish peroxidase (HRP) by using the crosslinker succinimidyl 4-[N-maleimidomethyl]cyclohexane-1-carboxylate (SMCC) to create a conjugate, and 3 µg/ml of this conjugate was added to each well having immobilized pAb or mAb. Following a 30-minute incubation period at room temperature, unbound conjugate was washed from the wells by using PBS-Tween-20 solution according to standard methods known to those of ordinary skill in the art. 50 µl of TMBLUE™ peroxidase substrate (IDEXX Laboratories, Westbrook, Me.) was then added to each well and the plates were incubated for 10 minutes at room temperature. After stopping each enzymatic reaction with 0.1% sodium dodecyl sulfate (SDS) following the 10-minute incubation period, the optical density (OD) value of each well of the 96-well plate was measured at A650 by standard spectrophotometric techniques by using an ELISA plate reader to generate an "OD650 value" (or, more simply, an "OD value") for each well. In this arrangement, the OD value obtained for any particular well of the 96-well plate was directly proportional to the amount of specifically bound antigen present in the well. OD values of 0.1 or below were regarded as negative results, and OD values were regarded as positive results unless otherwise noted in the Examples.

Carbohydrate/Glycosylation Characterization Using Carbohydrate-Proving ELISA with Jacalin-Biotin.

Murine IgM mAb ADX226 coated immulon 1B plate was used for the carbohydrate-proving ELISA. Approximately 100 µl of fecal extract was added to each well and allowed to incubate at room temperature for one hour. The wells were then washed five times with a PBS-Tween-20 solution according to standard methods known to those of ordinary skill in the art. Jacalin-Biotin (0.25 ug/ml) was added to each well, followed by one-hour incubation at room temperature. Unbound Jacalin-biotin (Vector Laboratories, 30 Ingold Road, Burlingame, Calif.) was washed from the wells by using PBS-Tween-20 solution according to standard methods known to those of ordinary skill in the art. Streptavidin-HRP conjugate (Vector Laboratories, 30 Ingold Road, Burlingame, Calif.) was added to each well and incubate at room temperature for 30 minutes. Unbound Streptavidin-HRP conjugate was washed away again by using PBS-Tween 20 solution. 50 µl of TMBLUE™ peroxidase substrate (IDEXX Laboratories Inc., Westbrook, Me.) was then added to each well following the 30 min with Streptavidin-HRP conjugate and the plates were incubated for 1 minute at room temperature. After stopping each enzymatic reaction with 0.1% sodium dodecyl sulfate (SDS) following the 1-minute incubation period, the optical density (OD) value of each well of the 96-well plate was measured at A650 as illustrated above in fecal assay ELISA section.

Example 1A

Raising and Screening of Murine Monoclonal Antibodies Against *Taenia pisiformis*.

Murine mAbs (monoclonal antibodies) were raised by immunization of mice with worm extract (WE) of *T. pisiformis* (hereinafter, *T. pisiformis* extract or extract of *T. pisiformis*), and hybridomas were raised. Candidate hybridomas were screened for the ability of secreted mAbs to bind the immunogen (i.e., extract of *T. pisiformis*) coated onto microtiter plates in a ELISA capture assay. From this screen, one hundred (100) hybridomas (i.e., 100 mAbs) that were positive in this screen (i.e. able to bind the *T. pisiformis* extract) were chosen for further analysis. The 100 candidate mAbs were further screened for their ability to function in a coproantigen ELISA assay, by a capture assay screen. Microtiter plates were coated with a rabbit polyclonal antibody that had been raised by standard immunization of rabbits with *T. pisiformis* extract. FEX (fecal extract) made from canine fecal samples was added. The fecal samples were from dogs known to be *T. pisiformis* infected and received from IDEXX Reference Laboratories. One of the 100 candidate mAbs supernatant was added to each well, followed by goat a-mouse IgG conjugated to a label. Five mAbs (02D09, 03H02, 07C02, ADX131 and ADX13) performed particularly well in this assay and were chosen for further analysis.

The five mAbs were further screened for their ability to function when paired with each other in a sandwich assay. For this purpose, each of the five mAbs was coated onto the wells of microtiter plates and incubated with FEX (*Taenia pisiformis* positive samples: n=10; *T. pisiformis* negative samples: n=10), followed by one of the five mAbs conjugated to a label, or a *Taenia pisiformis* WE mouse pAb. Five mAbs performed well in combination with at least one of the other mAbs, and were therefore chosen for further study. From the five mAbs that performed well, two (ADX131 and ADX132) were chosen for further testing because they resulted the in low background and high signal when paired with each other in the coproantigen ELISA.

Figure 2:
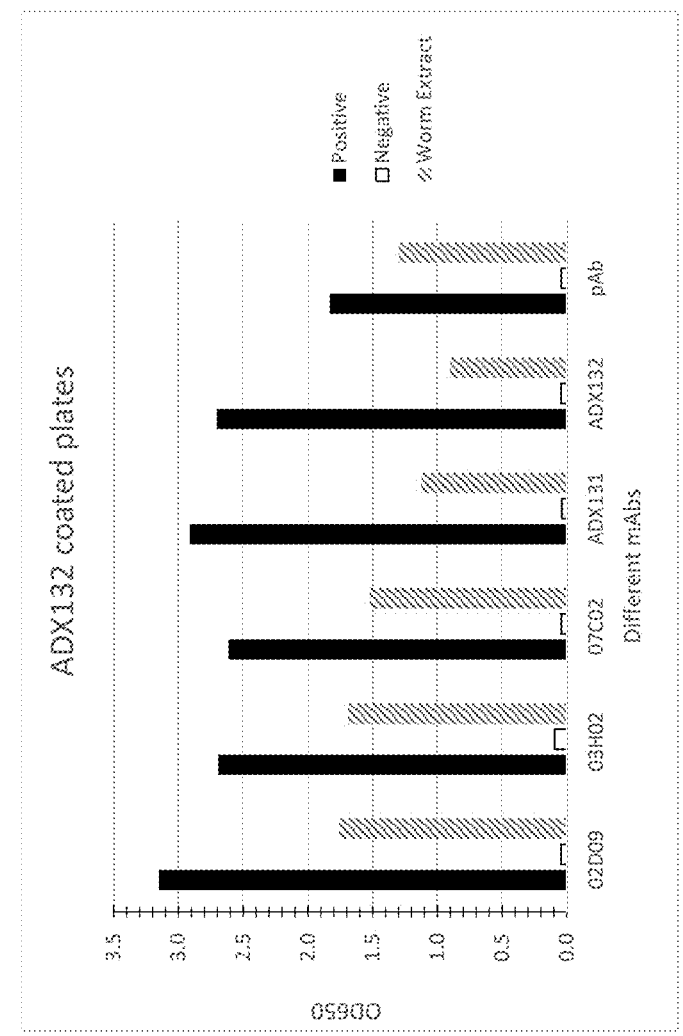
FIG. 2 shows the OD determinations of antibody ADX132 against worm extract and fecal extract from canines that are negative or positive for tapeworm infection by following the method of the present invention as shown in Example 1A. Positive=Fecal extract (FEX) from *T. pisiformis* infected dog; Negative=FEX from dog not infected with *T. pisiformis*; Worm Extract=*T. pisiformis* worm extract (WE).

ADX131 and ADX132 were each paired with HRP conjugates of 02D09, 03H02, 07C02, ADX131 and ADX132 in another ELISA essay. An additional pairing with *T. pisiformis* WE rabbit pAb was used as a positive control. ADX131 and ADX132 were individually coated onto the wells of microtiter plates; incubated with FEX from a *T. pisiformis* infected dog, a *T pisiformis* uninfected dog, or *T. pisiformis* worm extract; followed by the conjugates and the HRP substrate. In each of the five antibody pairings, ADX131 resulted in strong signal with the FEX from infected dog and with the worm extract. In four out of the five antibody pairings, ADX131 resulted in a negative result (i.e., signal below threshold) with the FEX from uninfected dog, except that the pairing with 03H02 resulted in a signal that was slightly above the chosen threshold of 0.1 OD (FIG. 1). In all five antibody pairings, ADX132 resulted in strong signal with the FEX from infected dog and with the worm extract. In all five antibody pairings, ADX132 resulted in low background signal with the FEX from uninfected dog (FIG. 2).

Example 1B

*Taenia pisiformis* Coproantigen ELISA Specificity and Sensitivity Evaluation.

Figure 3:
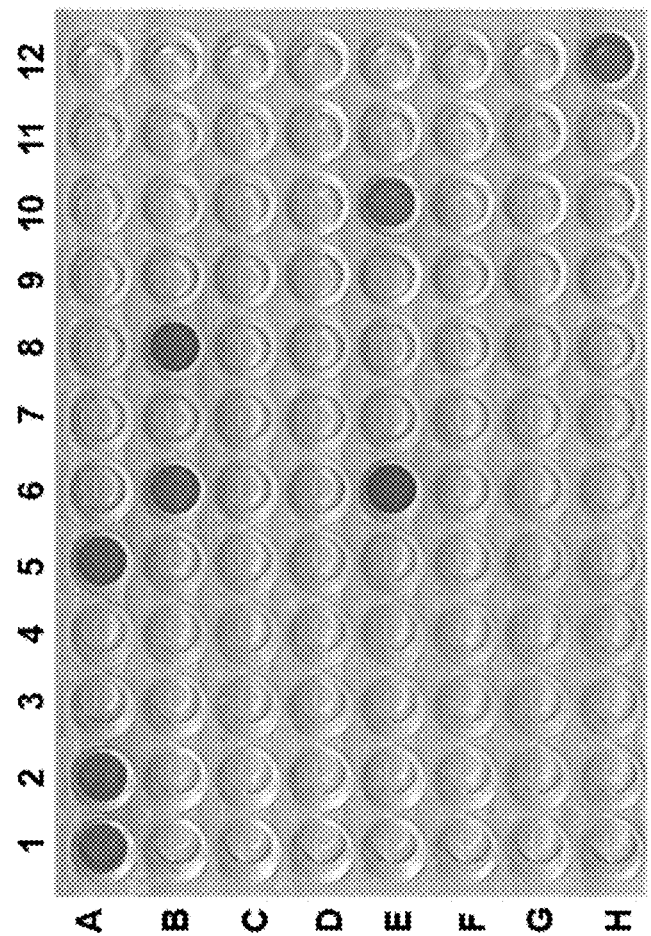
FIG. 3 shows a microtiter plate in which an ELISA assay was carried out using fecal extracts of canines infected with tapeworm by following the method of the present invention as shown in Example 1B. H11 is a negative control. A5, B6, B8, E6 and E10 are fecal extracts from five *T. pisiformis* positive dogs. Each of the other wells has a fecal extract from one of the hookworm *Ancylostoma caninum* infected dogs, or the roundworm *Toxocara canis* infected dogs, or the whipworm *Trichuris vulpis* infected dogs, or the *D. caninum* infected dogs.
Figure 4:
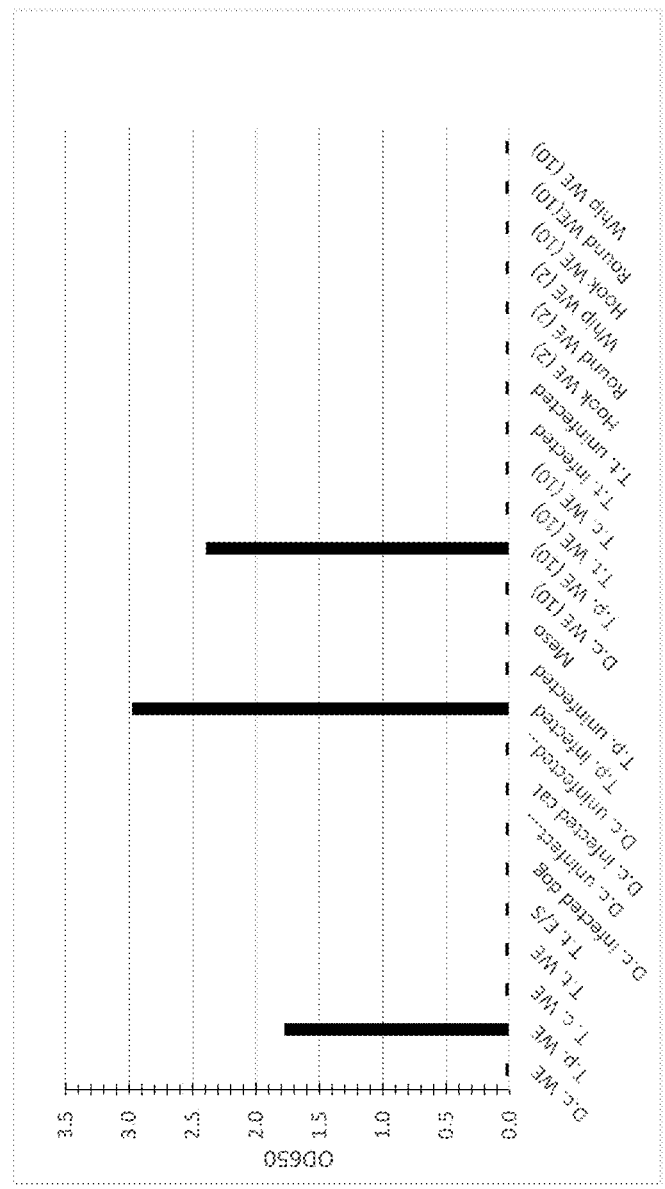
FIG. 4 shows the specificity of a sandwich coproantigen ELISA assay using antibody ADX131 coated onto a microtiter plate, and ADX132-HRP conjugate applied after addition of the patient sample. The assay was run on *D. caninum* WE, *T. pisiformis* WE, *T. crassiceps* WE, *T. taeniaeformis* WE, *T. taeniaeformis* E/S, as well as the FEX from a *D. caninum* positive dog, a *D. caninum* negative dog, a *D. caninum* positive cat, a *D. caninum* negative cat, a *T. pisiformis* positive dog, a *T. pisiformis* negative dog, a pool of three *T. taeniaeformis* positive felines, a pool of three *T. taeniaeformis* negative felines, hookworm *Ancylostoma caninum* WE, roundworm *Toxocara canis* WE, and whipworm *Trichuris vulpis* WE as discussed in Example 1B.

To assess the specificity of the assay, the *T. pisiformis* coproantigen ELISA assay (using ADX131 coated on plate and ADX132-HRP conjugate) was tested against FEX from canines infected with Hookworm *Ancylostoma caninum* (n=44), roundworm *Toxocara canis* (n=9), whipworm *Trichuris vulpis* (n=36), *D. caninum* (n=44), or *Taenia pisiformis* (n=5). The result (see FIG. 3) showed that all 5 *T. pisiformis* samples were positive in the assay and all of the others were negative. The *T. pisiformis* coproantigen ELISA did not cross-react with hookworm *Ancylostoma caninum*, roundworm *Toxocara canis*, whipworm *Trichuris vulpis*, or *D. caninum*. Thus, the *T. pisiformis* coproantigen ELISA assay was 100% sensitive and specific in this experiment. To assess the specificity of the assay, a sandwich coproantigen ELISA was built with ADX131 coated onto a microtiter plate, and ADX132-HRP conjugate applied after addition of the patient sample. The assay was run on *D. caninum* WE, *T. pisiformis* WE, *T. crassiceps* WE, *T. taeniaeformis* WE, *T. taeniaeformis* E/S, as well as the FEX from a *D. caninum* positive dog, a *D. caninum* negative dog, a *D. caninum* positive cat, a *D. caninum* negative cat, a *T. pisiformis* positive dog, a *T. pisiformis* negative dog, a pool of three *T. taeniaeformis* positive felines, and a pool of three *T. taeniaeformis* negative felines. The beforementioned WEs were used at a concentration of 1 µg/ml protein. The assay was additionally run on several WE samples at 2 µg/ml protein and/or 10 µg/ml protein. The WE samples run at these higher concentrations were *D. caninum* WE, *T. pisiformis* WE, *T. taeniaeformis* WE, *T. crassiceps* WE, hookworm *Ancylostoma caninum* WE, roundworm *Toxocara canis* WE, and whipworm *Trichuris vulpis* WE. Among these samples, the assay was positive only on *T. pisiformis* WE and the *T. pisiformis* positive dog (FIG. 4). Thus, the ADX131/ADX132-HRP ELISA was highly specific in this experiment.

To assess the specificity of the *T. pisiformis* coproantigen ELISA assay (using ADX131 coated on plate and ADX132-HRP conjugate), the assay was run on FEX from 822 canine samples. Of these samples, 1 sample had been confirmed as *T. pisiformis* positive by microscopy (i.e., proglottids were observed by microscopy), and 821 had been confirmed as *T. pisiformis* negative by microscopy. The results showed that of the 821 microscopy-negative samples, 818 were negative in the *T. pisiformis* coproantigen ELISA assay, and 3 were positive. The microscopy-positive sample was positive in the *T. pisiformis* coproantigen ELISA assay. Thus, the *T. pisiformis* coproantigen ELISA assay was 99.7% specific in this experiment.

Example 1C

Antigen Characterization: Glycosylation of the Antigens Bound by Anti-*T. pisiformis* mAb ADX131.

In order to determine whether the coproantigen bound by mAb ADX131 is glycosylated, the ability of 21 different lectins were tested for their ability to bind the coproantigen using a commercial kit (Biotinylated lectin kits I, II and III from Vector Laboratories, Burlingame, Calif.). The assays were carried out according to the manufacturer's instructions. Briefly, FEX from *T. pisiformis* positive canines was added to plates coated with ADX131. After washing, the lectin::biotin conjugates were added, followed by streptavidin-HRP and the color substrate. In this test, the following lectins resulted in high signal and low background, indicating that they bound to *T. pisiformis* coproantigen: WGA, succinylated WGA, PSA, GSLII and LCA.

Antigen Characterization: Glycosylation of the Antigens Bound by Anti-*T. pisiformis* mAb ADX132.

In order to determine whether the coproantigen bound by mAb ADX132 is glycosylated, the ability of ADX132 to bind FEX substances bound by 21 different lectins was tested using a commercial kit (Biotinylated lectin kits I, II and III from Vector Laboratories, Burlingame, Calif.). The assays were carried out according to the manufacturer's instructions. Briefly, wells microtiter plates were coated with one of lectins, and FEX from *T. pisiformis* positive canines was added, followed by ADX132-HRP conjugate and the color substrate. In this test, the following lectins bound to coproantigen: WGA, UEA and GSLII.

The lectin binding data indicates that the *T. pisiformis* coproantigen bound by the ADX131/ADX132 assay is glycosylated. The lectin binding data further indicates that the ADX131/132 coproantigen contains the following moieties: non-reduced GlcNac; reduced GlcNac; fucose; GSL II; and mannose.

Example 2A

Preparation of Rabbit Polyclonal Antibodies Against *T. taeniaeformis*.

Worm extracts (WE), E/S material and worm wash (WW) of *T. taeniaeformis* were prepared as described above. Rabbits were immunized with *T. taeniaeformis* WE, *T. taeniaeformis* E/S, or *T. taeniaeformis* WW as described above to raise the polyclonal antibodies *T. taeniaeformis* WE rabbit pAb, *T taeniaeformis* E/S rabbit pAb and *T. taeniaeformis* WW rabbit pAb.

A. Initial Assessment of *T. taeniaeformis* WE Rabbit pAb-Rabbit pAb ELISA Assay, and *T. taeniaeformis* E/S Rabbit pAb-Rabbit pAb ELISA Assay.

For an initial assessment of the performance of coproantigen ELISA assays with *T. taeniaeformis* WE rabbit pAb, and *T. taeniaeformis* E/S rabbit pAb, feline fecal extracts from seven *T. taeniaeformis* positive and six *T. taeniaeformis* negative cats were tested.

*T. taeniaeformis* WE Rabbit pAb-Rabbit pAb ELISA Assay:

In this ELISA assay, *T. taeniaeformis* WE rabbit pAb was coated onto plates, contacted with FEX, then contacted with *T. taeniaeformis* WE rabbit pAb-HRP conjugate, then contacted with a color substrate. In this assay, all seven *T. taeniaeformis* positive samples were positive, while all six *T. taeniaeformis* negative samples tested negative. Therefore, sensitivity and specificity for the *T. taeniaeformis* WE rabbit pAb-rabbit pAb ELISA assay were 100% in this experiment.

*T. taeniaeformis* E/S Rabbit pAb-Rabbit pAb ELISA Assay:

In this ELISA assay, *T. taeniaeformis* E/S rabbit pAb was coated onto plates, contacted with FEX, then contacted with *T. taeniaeformis* E/S rabbit pAb-conjugate, then contacted with a color substrate. In this assay, all seven *T. taeniaeformis* positive samples were positive, while all six *T. taeniaeformis* negative samples tested negative. Therefore, sensitivity and specificity for the *T. taeniaeformis* E/S rabbit pAb-rabbit pAb ELISA assay were 100% in this experiment.

B. Performance of *T. taeniaeformis* WE Rabbit pAb-Rabbit pAb ELISA Assay on Canine and Feline Fecal Samples The performance of coproantigen ELISA assay with *T. taeniaeformis* WE rabbit pAb (as described under Section A) was further assessed on canine and feline fecal extracts. The canine sample set included fecal extracts from 31 *T. taeniaeformis* positive canines and 74 *T taeniaeformis* negative canines. The feline sample set included fecal extracts from 13 *T. taeniaeformis* positive felines and 39 *T. taeniaeformis* negative felines.

For canines, among the 31 positive samples, the *T. taeniaeformis* WE rabbit pAb-rabbit pAb ELISA assay yielded positive signal in 8 samples. Among the 74 negative canine samples, the *T. taeniaeformis* WE rabbit pAb-rabbit pAb ELISA assay yielded positive signal in 6 samples. Therefore, the sensitivity was 25.8% and the specificity was 91.9% in this experiment.

For felines, among the 13 positive samples, the *T. taeniaeformis* WE rabbit pAb-rabbit pAb ELISA assay yielded positive signal in 12 samples. Among the 39 negative samples, the *T. taeniaeformis* WE rabbit pAb-rabbit pAb ELISA assay yielded positive signal in 4 samples. Therefore, the sensitivity was 92.3% and the specificity was 89.7% in this experiment.

C. Performance of *T. taeniaeformis* E/S Rabbit pAb-Rabbit pAb ELISA Assay on Canine and Feline Fecal Extracts.

The performance of coproantigen ELISA assay with *T. taeniaeformis* E/S rabbit pAb (as described under Section A) was further assessed on canine and feline fecal extracts. The canine sample set included fecal extracts from 31 *T. taeniaeformis* positive canines and 74 *T. taeniaeformis* negative canines. The feline sample set included fecal extracts from 13 *T. taeniaeformis* positive felines and 39 *T. taeniaeformis* negative felines.

For canines, among the 31 positive samples, the *T. taeniaeformis* E/S rabbit pAb-rabbit pAb ELISA assay yielded positive signal in 4 samples. Among the 74 negative canine samples, the *T. taeniaeformis* E/S rabbit pAb-rabbit pAb ELISA assay yielded positive signal in 1 sample. Therefore, the sensitivity was 12.9% and the specificity was 98.6% in this experiment.

For felines, among the 13 positive samples, the *T. taeniaeformis* E/S rabbit pAb-rabbit pAb ELISA assay yielded positive signal in 12 samples. Among the 39 negative samples, the *T. taeniaeformis* E/S rabbit pAb-rabbit pAb ELISA assay yielded positive signal in 3 samples. Therefore, the sensitivity was 92.3% and the specificity was 92.3% in this experiment.

D. Performance of *T. taeniaeformis* WW Rabbit pAb-Rabbit pAb ELISA Assay on Canine and Feline Fecal Samples The performance of coproantigen ELISA assay with *T. taeniaeformis* WW rabbit pAb was assessed on canine and feline fecal extracts. The canine sample set included fecal extracts from 31 *T. taeniaeformis* positive canines and 74 *T. taeniaeformis* negative canines. The feline sample set included fecal extracts from 13 *T. taeniaeformis* positive felines and 39 *T. taeniaeformis* negative felines.

For canines, among the 31 positive samples, the *T. taeniaeformis* WW rabbit pAb-rabbit pAb ELISA assay yielded a positive signal in 16 samples. Among the 74 negative canine samples, the *T. taeniaeformis* WE rabbit pAb-rabbit pAb ELISA assay yielded positive signal in 3 samples. Therefore, the sensitivity was 51.6% and the specificity was 98.6% in this experiment.

For felines, among the 13 positive samples, the *T. taeniaeformis* WW rabbit pAb-rabbit pAb ELISA assay yielded a positive signal in 12 samples. Among the 39 negative samples, the *T. taeniaeformis* WW rabbit pAb-rabbit pAb ELISA assay yielded positive signal in 3 samples. Therefore, the sensitivity was 92.3% and the specificity was 95.9% in this experiment.

Example 2B

Preparation of Mouse Polyclonal and Monoclonal Antibodies Against *T. taeniaeformis* WE and *T. taeniaeformis* E/S.

Worm extract (WE) of *T. taeniaeformis* and E/S material of *T. taeniaeformis* was prepared as described above. Mice were immunized with *T. taeniaeformis* WE or *T. taeniaeformis* E/S as described above to raise the mouse polyclonal antibodies *T. taeniaeformis* WE mouse pAb and *T. taeniaeformis* E/S mouse pAb. These polyclonal antibodies specifically their respective immunogens when the immunogens were coated onto microtiter plates.

A. Preparation of *T. taeniaeformis* WE Mouse mAb

Hybridomas were derived from the mice immunized with *T. taeniaeformis* WE as described above. From the resulting mouse monoclonal antibody (mouse mAb) secreting hybridomas, two *T. taeniaeformis* WE mouse mAbs were selected because they resulted in high signal and low background in ELISA assays: ADX184 (IgG) and ADX185 (IgM).

B. Performance of Coproantigen ELISA with *T. taeniaeformis* WE Mouse mAbs

Figure 5:
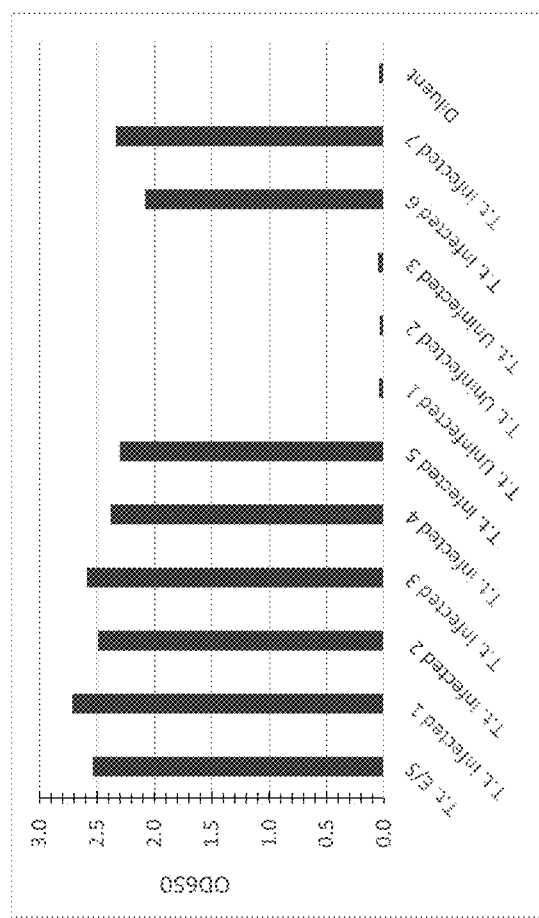
FIG. 5 shows the sensitivity of a sandwich coproantigen ELISA assay using antibody ADX185 coated onto a microtiter plate, followed by addition of the patient sample, then followed by addition of *T. taeniaeformis* WE rabbit pAb-HRP conjugate. The assay was run on FEX from 7 *T. taeniaeformis* positive felines, and 3 *T. taeniaeformis* negative felines as discussed in Example 2B (part B).

To assess sensitivity, a sandwich coproantigen ELISA assay was built with ADX185 coated onto a microtiter plate, followed by addition of the patient sample, then followed by addition of *T. taeniaeformis* WE rabbit pAb-HRP conjugate. The assay was run on FEX from 7 *T. taeniaeformis* positive felines, and 3 *T. taeniaeformis* negative felines. As shown in FIG. 5, the assay detected coproantigen in 7 out of the 7 positive samples, and in zero out of the 3 negative samples. Thus, the sensitivity of the ADX185/*T. taeniaeformis* WE rabbit pAb-HRP ELISA was 100% in this experiment.

Figure 6:
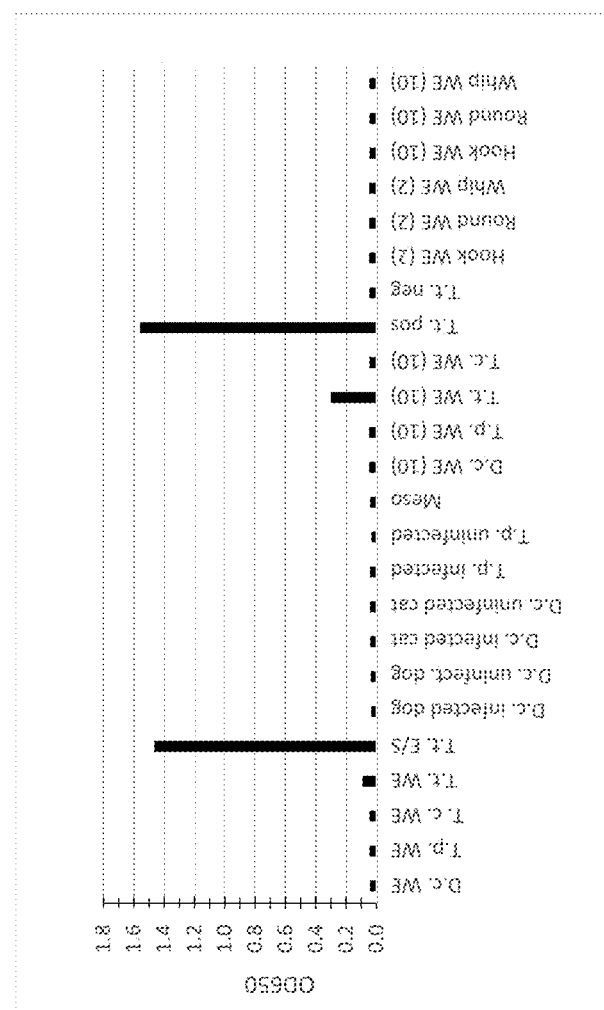
FIG. 6 shows the specificity of a sandwich coproantigen ELISA assay using antibody ADX184 coated onto a microtiter plate, and ADX193-HRP conjugate applied after addition of the patient sample. ADX193 is a *T. taeniaeformis* E/S mouse mAb, described below. The assay was run on *D. caninum* WE, *T. pisiformis* WE, *T. crassiceps* WE, *T. taeniaeformis* WE, *T. taeniaeformis* E/S, as well as the fecal extracts from a *D. caninum* positive dog, a *D. caninum* negative dog, a *D. caninum* positive cat, a *D. caninum* negative cat, a *T. pisiformis* positive dog, a *Taenia pisiformis* negative dog, a pool of three *T. taeniaeformis* positive felines, and a pool of three *T. taeniaeformis* negative felines as discussed in Example 2B (part B).

To assess specificity, a sandwich coproantigen ELISA was built with ADX184 coated onto a microtiter plate, and ADX193-HRP conjugate applied after addition of the patient sample. ADX193 is a *T. taeniaeformis* E/S mouse mAb, described below. The assay was run on *D. caninum* WE, *T. pisiformis* WE, *T. crassiceps* WE, *T. taeniaeformis* WE, *T. taeniaeformis* E/S, as well as the fecal extracts from a *D. caninum* positive dog, a *D. caninum* negative dog, a *D. caninum* positive cat, a *D. caninum* negative cat, a *T. pisiformis* positive dog, a *Taenia pisiformis* negative dog, a pool of three *T. taeniaeformis* positive felines, and a pool of three *T. taeniaeformis* negative felines. The beforementioned WEs were used at a concentration of 1 µg/ml protein. The assay was additionally run on several WE samples at 10 µg/ml protein and 2 µg/ml protein. The WE samples run at these higher concentrations were *D. caninum* WE, *T. pisiformis* WE, *T. taeniaeformis* WE, *T. crassiceps* WE, hookworm *Ancylostoma caninum* WE, roundworm *Toxocara canis* WE, and whipworm *Trichuris vulpis* WE. Among these samples and as shown in FIG. 6, the assay was positive only on *T. taeniaeformis* WE (at 10 µg/ml) and the pool of *T. taeniaeformis* positive felines. Thus, the ADX184/ADX193-HRP ELISA was highly specific in this experiment.

C. Preparation and Screening of *T. taeniaeformis* E/S Mouse mAb

Hybridomas were derived from the mice immunized with *T. taeniaeformis* E/S as described above. From the resulting mouse monoclonal antibody (mouse mAb) secreting hybridomas, five *T. taeniaeformis* E/S mouse mAbs were selected: ADX190, ADX191, ADX192, ADX193, ADX194. These five mouse mAbs were further assessed for their performance in an ELISA assay when each was paired with the anti-E/S mouse pAb-HRP conjugate. The of the five assays was run on *T. taeniaeformis* E/S, fecal extracts from seven *T. taeniaeformis* positive cats, and fecal extracts from three *T. taeniaeformis* negative cats. Each of the five assays detected all 7 positive feline samples. Each was also negative on the samples from the three negatives felines, although ADX193 and ADX194 had a higher background on one out the three negative feline samples.

Example 2C

Performance of an ELISA Using ADX184 with ADX193-HRP

An ELISA was built with ADX184 coated onto microtiter plates and ADX193 conjugated with HRP. Both mouse mAbs were used at a concentration of 5 ug/ml.

Figure 7:
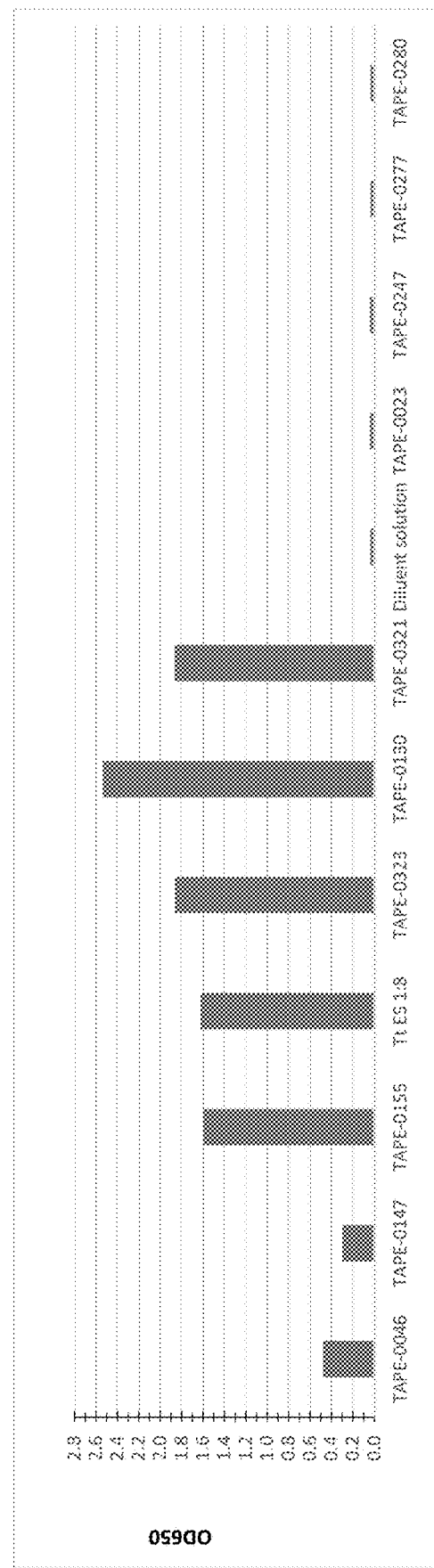
FIG. 7 shows the results of an ADX184/ADX193-HRP ELISA assay run on fecal extracts from six *T. taeniaeformis* positive cats, fecal extracts from four *T. taeniaeformis* negative cats, and one *T. taeniaeformis* E/S protein sample as discussed in Example 2C (part A).

The ADX184/ADX193-HRP ELISA was run on fecal extracts from six *T. taeniaeformis* positive cats, fecal extracts from four *T. taeniaeformis* negative cats, and one *T. taeniaeformis* E/S protein sample. As shown in FIG. 7, the assay detected coproantigen in all six positive fecal extracts and the E/S sample, but did not detect coproantigen in any of the four negative fecal extracts.

The ADX184/ADX193-HRP ELISA was run on fecal extracts from 68 *T. taeniaeformis* positive cats, and from 108 *T. taeniaeformis* negative cats that were *D. caninum* positive. The assay resulted in a positive signal in 55 out of the 68 *T. taeniaeformis* positive samples (80.9% sensitivity), and resulted in a positive signal in one out of the 108 *T. taeniaeformis* negative samples (99.1% specificity; 0.9% cross-reactivity with *D. caninum*).

Example 2D

Performance of an ELISA Using ADX191 with ADX194-HRP

Figure 8:
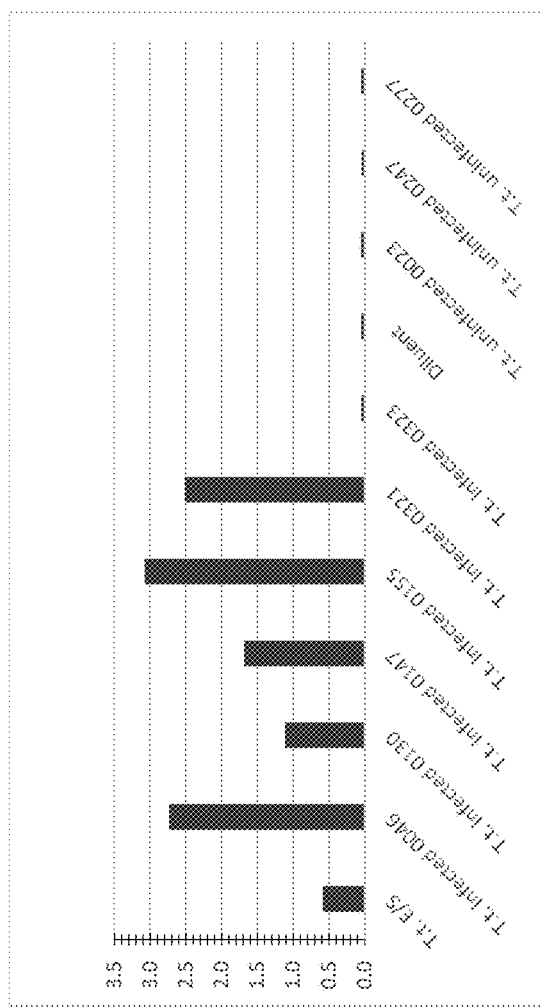
FIG. 8 shows the results of a coproantigen ELISA assay using antibody ADX191 coated onto microtiter plates and ADX194 conjugated with HRP. Both mouse mAbs were used at a concentration of 3 ug/ml. This ELISA was run on fecal extracts from six *T. taeniaeformis* positive cats, fecal extracts from four *T. taeniaeformis* negative cats, and one *T. taeniaeformis* E/S protein sample as discussed in Example 2D.

A coproantigen ELISA was built with ADX191 coated onto microtiter plates and ADX194 conjugated with HRP. Both mouse mAbs were used at a concentration of 3 ug/ml. This ELISA was run on fecal extracts from six *T. taeniaeformis* positive cats, fecal extracts from four *T. taeniaeformis* negative cats, and one *T. taeniaeformis* E/S protein sample. As shown in FIG. 8, the assay detected all six positive fecal extracts and the E/S sample, but did not detect coproantigen in any of the four negative fecal extracts.

Example 3A

A. Preparation of Rabbit pAb Against *Dipylidium caninum* TCA Soluble Fraction (*D. caninum* TCA Rabbit pAb)

A TCA fraction of *D. caninum* worms was prepared as described above and used to immunize two rabbits. Antiserum from one of these rabbits was chosen for further analysis.

B. Assessment of a *D. caninum* TCA Rabbit pAb ELISA Assay with Canine and Feline Samples.

In this coproantigen ELISA assay, the *D. caninum* TCA rabbit pAb was coated onto plates, contacted with FEX, then contacted with *D. caninum* TCA rabbit pAb-HRP conjugate, then contacted with a color substrate as described above.

Canine: The *D. caninum* TCA rabbit pAb ELISA assay was run on fecal extracts from 58 *D. caninum* positive dogs; the ELISA yielded a positive signal in 57 out of the 58 samples. The assay was also run on fecal extracts from 27 *D. caninum* negative dogs; the ELISA yielded a positive signal in 8 out of the 27 samples. Therefore, the assay was 98.3% sensitive and 70.4% specific in this experiment.

Feline: The *D. caninum* TCA rabbit pAb ELISA assay was run on fecal extracts from 31 *D. caninum* positive cats; the ELISA yielded a positive signal in 28 out of the 31 samples. The assay was also run on fecal extracts from 13 *D. caninum* negative cats; the ELISA yielded a positive signal in 5 out of the 13 samples. Therefore, the assay was 90.3% sensitive and 61.5% specific in this experiment.

Example 3B

A. Preparation of Rabbit pAb Against *D. caninum* WE Fraction (*D. caninum* WE Rabbit pAb).

WE was prepared from *D. caninum* worms (Antibody Systems) as described above and used to immunize two rabbits. Antiserum from one of these rabbits was chosen for further analysis.

B. Assessment of a *D. caninum* WE Rabbit pAb ELISA Assay

Figure 9:
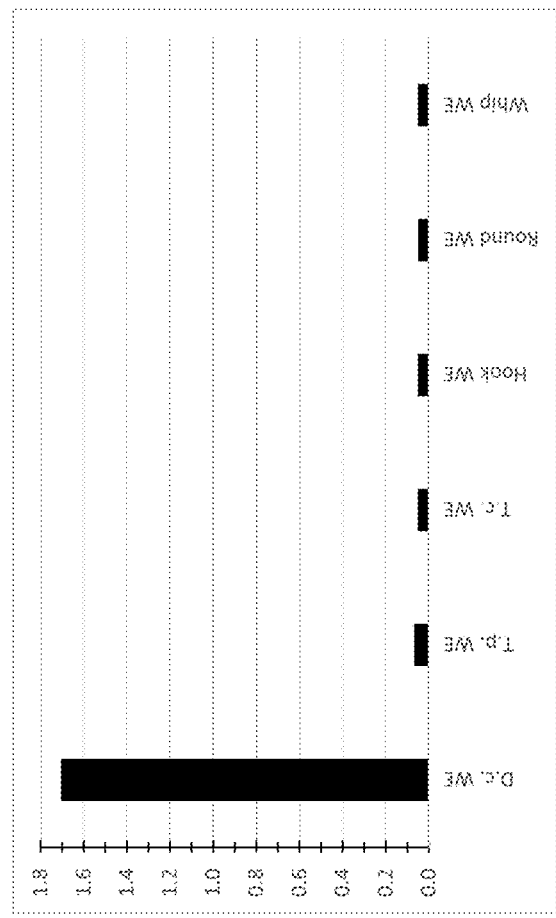
FIG. 9 shows the results of an ELISA assay using *D. caninum* WE rabbit pAb coated onto plates, contacted with FEX at 5 ug/ml, then contacted with *D. caninum* WE rabbit pAb-HRP conjugate at 3 ug/ml, then contacted with a color substrate. The *D. caninum* WE rabbit pAb ELISA assay was run on worm extracts from several helminth species: *D. caninum* WE, *Taenia pisiformis* WE, *T. crassiceps* WE, hookworm *Ancylostoma caninum* WE, roundworm *Toxocara canis* WE, whipworm *Trichuris vulpis* WE as discussed in Example 3B (part A).

In this ELISA assay, the *D. caninum* WE rabbit pAb was coated onto plates, contacted with FEX at 5 ug/ml, then contacted with *D. caninum* WE rabbit pAb-HRP conjugate at 3 ug/ml, then contacted with a color substrate as described above. This *D. caninum* WE rabbit pAb ELISA assay was run on worm extracts from several helminth species: *D. caninum* WE, *Taenia pisiformis* WE, *T. crassiceps* WE, hookworm *Ancylostoma caninum* WE, roundworm *Toxocara canis* WE, whipworm *Trichuris vulpis* WE. As shown in FIG. 9, only the *D. caninum* WE yielded a positive signal in this ELISA, demonstrating specificity of the assay in this experiment.

The performance of the *D. caninum* WE rabbit pAb ELISA assay was assessed in an additional experiment as follows. The assay was run on fecal extracts from 44 *D. caninum* positive dogs and 48 *D. caninum* negative dogs. The assay resulted in a positive signal in 16 out of the 44 positive samples and zero negative samples. Therefore, the assay was 36.4% sensitive and 100% specific in this experiment.

Example 3C

A. Preparation of Rabbit pAb Against *D. caninum* E/S (*D. caninum* E/S Rabbit pAb)

E/S was prepared from a *D. caninum* worm from a dog as described above and used to immunize two rabbits. Antiserum from one of these rabbits was chosen for further analysis.

B. Assessment of a *D. caninum* E/S Rabbit pAb ELISA Assay

In this coproantigen ELISA assay, the *D. caninum* E/S rabbit pAb was coated onto plates, contacted with FEX, then contacted with *D. caninum* WE rabbit pAb-HRP conjugate, then contacted with a color substrate as described above.

The assay was run on fecal extracts from 7 *D. caninum* positive dogs. The assay resulted in a positive signal in 4 out of the 7 positive samples. The assay resulted in a positive signal in one out of the four *D. caninum* negative dogs. Thus, the assay was 57.1% sensitive and 75% specific in this experiment.

Example 3D

A. Preparation of Rabbit mAb Against *D. caninum* WE (*D. caninum* WE Rabbit mAb)

WE was prepared from whole *D. caninum* worms from dogs as described above. Rabbits were immunized with the *Dipylidium caninum* WE according to a standard immunization procedure (SDIX, Windham, Me., USA). Following a boost at least 3 weeks after the initial immunization, a blood sample from the rabbit was used for monoclonal antibody development (ImmunoPrecise Antibodies, Ltd., (IPA), Victoria, British Columbia, Canada). B cells from the rabbit were collected and the B cell culture supernatants were evaluated on *D. caninum* WE coated 96-well plates and probed with secondary anti-rabbit IgG antibody. Approximately 50 μl of B cell supernatants from positive wells were tested for specific binding in a second screen (IDEXX) with various fecal extracts. The B cells of the best 32 candidates from this second screen were preserved in lysis buffer for cloning. RNA was isolated from these 32 candidates and rabbit antibody heavy and light (kappa) chain variable regions were cloned into separate mammalian expression vectors (IPA). Tissue culture supernatants collected from the mammalian cells transfected with the antibody heavy and light chain vectors were evaluated again with various fecal extracts. The top five clones of recombinant rabbit mAb DNA constructs were sequenced (IPA). Two out of these five rabbit mAb clones were chosen for further analysis: RDX13 and RDX12.

B. Assessment of a ELISA Assay with *D. caninum* WE Rabbit mAb on Canine and Feline Samples.

In this series of coproantigen ELISA assays, the mouse mAb ADX226 was coated onto plates, contacted with FEX, then contacted with RDX13-HRP and/or RDX12-HRP conjugates, then contacted with a color substrate as described above.

In a first experiment, the RDX13-HRP and RDX12-HRP conjugates were mixed, and the assay was run on fecal extracts from 38 *D. caninum* positive dogs, 28 *D. caninum* negative dogs, 20 *D. caninum* positive cats and 7 *D. caninum* negative cats. The assay yielded a positive signal in 28 out of the 38 positive dogs, 2 out of the 28 negative dogs, 18 out of the 20 positive cats, and zero out of the 7 negative cats. Thus, the assay resulted in 73.7% sensitivity and 92.9% specificity for dog samples, and 90.0% sensitivity and 100% specificity in cat samples, in this experiment.

In a second, third and fourth experiment, the RDX13-HRP and RDX12-HRP conjugates were used both individually and mixed, and the assay was run on fecal extracts from 37 *D. caninum* positive dogs, 28 *D. caninum* negative dogs, 21 *D. caninum* positive cats and 7 *D. caninum* negative cats.

In the second experiment, RDX13-HRP was used alone, the assay yielded a positive signal in 20 out of the 37 positive dogs, one out of the 28 negative dogs, 15 out of the 21 positive cats, and zero out of the 7 negative cats. Thus, the assay resulted in 54.1% sensitivity and 96.4% specificity for dog samples, and 71.4% sensitivity and 100% specificity for cat samples, in this experiment.

In the third experiment, RDX12-HRP was used alone, the assay yielded a positive signal in 13 out of the 37 positive dogs, one out of the 28 negative dogs, 16 out of the 21 positive cats, and zero out of the 7 negative cats. Thus, the assay resulted in 35.1% sensitivity and 96.4% specificity for dog samples, and 76.2% sensitivity and 100% specificity for cat samples, in this experiment.

In the fourth experiment, the RDX13-HRP and RDX12-HRP conjugates were mixed, the assay yielded a positive signal in 22 out of the 37 positive dogs, one out of the 28 negative dogs, 19 out of the 21 positive cats, and zero out of the 7 negative cats. Thus, the assay resulted in 59.5% sensitivity and 96.4% specificity for dog samples, and 90.5% sensitivity and 100% specificity for cat samples, in this experiment.

Example 3E

A. Preparation of Mouse pAb Against *D. caninum* WE (*D. caninum* WE Mouse pAb)

WE was prepared from *D. caninum* worms from dogs as described above and used to immunize mice. The resulting antiserum, *D. caninum* WE mouse pAb, was used in ELISA experiment described below.

B. Assessment of a ELISA Assay with *D. caninum* WE Mouse pAb on Canine and Feline Samples.

In this coproantigen ELISA assay, the *D. caninum* WE mouse pAb was coated onto plates, contacted with FEX, then contacted with *D. caninum* WE mouse pAb-HRP conjugate, then contacted with a color substrate as described above.

Figure 10:
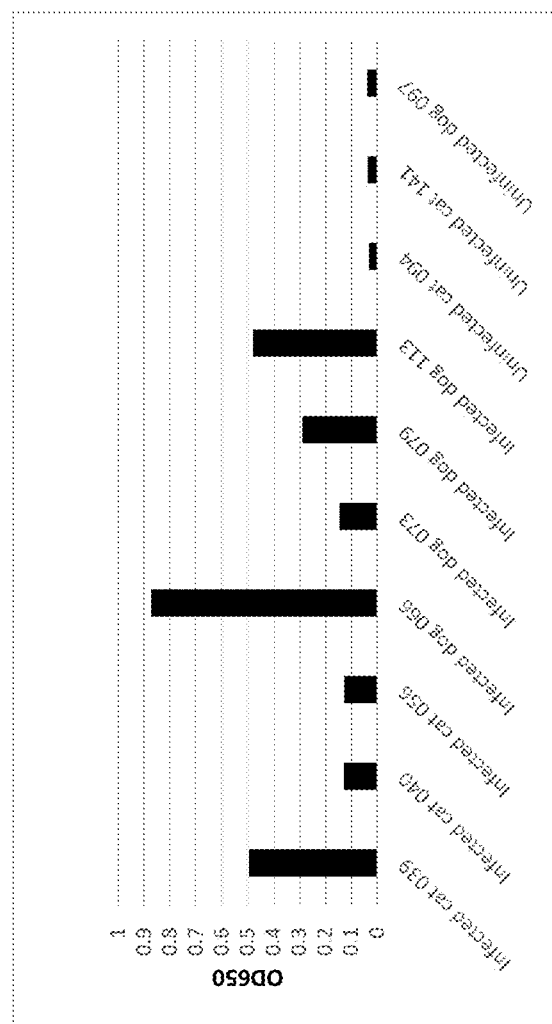
FIG. 10 shows the results of a coproantigen ELISA assay where *D. caninum* WE mouse pAb was coated onto plates, contacted with FEX, then contacted with *D. caninum* WE mouse pAb-HRP conjugate, then contacted with a color substrate as discussed in Example 3E (part A). The assay was run on fecal extracts from 4 *D. caninum* positive dogs and 3 *D. caninum* positive cats; one *D. caninum* negative cat infected with *Giardia* and *T. taeniaeformis*, one *D. caninum* negative cat infected with *T. taeniaeformis*, and one *D. caninum* negative dog that was infected with *Toxocara canis* and *Taenia pisiformis* as discussed in Example 3E (part A).

The assay was run on fecal extracts from 4 *D. caninum* positive dogs and 3 *D. caninum* positive cats; one *D. caninum* negative cat infected with *Giardia* and *T. taeniaeformis*, one *D. caninum* negative cat infected with *T. taeniaeformis*, and one dog infected with *Toxocara* and *Taenia pisiformis*. As shown in FIG. 10, the assay yielded a positive signal in 4 out of the 4 positive dogs, in zero out of the one negative dog, in 3 out of the 3 positive cats, and in zero out of the 2 negative cats. Therefore, the assay resulted in a high degree of specificity and sensitivity in this experiment.

Example 3F

A. Preparation of Mouse mAb Against *D. caninum* TCA Soluble Fraction (*D. caninum* TCA Mouse mAb)

TCA soluble fraction was prepared from *D. caninum* worms from dogs as described above and used to immunize mice (MBS). The spleen of an immunized mouse was used to generate a mouse mAb, ADX251, which was used in the following ELISA experiments.

B. Assessment of ELISA Assays with *D. caninum* TCA Mouse mAb on Canine and Feline Samples.

In a first coproantigen ELISA configuration, mouse mAb ADX226 was coated onto plates, contacted with FEX, then contacted with mouse mAb ADX251-HRP conjugate followed by color substrate.

Figure 11:
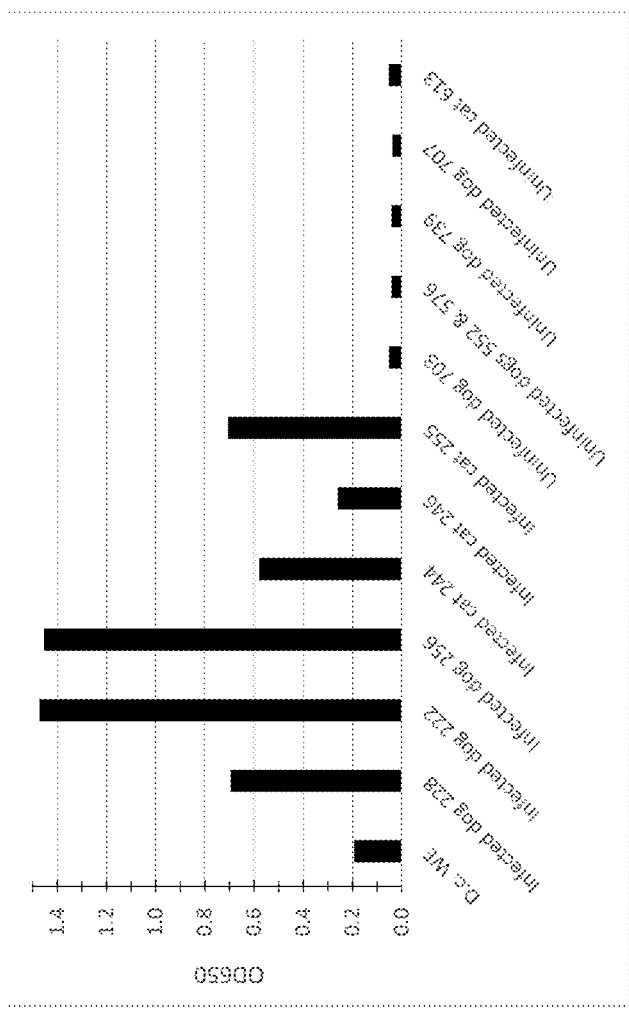
FIG. 11 shows the results of a first coproantigen ELISA assay which used mouse mAb ADX226 coated onto plates, contacted with FEX, then contacted with mouse mAb ADX251-HRP conjugate followed by color substrate. The assay was run on fecal extracts from 3 *D. caninum* positive dogs, 5 *D. caninum* negative dogs; 3 *D. caninum* positive cats, and 1 *D. caninum* negative cat as discussed in Example 3F (part A).

The assay was run on fecal extracts from 3 *D. caninum* positive dogs, 5 *D. caninum* negative dogs; 3 *D. caninum* positive cats, and 1 *D. caninum* negative cat. As shown in FIG. 11, the assay yielded a positive signal in 3 out of the 3 positive dogs, in zero out of the five negative dogs, in 3 out of the 3 positive cats, and in zero out of the 1 negative cat. Therefore, the assay resulted in a high degree of specificity and sensitivity in this experiment.

Figure 12:
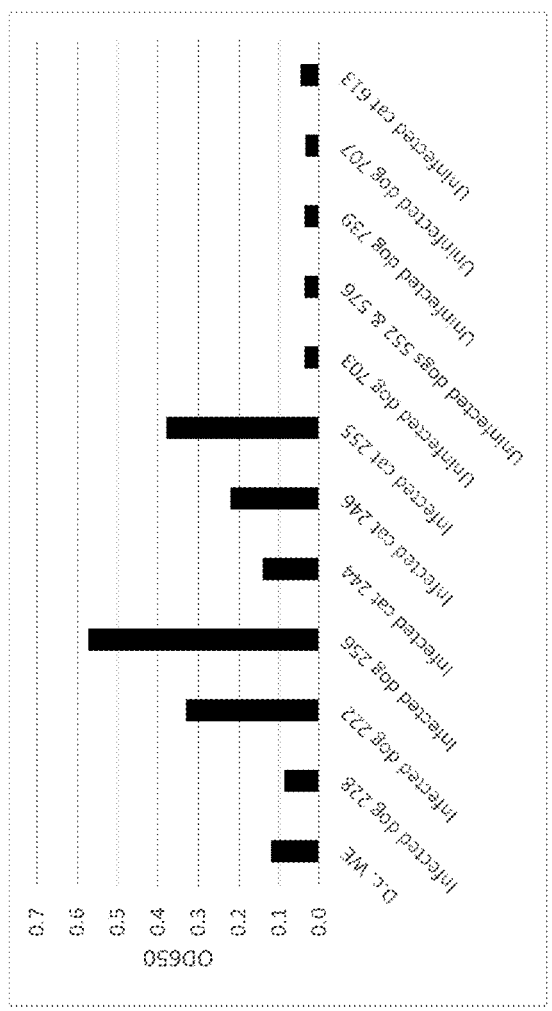
FIG. 12 shows the results of a second coproantigen ELISA assay which used mouse mAb ADX251 was coated onto plates, contacted with FEX, then contacted with mouse mAb ADX227-HRP conjugate, followed by color substrate. The assay was run on fecal extracts from 3 *D. caninum* positive dogs, 5 *D. caninum* negative dogs; 3 *D. caninum* positive cats, and 1 *D. caninum* negative cat as discussed in Example 3F (part A).

In a second coproantigen ELISA configuration, mouse mAb ADX251 was coated onto plates, contacted with FEX, then contacted with mouse mAb ADX227-HRP conjugate, followed by color substrate. The assay was run on fecal extracts from 3 *D. caninum* positive dogs, 5 *D. caninum* negative dogs; 3 *D. caninum* positive cats, and 1 *D. caninum* negative cat. As shown in FIG. 12, the assay yielded a positive signal in 3 out of the 3 positive dogs, in zero out of the five negative dogs, in 3 out of the 3 positive cats, and in zero out of the 1 negative cat. Therefore, the assay resulted in a high degree of specificity and sensitivity in this experiment.

Figure 13:
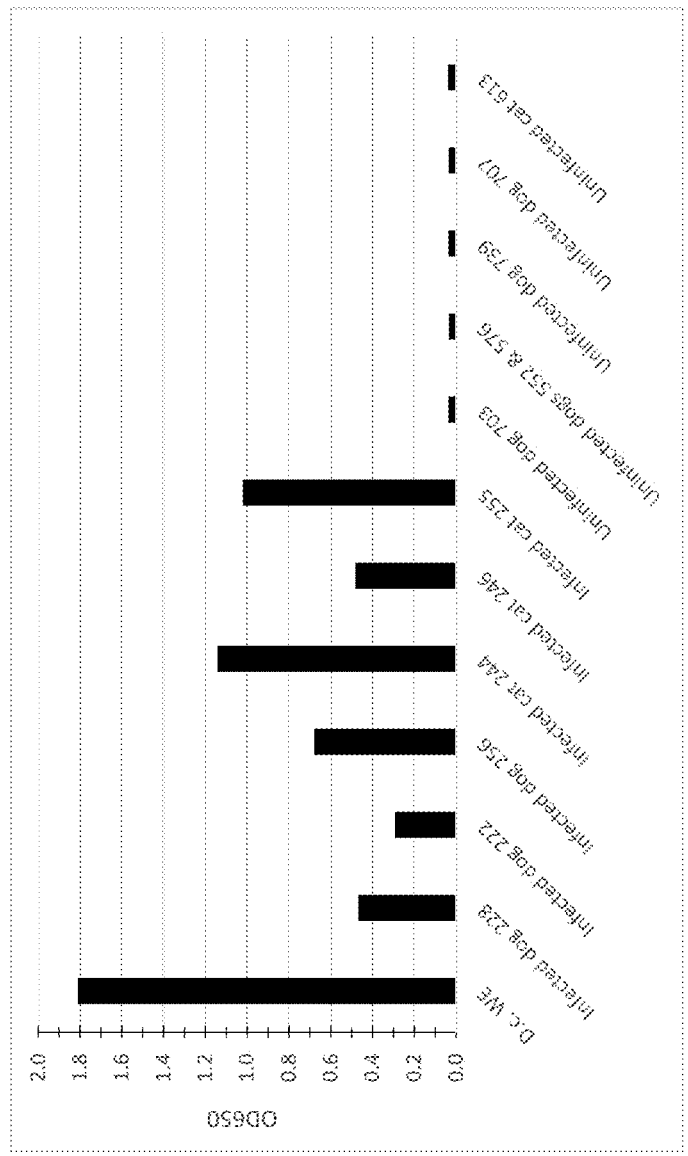
FIG. 13 shows the results of a third coproantigen ELISA assay which used mouse mAb ADX251 coated onto plates, contacted with FEX, then contacted with *D. caninum* WE rabbit pAb-HRP conjugate, followed by color substrate. The assay was run on fecal extracts from 3 *D. caninum* positive dogs, 5 *D. caninum* negative dogs; 3 *D. caninum* positive cats, and 1 *D. caninum* negative cat as discussed in Example 3F (part A).

In a third coproantigen ELISA configuration, mouse mAb ADX251 was coated onto plates, contacted with FEX, then contacted with *D. caninum* WE rabbit pAb-HRP conjugate, followed by color substrate. The assay was run on fecal extracts from 3 *D. caninum* positive dogs, 5 *D. caninum* negative dogs; 3 *D. caninum* positive cats, and 1 *D. caninum* negative cat. As shown in FIG. 13, the assay yielded a positive signal in 3 out of the 3 positive dogs, in zero out of the five negative dogs, in 3 out of the 3 positive cats, and in zero out of the 1 negative cat. Therefore, the assay resulted in a high degree of specificity and sensitivity in this experiment.

Example 3G

A. Preparation of Mouse mAb Against *D. caninum* WE (*D. caninum* WE Mouse mAb)

WE was prepared from *D. caninum* worms from dogs as described above and used to immunize mice. From these mice, four monoclonal antibodies (ADX224, ADX225, ADX226 and ADX227) were generated as described above and chosen for further analysis.

B. Assessment of ELISA Assays with *D. caninum* WE Mouse mAb on Canine and Feline Samples.

The following ELISA configurations were run on fecal extracts from 3 *D. caninum* positive dogs, 4 *D. caninum* negative dogs; 3 *D. caninum* positive cats, and 1 *D. caninum* negative cat.

Figure 14:
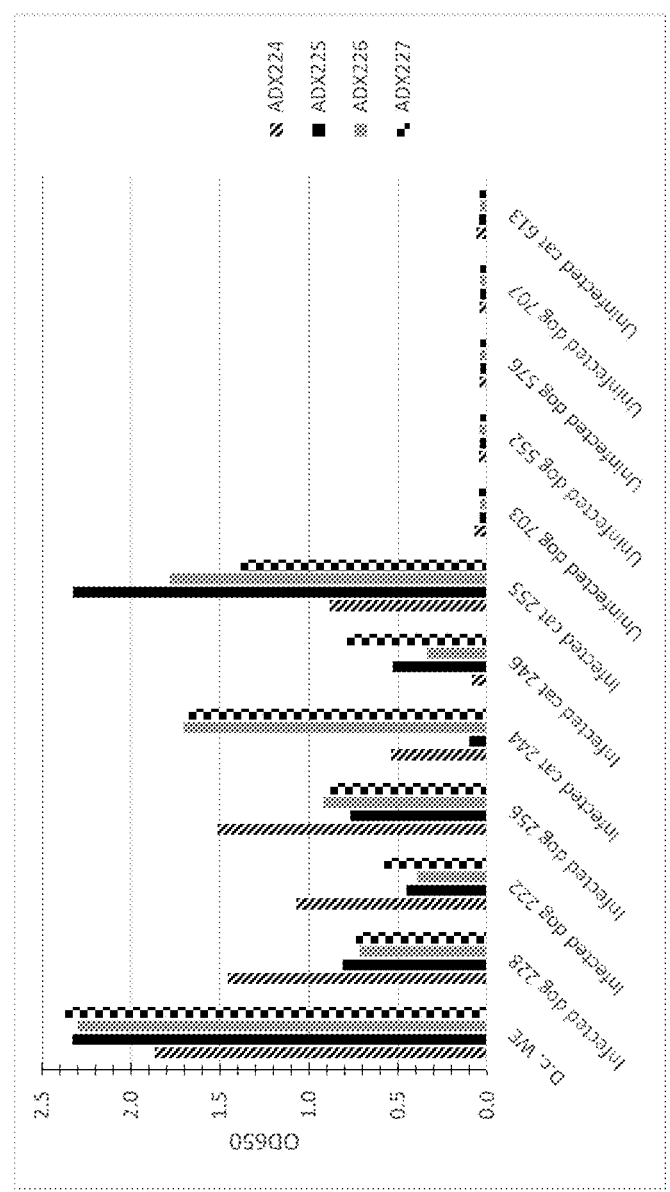
FIG. 14 shows the results of a first set of coproantigen ELISA assay configurations where *D. caninum* WE mouse mAbs ADX224, ADX225, ADX226 and ADX227 were coated individually onto plates, contacted with FEX, then contacted with *D. caninum* WE rabbit pAb-HRP conjugate followed by color substrate as discussed in Example 3G (part A).

In a first set of coproantigen ELISA configurations, the *D. caninum* WE mouse mAbs were coated individually onto plates, contacted with FEX, then contacted with *D. caninum* WE rabbit pAb-HRP conjugate followed by color substrate. The results are shown in FIG. 14. Thus, an assay with ADX224 on the plate detected coproantigen in 5 out of six positive samples and in zero negative samples. An assay with ADX225 on the plate detected coproantigen in six out of six positive samples and in zero negative samples. An assay with ADX226 on the plate detected coproantigen in six out of six positive samples and in zero negative samples. The assay with ADX227 on the plate detected coproantigen in six out of six positive samples and in zero negative samples.

Figure 15:
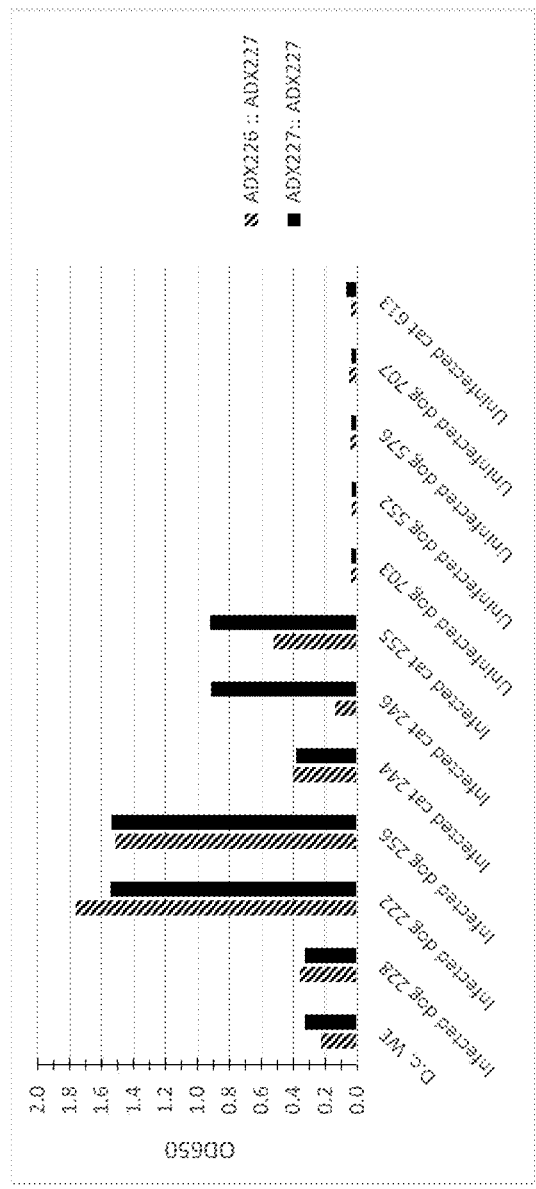
FIG. 15 shows the results of a second set of coproantigen ELISA assay configurations, where *D. caninum* WE mouse mAbs ADX226 and ADX227 were coated individually onto plates, contacted with FEX, then contacted with *D. caninum* WE mouse mAb-HRP conjugate ADX227-HRP followed by color substrate as discussed in Example 3G (part A).

In a second set of coproantigen ELISA configurations, each of the four *D. caninum* WE mouse mAbs were coated individually onto plates, contacted with FEX, then contacted with each of the four *D. caninum* WE mouse mAb-HRP conjugates followed by color substrate. The results are shown in FIG. 15. Among the tested combinations, two pairings were chosen. An assay with ADX226 on the plate and ADX227-HRP detected coproantigen in six out of six positive samples and in zero negative samples; and an assay with ADX227 on the plate and ADX227-HRP detected coproantigen in six out of six positive samples and in zero negative samples. This successful pairing of ADX227 with itself suggests that the coproantigen detected by ADX227 contains a repetitive epitope.

Example 3H

A. Antigen Characterization: Glycosylation of the Antigens Bound by the Anti-*D. caninum* Antibody ADX226

Figure 16:
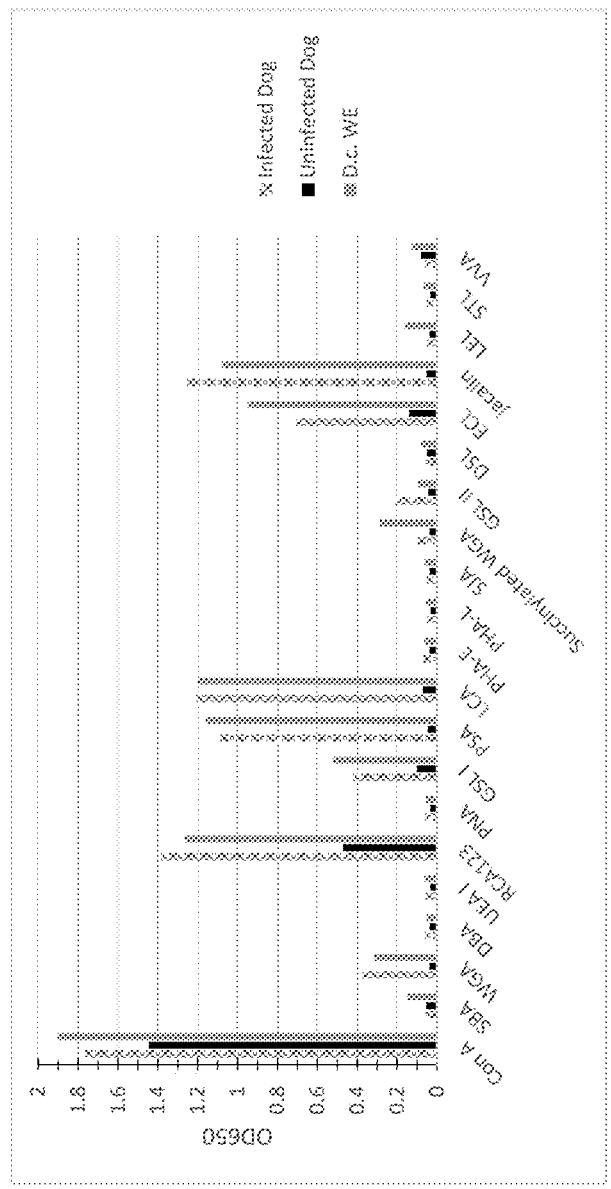
FIG. 16 shows the results of determining whether the coproantigen bound by *D. caninum* WE mouse mAb ADX226 is glycosylated by testing the ability of 21 different lectins to bind the coproantigen using a commercial kit (Biotinylated lectin kits I, II and III from Vector Laboratories, Burlingame, Calif.) as discussed in Example 3H (part 1).

In order to determine whether the coproantigen bound by *D. caninum* WE mouse mAb ADX226 is glycosylated, the ability of 21 different lectins were tested for their ability to bind the coproantigen using a commercial kit (Biotinylated lectin kits I, II and III from Vector Laboratories, Burlingame, Calif.). The assays were carried out according to the manufacturer's instructions. Briefly, ADX226 was coated into Immulon 1b plates. FEX from *D. caninum* positive or negative canines was added to plates. After washing, the lectin::biotin conjugates were added, followed by streptavidin-HRP and the color substrate. The results are shown in FIG. 16. In this test, the following lectins bound specifically and strongly to ADX226 coproantigen: PSA, LCA, Jacalin, ECL, GSL1, RCA123, and WGA. This lectin binding data indicates that the *D. caninum* coproantigen bound by the ADX226 is glycosylated.

Figure 17:
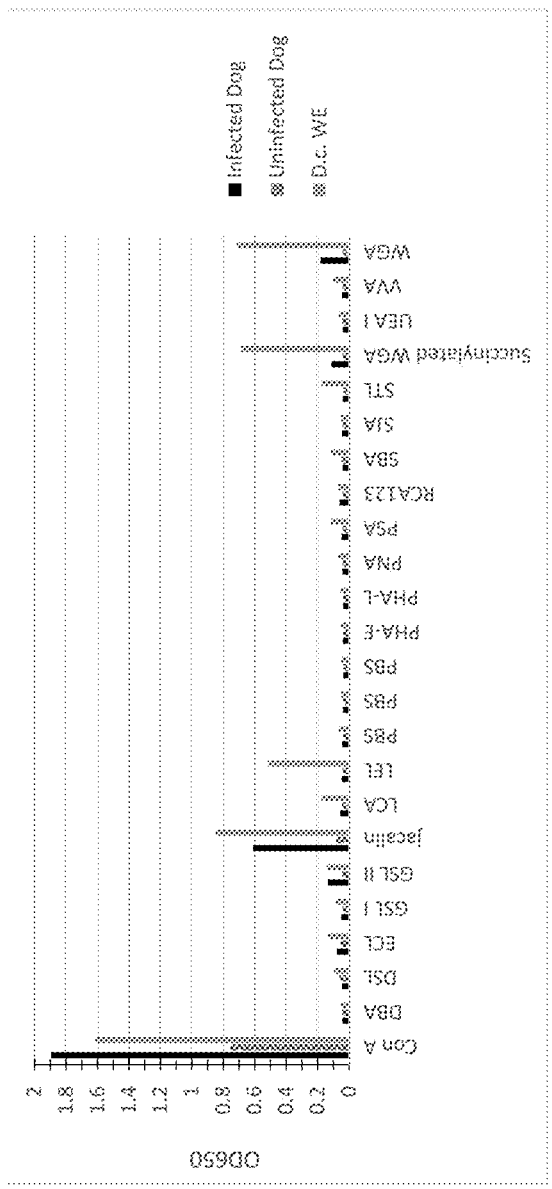
FIG. 17 shows the results of determining whether the coproantigen bound by the antibody *D. caninum* WE rabbit pAb is glycosylated by testing 21 different lectins for their ability to bind the coproantigen using a commercial kit (Biotinylated lectin kits I, II and III from Vector Laboratories, Burlingame, Calif.) as discussed in Example 3H (part 2).

B. Antigen Characterization: Glycosylation of the Antigens Bound by the Anti-*D. caninum* WE Rabbit pAb In order to determine whether the coproantigen bound by the antibody *D. caninum* WE rabbit pAb is glycosylated, 21 different lectins were tested for their ability to bind the coproantigen using a commercial kit (Biotinylated lectin kits I, II and III from Vector Laboratories, Burlingame, Calif.). The assays were carried out according to the manufacturer's instructions. Briefly, *D. caninum* WE rabbit pAb was coated into Immulon 1b plates. FEX from *D. caninum* positive or negative canines and felines was added to plates. After washing, the lectin::biotin conjugates were added, followed by streptavidin-HRP and the color substrate. In this test, the following lectins bound to *D. caninum* WE rabbit pAb coproantigen: Jacalin, WGA, succinylated WGA, GSL II. The results are shown in FIG. 17. This lectin binding data indicates that the *D. caninum* coproantigen bound by *D. caninum* WE rabbit pAb is glycosylated. This data also shows that an antibody-lectin sandwich assay can be used to detect *D. caninum* coproantigen.

C. Antigen Characterization: Glycosylation of the Antigens Bound by the Anti-*D. caninum* Antibodies *D. caninum* WE Rabbit pAb and ADX187

Figure 18:
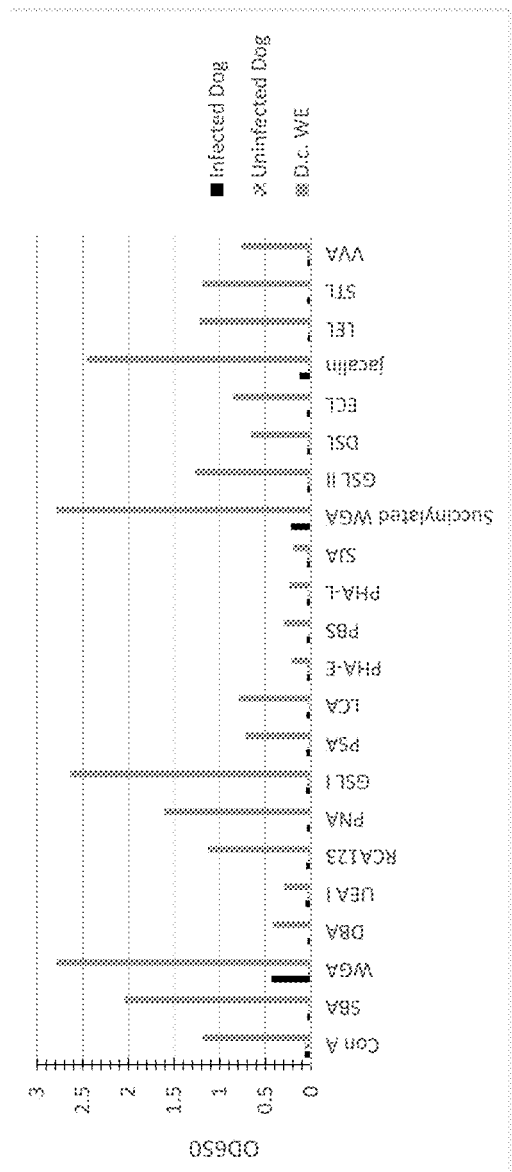
FIG. 18 shows the results of determining whether the coproantigen(s) bound by the *D. caninum* WE rabbit pAb and ADX187 (a *D. caninum* WE mouse mAb) are glycosylated by testing 21 different lectins for their ability to bind the coproantigen using a commercial kit (Biotinylated lectin kits I, II and III from Vector Laboratories, Burlingame, Calif.) as discussed Example 3H (part 3).

A similar assay configuration was used to determine whether the coproantigen(s) bound by the *D. caninum* WE rabbit pAb and ADX187 (a *D. caninum* WE mouse mAb) are glycosylated, 21 different lectins were tested for their ability to bind the coproantigen using a commercial kit (Biotinylated lectin kits I, II and III from Vector Laboratories, Burlingame, Calif.). In this configuration, the 21 different biotinylated lectins were coated into Immulon 1b plates. FEX from *D. caninum* positive or negative canines was added to plates. After washing, the *D. caninum* WE rabbit pAb-HRP or the ADX187-HRP conjugates were added, followed by streptavidin-HRP and the color substrate. The results are shown in FIG. 18. In this test, the following lectins bound to *D. caninum* WE rabbit pAb coproantigen: Jacalin, WGA, and succinylated WGA. The same set of lectins bound the ADX187 coproantigen: Jacalin, WGA, and succinylated WGA. This lectin binding data confirms that the *D. caninum* coproantigen(s) bound by *D. caninum* WE rabbit pAb and ADX187 is glycosylated. This data also shows that an antibody-lectin sandwich assay can be used to detect *D. caninum* coproantigen.

Further Testing of O-Glycosylation of the Coproantigen Recognized by ADX226

In this experiment, ADX226 was coated onto microtiter plates, followed by FEX, then jacalin-biotin, then streptavidin-HRP, and finally the HRP substrate. The FEX were prepared from fecal extracts of 20 *D. caninum* positive dogs, 24 *D. caninum* negative dogs, 12 *D. caninum* positive cats, and 3 *D. caninum* negative cats. The assay resulted in a positive signal in 18 out of the 20 positive dogs (95% sensitivity), zero out of 24 negative dogs (100% specificity), 11 out of 12 positive cats (91.7% sensitivity), and zero out of 3 negative cats (100% specificity). This data demonstrates that the ADX226 coproantigen is O-glycosylated and that a sandwich immunoassay using an antibody and a lectin can be used to detect tapeworm coproantigen.

Example 4

A series of fecal ELISA sandwich assays was performed in microtiter plates essentially as described in section "EXAMPLE A" above to test the specificity of ELISA assays for the detection of tapeworm *T. pisiformis*, tapeworm *T. taeniaeformis*, tapeworm *D. caninum*, hookworm *Ancylostoma caninum* (*A. caninum*), hookworm *Ancylostoma tubaeforme* (*A. tubaeforme*), roundworm *Toxocara canis* (*T. canis*), roundworm *Toxocara cati* (*T. cati*), whipworm *Trichuris vulpis* (*T. vulpis*), whipworm *Trichuris felis* (*T. felis*) and protozoon *Giardia lamblia* (*Giardia*).

Fecal extracts from the following sources were tested in the ELISA assays: *T. pisiformis* positive dog (FIG. 19, column 1), *T. taeniaeformis* infected cat (FIG. 19, column 2), *D. caninum* infected dog (FIG. 19, column 3), *D. caninum* infected cat (FIG. 19, column 4), hookworm *A.*

Figure 19:
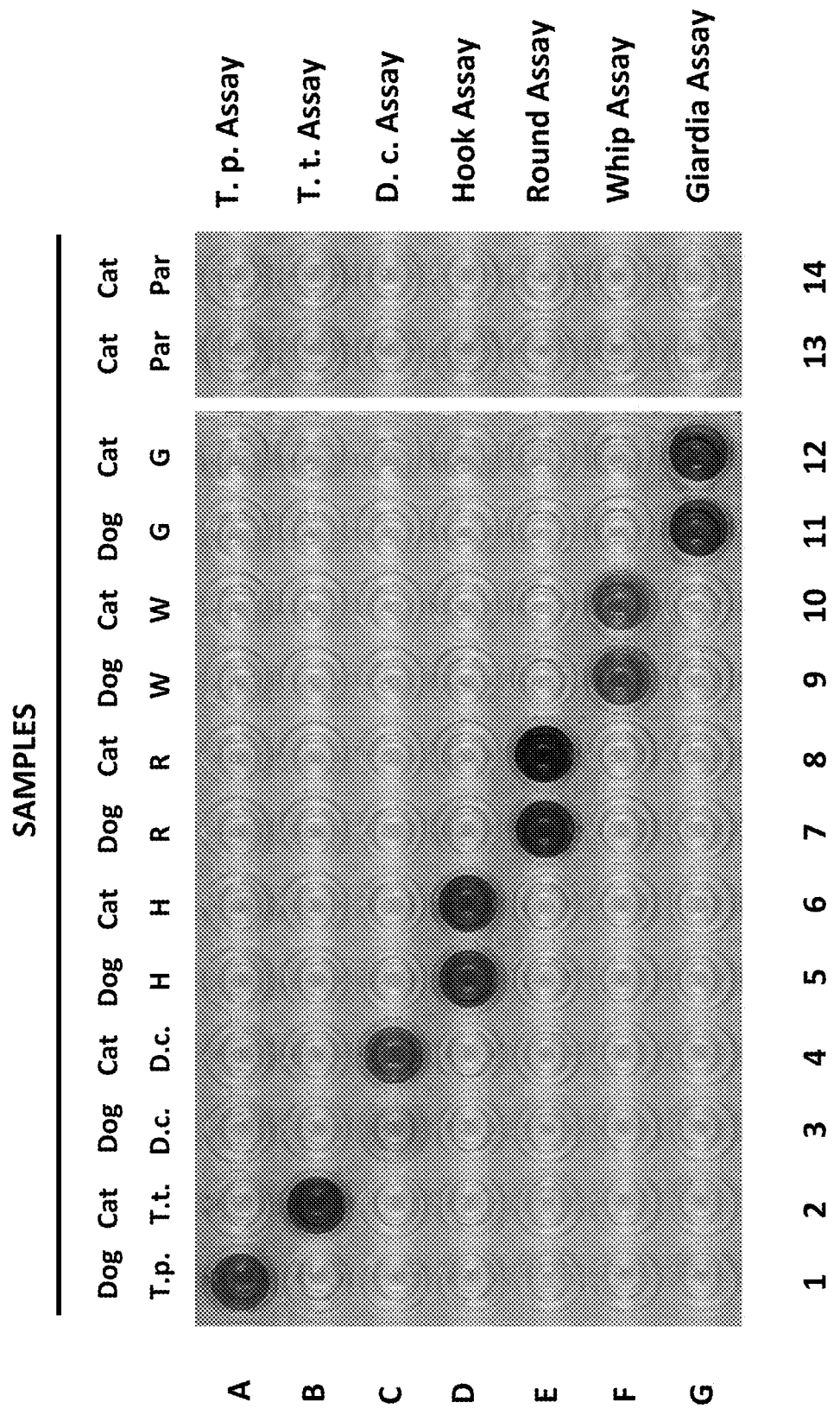
FIG. 19 shows microtiter plates in which a series of T.p., *T. taeniaeformis*, D.c., hookworm, roundworm, whipworm and Giardia ELISA assays were carried out using fecal extracts of a variety of infected canines and felines as discussed in Example 4. Fecal extracts from the following sources were tested in the ELISA assays: *T. pisiformis* positive dog (FIG. 19, column 1), *T. taeniaeformis* infected cat (FIG. 19, column 2), *D. caninum* infected dog (FIG. 19, column 3), *D. caninum* infected cat (FIG. 19, column 4), hookworm *A. caninum* infected dog (FIG. 19, column 5), hookworm *A. tubaeforme* infected cat (FIG. 19, column 6), roundworm *T. canis* infected dog (FIG. 19, column 7), roundworm *T. cati* infected cat (FIG. 19, column 8), whipworm *T. vulpis* infected dog (FIG. 19, column 9), whipworm *T. felis* infected cat (FIG. 19, column 10), Giardia infected dog (FIG. 19, column 11), Giardia infected cat (FIG. 19, column 12), and two parvovirus infected cats (FIG. 19, columns 13 and 14).

*caninum* infected dog (FIG. 19, column 5), hookworm *A. tubaeforme* infected cat (FIG. 19, column 6), roundworm *T. canis* infected dog (FIG. 19, column 7), roundworm *T. cati* infected cat (FIG. 19, column 8), whipworm *T. vulpis* infected dog (FIG. 19, column 9), whipworm *T. felis* infected cat (FIG. 19, column 10), Giardia infected dog (FIG. 19, column 11), Giardia infected cat (FIG. 19, column 12), and two parvovirus infected cats (FIG. 19, columns 13 and 14). In FIG. 19, columns 1 through 12 are an image of a single microtiter plate, and columns 13 and 14 are an image of another, separate microtiter plate.

Tapeworm *T. pisiformis* Coproantigen ELISA (FIG. 19, Row A).

A sandwich ELISA assay for the detection of *T. pisiformis* coproantigen was built. Briefly, mAb ADX131 was coated onto microtiter plates, incubated with fecal extract, then incubated with mAb ADX132-HRP conjugate, followed by detection with a peroxidase substrate. ADX131 was coated at a concentration of 3 ug/ml. ADX132-HRP was used at a concentration of 3 ug/ml. The results show that this *T. pisiformis* coproantigen ELISA yielded a positive signal with FEX from *T. pisiformis* infected dog. However, this *T. pisiformis* ELISA did not detect coproantigen in FEX from any of the following: Tapeworm *T. taeniaeformis* infected cat, *D. caninum* infected dog, *D. caninum* infected cat, hookworm *A. caninum* infected dog, hookworm *A. tubaeforme* infected cat, roundworm *T. canis* infected dog, roundworm *T. cati* infected cat, whipworm *T. vulpis* infected dog, whipworm *T. felis* infected cat, Giardia infected dog, Giardia infected cat, and Parvovirus infected cat (FIG. 19, Row A). Therefore, this *T. pisiformis* ELISA specifically detected *T. pisiformis* coproantigen and did not crossreact with coproantigen from any of the following: Tapeworm *T. taeniaeformis*, tapeworm *D. caninum*, hookworm *A. caninum*, roundworm *T. canis*, roundworm *T. cati*, whipworm *T. vulpis*, whipworm *T. felis*, protozoon *Giardia lamblia*, and feline parvovirus. Thus, this *T. pisiformis* ELISA was highly species specific. This *T. pisiformis* ELISA is useful for the detection or diagnosis of infection or infestation with *T. pisiformis*. This *T. pisiformis* ELISA can be used to distinguish infection with *T. pisiformis* from infection with tapeworm *T. taeniaeformis*, tapeworm *D. caninum*, hookworm *A. caninum*, hookworm *A. tubaeforme*, roundworm *T. canis*, roundworm *T. cati*, whipworm *T. vulpis*, whipworm *T. felis*, protozoon *Giardia lamblia*, canine parvovirus and feline parvovirus.

Tapeworm *T. taeniaeformis* Coproantigen ELISA (FIG. 19, Row B).

A sandwich ELISA assay for the detection of *Taenia taeniaeformis* coproantigen was built. Briefly, mAb ADX184 was coated onto microtiter plates, incubated with fecal extract, then incubated with mouse mAb ADX193-HRP conjugate, followed by detection with a peroxidase substrate. ADX184 was coated at a concentration of 5 ug/ml. ADX193-HRP was used at a concentration of 3 ug/ml. The results show that this *T. taeniaeformis* coproantigen ELISA yielded a positive signal with FEX from *T. taeniaeformis* infected dog. However, this *T. taeniaeformis* ELISA did not detect coproantigen in FEX from any of the following: Tapeworm *T. pisiformis* infected dog, *D. caninum* infected dog, *D. caninum* infected cat, hookworm *A. caninum* infected dog, hookworm *A. tubaeforme* infected cat, roundworm *T. canis* infected dog, roundworm *T. cati* infected cat, whipworm *T. vulpis* infected dog, whipworm *T. felis* infected cat, Giardia infected dog, Giardia infected cat, and Parvovirus infected cat (FIG. 19, Row B). Therefore, this *T. taeniaeformis* ELISA specifically detected *T. taeniaeformis* coproantigen and did not crossreact with coproantigen from any of the following: Tapeworm *T. pisiformis*, tapeworm *D. caninum*, hookworm *A. caninum*, hookworm *A. tubaeforme*, roundworm *T. canis*, roundworm *T. cati*, whipworm *T. vulpis*, whipworm *T. felis*, protozoon *Giardia lamblia*, and feline parvovirus. Thus, this *T. taeniaeformis* ELISA was highly species specific. This *T. taeniaeformis* ELISA is useful for the detection or diagnosis of infection or infestation with *T. taeniaeformis*. This *T. taeniaeformis* ELISA can be used to distinguish infection with tapeworm *T. taeniaeformis* from infection with tapeworm *T. pisiformis*, tapeworm *D. caninum*, hookworm *A. caninum*, hookworm *A. tubaeforme*, roundworm *T. canis*, roundworm *T. cati*, whipworm *T. vulpis*, whipworm *T. felis*, protozoon *Giardia lamblia*, canine parvovirus and feline parvovirus.

Tapeworm *D. caninum* Coproantigen ELISA (FIG. 19, Row C).

A sandwich ELISA assay for the detection of *D. caninum* coproantigen was built. Briefly, mAb ADX226 was coated onto microtiter plates, incubated with fecal extract, then incubated with mAb RDX5-HRP conjugate, followed by detection with a peroxidase substrate. ADX226 was coated at a concentration of 3 ug/ml. RDX5-HRP was used at a concentration of 3 ug/ml. The results show that this *D. caninum* coproantigen ELISA yielded a positive signal with FEX from *D. caninum* infected dog and *D. caninum* infected cat. However, this *D. caninum* ELISA did not detect coproantigen in FEX from any of the following: Tapeworm *T. pisiformis* infected dog, *T. taeniaeformis* infected cat, hookworm *A. caninum* infected dog, hookworm *A. tubaeforme* infected cat, roundworm *T canis* infected dog, roundworm *T. cati* infected cat, whipworm *T. vulpis* infected dog, whipworm *T. felis* infected cat, Giardia infected dog, Giardia infected cat, and Parvovirus infected cat (FIG. 19, Row C). Therefore, this *D. caninum* ELISA specifically detected *D. caninum* coproantigen and did not crossreact with coproantigen from any of the following: Tapeworm *T. taeniaeformis*, tapeworm *T. pisiformis*, hookworm *A. caninum*, hookworm *A. tubaeforme*, roundworm *T. canis*, roundworm *T. cati*, whipworm *T. vulpis*, whipworm *T. felis*, protozoon *Giardia lamblia*, and feline parvovirus. Thus, this *D. caninum* ELISA was highly species specific and is useful for the detection or diagnosis of infection or infestation with *D. caninum*. This *D. caninum* ELISA can be used to distinguish infection with *D. caninum* from infection with tapeworm *T. pisiformis*, tapeworm *T. taeniaeformis*, hookworm *A. caninum*, hookworm *A. tubaeforme*, roundworm *T. canis*, roundworm *T. cati*, whipworm *T. vulpis*, whipworm *T. felis*, protozoon *Giardia lamblia*, canine parvovirus and feline parvovirus.

Hookworm *Ancylostoma* Coproantigen ELISA (FIG. 19, Row D).

A sandwich ELISA assay for the detection of *A. caninum* coproantigen was built. Briefly, a polyclonal rabbit anti-ASP5-1 antibody was coated onto microtiter plates, incubated with fecal extract, then incubated with mouse anti-ASP5-1 mAb-HRP conjugate, followed by detection with a peroxidase substrate as discussed in U.S. Pat. No. 7,951,547, which is incorporated by reference in its entirety. The rabbit polyclonal antibody was coated at a concentration of 5 ug/ml. The mouse mAb was used at a concentration of 4 ug/ml. The results show that this *Ancylostoma* coproantigen ELISA yielded a positive signal with FEX from *A. caninum* infected dog and *A. tubaeforme* infected cat. However, this *Ancylostoma* ELISA did not detect coproantigen in FEX from any of the following: Tapeworm *T. pisiformis* infected dog, tapeworm *T. taeniaeformis* infected cat, tapeworm *D.*

*caninum* infected dog, tapeworm *D. caninum* infected cat, roundworm *T. canis* infected dog, roundworm *T. cati* infected cat, whipworm *T. vulpis* infected dog, whipworm *T. felis* infected cat, *Giardia* infected dog, *Giardia* infected cat, and Parvovirus infected cat (FIG. 19, Row D). Therefore, this *Ancylostoma* ELISA specifically detected *A. caninum* and *A. tubaeforme* coproantigen and did not crossreact with coproantigen from any of the following: Tapeworm *T. taeniaeformis*, tapeworm *T. pisiformis*, tapeworm *D. caninum*, roundworm *T canis*, roundworm *T. cati*, whipworm *T. vulpis*, whipworm *T. felis*, protozoon *Giardia lamblia*, and feline parvovirus. Thus, this *Ancylostoma* ELISA was highly specific and useful for the detection or diagnosis of infection or infestation with hookworm *A. caninum* and *A. tubaeforme*. Furthermore, this *Ancylostoma* ELISA can be used to distinguish infection with hookworm *A. caninum* or *A. tubaeforme* from infection with tapeworm *T. pisiformis*, tapeworm *T. taeniaeformis*, tapeworm *D. caninum*, roundworm *T. canis*, roundworm *T. cati*, whipworm *T. vulpis*, whipworm *T. felis*, protozoon *Giardia lamblia*, canine parvovirus and feline parvovirus.

Roundworm *Toxocara* Coproantigen ELISA (FIG. 19, Row E).

A sandwich ELISA assay for the detection of *T. canis* and *T. cati* coproantigen was built. Briefly, a mouse mAb raised against *T. canis* protein DIV6728C was coated onto microtiter plates, incubated with fecal extract, then incubated with an HRP conjugate of another mouse mAb raised against *T. canis* protein DIV6728C, followed by detection with a peroxidase substrate as discussed in U.S. Pat. No. 7,951,547, which is incorporated by reference in its entirety. ADX5 was coated at a concentration of 6 ug/ml. ADX10-HRP was used at a concentration of 5 ug/ml. The results show that this *Toxocara* coproantigen ELISA yielded a positive signal with FEX from *T. canis* infected dog and *T. cati* infected cat. However, this *Toxocara* ELISA did not detect coproantigen in FEX from any of the following: Tapeworm *T. pisiformis* infected dog, *T taeniaeformis* infected cat, tapeworm *D. caninum* infected dog, tapeworm *D. caninum* infected cat, hookworm *A. caninum* infected dog, hookworm *A. tubaeforme* infected cat, whipworm *T. vulpis* infected dog, whipworm *T. felis* infected cat, *Giardia* infected dog, *Giardia* infected cat, and Parvovirus infected cat (FIG. 19, Row E). Therefore, this *Toxocara* ELISA specifically detected *Toxocara* coproantigen and did not crossreact with coproantigen from any of the following: Tapeworm *T. taeniaeformis*, tapeworm *T. pisiformis*, tapeworm *D. caninum*, hookworm *A. caninum*, hookworm *A. tubaeforme*, whipworm *T. vulpis*, whipworm *T. felis*, protozoon *Giardia lamblia*, and feline parvovirus. Thus, this *Toxocara* ELISA was highly specific and useful for the detection or diagnosis of infection or infestation with *T. canis* and *T. cati*. This roundworm *Toxocara* ELISA can be used to distinguish infection with roundworm *T. canis* or *T. cati* from infection with tapeworm *T. pisiformis*, tapeworm *T. taeniaeformis*, tapeworm *D. caninum*, hookworm *A. caninum*, hookworm *A. tubaeforme*, whipworm *T. vulpis*, whipworm *T. felis*, protozoon *Giardia lamblia*, canine parvovirus and feline parvovirus.

Whipworm *Trichuris* Coproantigen ELISA (FIG. 19, Row F).

A sandwich coproantigen ELISA assay for the detection of *T. vulpis* coproantigen was built. Briefly, a mouse mAb raised against *T. vulpis* protein DIV6901 (ADX6) was coated onto microtiter plates, incubated with fecal extract, then incubated with an HRP conjugate of another mouse mAb raised against *T. vulpis* protein DIV6901 (ADX14), followed by detection with a peroxidase substrate as discussed in U.S. Pat. No. 7,951,547, which is incorporated by reference in its entirety. ADX6 was coated at a concentration of 3 ug/ml. ADX10-HRP was used at a concentration of 3 ug/ml. The results show that this *Trichuris* coproantigen ELISA yielded a positive signal with FEX from *T. vulpis* infected dog and *T. felis* infected cat. However, this *Trichuris* ELISA did not detect coproantigen in FEX from any of the following: Tapeworm *T. pisiformis* infected dog, *T. taeniaeformis* infected cat, tapeworm *D. caninum* infected dog, tapeworm *D. caninum* infected cat, hookworm *A. caninum* infected dog, hookworm *A. tubaeforme* infected cat, roundworm *T. canis* infected dog, roundworm *T. cati* infected cat, *Giardia* infected dog, *Giardia* infected cat, and Parvovirus infected cat (FIG. 19, Row F). Therefore, this *Trichuris* ELISA specifically detected *T. vulpis* and *T. felis* coproantigen and did not crossreact with coproantigen from any of the following: Tapeworm *T. taeniaeformis*, tapeworm *T. pisiformis*, tapeworm *D. caninum*, hookworm *A. caninum*, hookworm *A. tubaeforme*, roundworm *T. canis*, roundworm *T. cati*, protozoon *Giardia lamblia*, and feline parvovirus. Thus, this *Trichuris* ELISA was highly specific and useful for the detection or diagnosis of infection or infestation with *T. vulpis* and *T. felis*. This whipworm *Trichuris* ELISA can be used to distinguish infection with whipworm *T. vulpis* or *T. felis* from infection with tapeworm *T. pisiformis*, tapeworm *T. taeniaeformis*, tapeworm *D. caninum*, hookworm *A. caninum*, hookworm *A. tubaeforme*, roundworm *T. canis*, roundworm *T. cati*, protozoon *Giardia lamblia*, canine parvovirus and feline parvovirus.

*Giardia* Coproantigen ELISA (FIG. 19, Row G).

A sandwich coproantigen ELISA assay for the detection of *Giardia lamblia* coproantigen was built with an antibody pair that specifically detects soluble antigen (SNAP® *Giardia* Test, IDEXX Laboratories, Inc. Westbrook, Me., USA) (Olson M E, Leonard N J, Strout J. Prevalence and diagnosis of *Giardia* infection in dogs and cats using a fecal antigen test and fecal smear. Can Vet J. 2010 June; 51(6):640-2. PMID: 20808578). Briefly, a rabbit anti-*Giardia* polyclonal antibody was coated onto microtiter plates, incubated with fecal extract, then incubated with an HRP conjugate of a mouse anti-*Giardia* monoclonal antibody, followed by detection with a peroxidase substrate. The polyclonal antibody was coated at a concentration of 3 ug/ml. The mAb-HRP was used at a concentration of 3 ug/ml. The results show that this *Giardia* coproantigen ELISA yielded a positive signal with FEX from *Giardia* infected dog and *Giardia* infected cat. However, this *Giardia* ELISA did not detect coproantigen in FEX from any of the following: Tapeworm *T pisiformis* infected dog, *T. taeniaeformis* infected cat, tapeworm *D. caninum* infected dog, tapeworm *D. caninum* infected cat, hookworm *A. caninum* infected dog, hookworm *A. tubaeforme* infected cat, roundworm *T. canis* infected dog, roundworm *T. cati* infected cat, whipworm *T. vulpis* infected dog, whipworm *T. felis* infected cat and Parvovirus infected cat (FIG. 19, Row G). Therefore, this *Giardia* ELISA specifically detected *Giardia lamblia* coproantigen and did not crossreact with coproantigen from any of the following: Tapeworm *T. taeniaeformis*, tapeworm *T. pisiformis*, tapeworm *D. caninum*, hookworm *A. caninum*, hookworm *A. tubaeforme*, roundworm *T. canis*, roundworm *T. cati*, whipworm *T. vulpis*, whipworm *T. vulpis* and feline parvovirus. Thus, this *Giardia* ELISA was highly species specific and useful for the detection or diagnosis of infection with *Giardia lamblia*. This *Giardia* ELISA can be used to distinguish infection with *Giardia lamblia* from infection with tapeworm *T. pisiformis*, tapeworm *T. taeniaeformis*, tapeworm *D. caninum*, hookworm *A. caninum*, hookworm

*A. tubaeforme*, roundworm *T. canis*, roundworm *T. cati*, whipworm *T. vulpis*, whipworm *T. felis*, canine parvovirus and feline parvovirus.

The positive infection status of the parvovirus infected cats (FIG. 19, columns 13 and 14) was confirmed with the SNAP® Parvo Test (M. Abd-Eldaim, M. Beall and M. A. Kennedy. "Detection of feline panleukopenia virus using a commercial ELISA for canine parvovirus" Vet Ther. 2009 Winter; 10(4): E1-6) according to the manufacturer's instructions (IDEXX Laboratories Inc., Westbrook, Me., USA). This multiplex fecal ELISA assay is capable of the simultaneous, specific detection of tapeworm *T. pisiformis*, tapeworm *T. taeniaeformis*, tapeworm *D. caninum*, hookworm *A. caninum*, hookworm *A. tubaeforme*, roundworm *T. canis*, roundworm *T. cati*, whipworm *T. vulpis*, whipworm *T. felis*, and protozoon *Giardia* lamblia.

This data demonstrates that the methods of the invention can be used to readily detect and distinguish between infections with least eight different intestinal parasites in a species specific-manner.

Example 5

A series of fecal ELISA assays capable of detecting two or three tapeworm species from the genus *Taenia*, for example *T. pisiformis, T. taeniaeformis*, and the genus *Dipylidium*, for example *D. caninum* were developed. The ELISAs were performed in microtiter plates essentially as described in section "EXAMPLE A" above.

Figure 20:
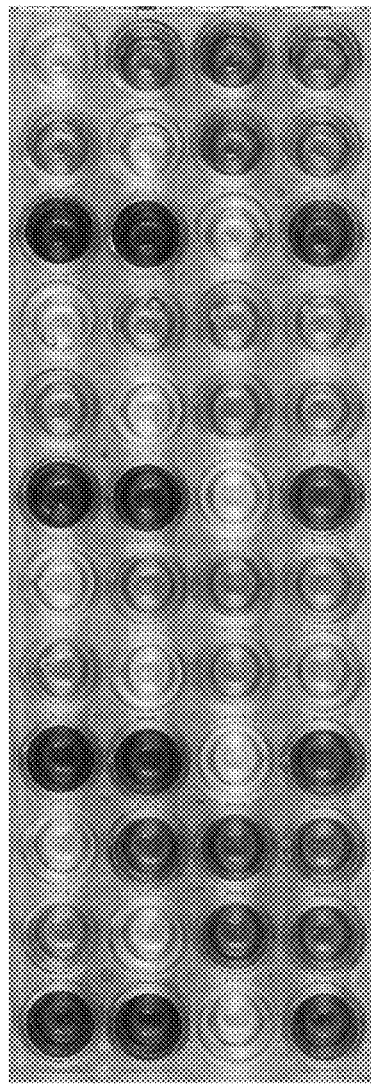
FIG. 20 shows a microtiter plate in which a series of ELISA assays capable of detecting two or three tapeworm species from the genus *Taenia*, for example *T. pisiformis*, *T. taeniaeformis*, and the genus *Dipylidium*, for example *D. caninum* were carried out using fecal extracts from a variety of infected canines and felines as discussed in Example 5. Fecal extracts from the following sources were tested in the ELISA assays: Four *T. pisiformis* positive dogs (FIG. 20, columns 1, 4, 7 and 10), four *T. taeniaeformis* infected cats (FIG. 20, column 2, 5, 8 and 11), two *D. caninum* infected dogs (FIG. 20, column 3 and 6), two *D. caninum* infected cats (FIG. 20, column 9 and 12).

Fecal extracts from the following sources were tested in the ELISA assays: Four *T. pisiformis* positive dogs (FIG. 20, columns 1, 4, 7 and 10), four *T. taeniaeformis* infected cats (FIG. 20, column 2, 5, 8 and 11), two *D. caninum* infected dogs (FIG. 20, column 3 and 6), two *D. caninum* infected cats (FIG. 20, column 9 and 12). In FIG. 20, columns 1 through 12 are an image of a single microtiter plate.

Coproantigen ELISA for the Detection of Tapeworms of the Genus *Taenia* (FIG. 20, Row A.

A sandwich ELISA assay for the detection of coproantigen from animals infected with *Taenia* tapeworms was built. Briefly, mAb ADX131 and mAb ADX184 were coated at a concentration of 3 ug/ml each onto microtiter plates, incubated with fecal extract, then incubated with mAb ADX132-HRP and ADX193-HRP conjugates at a concentration of 3 ug/ml each, followed by detection with a peroxidase substrate. The results show that this *Taenia* coproantigen ELISA yielded a positive signal with FEX from *T. pisiformis* infected dogs (FIG. 20, Row A, Columns 1, 4, 7 and 10) and *T. taeniaeformis* infected cats (FIG. 20, Row A, Columns 2, 5, 8 and 11). However, this *Taenia* ELISA did not detect coproantigen in FEX from tapeworm *D. caninum* infected dogs (FIG. 20, Row A, Columns 3 and 6) or *D. caninum* infected cats (FIG. 20, Row A, Columns 9 and 12). Therefore, this *Taenia* ELISA specifically detected *T. pisiformis* and *T. taeniaeformis* coproantigen and did not crossreact with coproantigen from *D. caninum*. This *Taenia* ELISA is useful for the detection or diagnosis of infection or infestation with one or more *Taenia* tapeworms, including *T. pisiformis* and *T. taeniaeformis*. This *Taenia* ELISA can be used to distinguish infection with one or more *Taenia* tapeworms, including *T. pisiformis* and *T. taeniaeformis*, from infection with *Dipylidium* tapeworm, including *D. caninum*.

Coproantigen ELISA for the Detection of Tapeworms *T. pisiformis* and *D. caninum* (FIG. 20, Row B).

A sandwich ELISA assay for the detection of coproantigen from animals infected with tapeworms *T. pisiformis* and *D. caninum* was built. Briefly, mAb ADX131 and mAb ADX226 were coated at a concentration of 3 ug/ml each onto microtiter plates, incubated with fecal extract, then incubated with mAb ADX132-HRP and mAb RDX5-HRP conjugates at a concentration of 3 ug/ml each, followed by detection with a peroxidase substrate. The results show that this ELISA yielded a positive signal with FEX from *T. pisiformis* infected dogs (FIG. 20, Row B, Columns 1, 4, 7 and 10), tapeworm *D. caninum* infected dogs (FIG. 20, Row B, Columns 3 and 6) and *D. caninum* infected cats (FIG. 20, Row B, Columns 9 and 12). However, this ELISA did not detect coproantigen in FEX from *T. taeniaeformis* infected cats (FIG. 20, Row B, Columns 2, 5, 8 and 11). Therefore, this ELISA specifically detected *T. pisiformis* and *D. caninum* coproantigen and did not crossreact with *T. taeniaeformis* coproantigen. This ELISA is useful for the detection or diagnosis of infection or infestation with tapeworms *T. pisiformis* and/or *D. caninum* and can be used to distinguish infection with tapeworms *T. pisiformis* and/or *D. caninum* from infection with tapeworm *T. taeniaeformis*.

Coproantigen ELISA for the Detection of Tapeworms *T. taeniaeformis* and *D. caninum* (FIG. 20, Row C).

A sandwich ELISA assay for the detection of coproantigen from animals infected with tapeworms *T. taeniaeformis* and *D. caninum* was built. Briefly, mAb ADX184 and mAb ADX226 were coated at a concentration of 3 ug/ml each onto microtiter plates, incubated with fecal extract, then incubated with mAb ADX193-HRP and RDX5-HRP conjugates at a concentration of 3 ug/ml each, followed by detection with a peroxidase substrate. The results show that this ELISA yielded a positive signal with FEX from *T. taeniaeformis* infected cats (FIG. 20, Row C, Columns 2, 5, 8 and 11), tapeworm *D. caninum* infected dogs (FIG. 20, Row C, Columns 3 and 6) and *D. caninum* infected cats (FIG. 20, Row C, Columns 9 and 12). However, this ELISA did not detect coproantigen in FEX from *T. pisiformis* infected dogs (FIG. 20, Row C, Columns 1, 4, 7 and 10). Therefore, this ELISA specifically detected *T. taeniaeformis* and *D. caninum* coproantigen and did not crossreact with *T. pisiformis* coproantigen. This ELISA is useful for the detection or diagnosis of infection or infestation with tapeworms *T. taeniaeformis* and/or *D. caninum* and can be used to distinguish infection with tapeworms *T. taeniaeformis* and/or *D. caninum* from infection with tapeworm *T. pisiformis*.

Coproantigen ELISA for the Detection of Tapeworms *T. pisiformis, T. taeniaeformis* and *D. caninum* (FIG. 20, Row D).

A sandwich ELISA assay for the detection of coproantigen from animals infected with tapeworms *T. pisiformis, T taeniaeformis* and *D. caninum* was built. Briefly, mAb ADX131, mAb ADX184 and mAb ADX226 were coated at a concentration of 3 ug/ml each onto microtiter plates, incubated with fecal extract, then incubated with mAb ADX132-HRP, mAb ADX193-HRP and RDX5-HRP conjugates at a concentration of 3 ug/ml each, followed by detection with a peroxidase substrate. The results show that this ELISA yielded a positive signal with FEX from *T. pisiformis* infected dogs (FIG. 20, Row D, Columns 1, 4, 7 and 10), *T. taeniaeformis* infected cats (FIG. 20, Row D, Columns 2, 5, 8 and 11), tapeworm *D. caninum* infected dogs (FIG. 20, Row D, Columns 3 and 6) and *D. caninum* infected cats (FIG. 20, Row D, Columns 9 and 12). Therefore, this ELISA detected *T. pisiformis, T. taeniaeformis* and *D. caninum* coproantigen. This ELISA is useful for the detection or diagnosis of infection or infestation with tapeworms *T. pisiformis, T. taeniaeformis* and/or *D. caninum*.

These data demonstrate this ELISA assay can be used to readily detect infection with *Taenia* and/or *Dipylidium* tapeworms in dogs and cats.

We claim:

1. A method of diagnosing and treating a mammal infected with of one or more platyhelminthic antigens in a fecal sample, the method comprising:
   (a) contacting a fecal sample from a mammal with one or more antibodies selected from the group consisting of:
      (i) a first antibody capable of specifically binding a coproantigen from a first tapeworm *Taenia pisiformis*, but not a coproantigen from a second tapeworm *Taenia taeniaeformis* or a coproantigen from a third tapeworm *Dipylidium caninum*;
      (ii) a second antibody capable of specifically binding the coproantigen from the second tapeworm, but not the coproantigen from the first tapeworm or the coproantigen from the third tapeworm; and
      (iii) a third antibody capable of specifically binding the coproantigen from the third tapeworm, but not the coproantigen from the first tapeworm or the coproantigen from the second tapeworm; and
   (b) detecting the presence or absence of the antibody-coproantigen complexes, if any;
   (c) diagnosing the mammal as having:
      (i) a first tapeworm infection if a first tapeworm antibody-coproantigen complex is present;
      (ii) a second tapeworm infection if a second tapeworm antibody-coproantigen complex is present; and
      (iii) a third tapeworm infection if a third tapeworm antibody-coproantigen complex is present; and
   (d) administering an effective amount of one or more therapeutic agents to treat the mammal having the first tapeworm infection, the second tapeworm infection, or third tapeworm infection or combination thereof.

2. The method of claim 1, wherein step (d) further includes one or more additional therapeutic agents to: (a) treat infection by one or more helminthic worm parasites, one or more non-worm parasites, one or more viruses, one or more fungi, one or more protozoa, or one or more bacteria.

3. The method of claim 2, wherein step (d) further includes one or more therapeutic agents to: (b) control, repel or kill an intermediate host of a platyhelminthic worm parasite, helminthic worm parasite, non-worm parasite, virus, fungus, protozoa, or bacterium.

4. The method of claim 1, wherein the fecal sample is obtained from a mammal that is a canine or a feline.

5. The method of claim 1, wherein the first antibody does not specifically cross-react with one or more coproantigens selected from the group consisting of: hookworm, roundworm, whipworm, *Giardia* and parvovirus.

6. The method of claim 5, wherein the hookworm is *Ancylostoma* the roundworm is *Toxocara*, and the whipworm is *Trichuris*.

7. The method of claim 6, wherein the hookworm is *Ancylostoma caninum* or *Ancylostoma tubaeforme*; the roundworm is *Toxocara canis* or *Toxocara cati*; the whipworm is *Trichuris vulpis* or *Trichuris felis*; the *Giardia* is *Giardia lamblia*; and the parvovirus is feline parvovirus or canine parvovirus.

8. The method of claim 1, wherein the second antibody does not specifically cross-react with one or more coproantigens selected from the group consisting of: hookworm coproantigen, roundworm coproantigen, coproantigen, *Giardia* coproantigen and parvovirus coproantigen.

9. The method of claim 8, wherein the hookworm is *Ancylostoma*, the roundworm is *Toxocara*, and the whipworm is *Trichuris*.

10. The method of claim 9, wherein the hookworm is *Ancylostoma caninum* or *Ancylostoma tubaeforme*; the roundworm is *Toxocara canis* or *Toxocara cati*; the whipworm is *Trichuris vulpis* or *Trichuris felis*; the *Giardia* is *Giardia lamblia*; and the parvovirus is feline parvovirus or canine parvovirus.

11. The method of claim 1, wherein the third antibody does not specifically cross-react with one or more coproantigens selected from the group consisting of: hookworm coproantigen, roundworm coproantigen, whipworm coproantigen, *Giardia* coproantigen and parvovirus coproantigen.

12. The method of claim 11, wherein the hookworm is *Ancylostoma*, the roundworm is *Toxocara*, and the whipworm is *Trichuris*.

13. The method of claim 12, wherein the hookworm is *Ancylostoma caninum* or *Ancylostoma tubaeforme*; the roundworm is *Toxocara canis* or *Toxocara cati*; the whipworm is *Trichuris vulpis* or *Trichuris felis*; the *Giardia* is *Giardia lamblia*; and the parvovirus is feline parvovirus or canine parvovirus.

14. The method of claim 1, wherein the first antibody, the second antibody and third antibody do not specifically bind any coproantigen derived from at least one worm selected from the group consisting of: roundworm, whipworm, and hookworm.

15. The method of claim 14, wherein the roundworm is *Toxocara canis*, *Toxocara cati*, *Toxocara vitulorum*, *Toxascaris leonina*, *Baylisascaris procyonis*, *Ascaridia Parascaris equorum*, *Ascaris suum*, *Ascaris lumbricoides*, *Anisakis simplex*, or *Pseudoterranova decipiens*.

16. The method of claim 14, wherein the whipworm is *Trichuris vulpis*, *Trichuris campanula*, *Trichuris serrata*, *Trichuris felis*, *Trichuris suis*, *Trichuris trichiura*, *Trichuris discolor* or *Trichocephalus trichiuris*.

17. The method of claim 14, wherein the hookworm is *Ancylostoma caninum*, *Ancylostoma braziliense*, *Ancylostoma duodenal*, *Ancylostoma ceylanicum*, *Ancylostoma tubaeforme*, *Ancylostoma pluridentatum*, *Necator americanus*, or *Uncinaria stenocephala*.

18. The method according to claim 1, wherein step (a) group further consists of:
   (i) an antibody capable of specifically binding a roundworm coproantigen, but does not specifically cross-react with one or more coproantigens selected from the group consisting of whipworm, hookworm, tapeworm, *Giardia* and parvovirus;
   (ii) an antibody capable of specifically binding a whipworm coproantigen, but does not specifically cross-react with one or more coproantigens selected from the group consisting of roundworm, hookworm, tapeworm, *Giardia* and parvovirus; and
   (iii) an antibody capable of specifically binding a hookworm coproantigen, but does not specifically cross-react with one or more coproantigens selected from the group consisting of whipworm, roundworm, tapeworm, *Giardia* and parvovirus;
   (iv) an antibody capable of specifically binding *Giardia* coproantigen, but does not specifically cross-react with one or more coproantigens selected from the group consisting of roundworm coproantigen, whipworm coproantigen, hookworm coproantigen, tapeworm *Taenia* coproantigen, tapeworm *Dipylidium* coproantigen and parvovirus coproantigen; and (v) an antibody capable of specifically binding parvovirus coproantigen, but does not specifically cross-react with one or more coproantigens selected from the group consisting of roundworm coproantigen, whipworm coproantigen, hookworm coproantigen, tapeworm *Taenia* coproantigen, tapeworm *Dipylidium* coproantigen and *Giardia* coproantigen.

19. The method of claim 18, wherein the hookworm is *Anyclostoma*, the roundworm is *Toxocara* and the whipworm is *Trichuris*.

20. The method of claim 19, wherein the hookworm is *Ancylostoma caninum* or *Ancylostoma tubaeforme*; the roundworm is *Toxocara canis* or *Toxocara cati*; the whipworm is *Trichuris vulpis* or *Trichuris felis*; the *Giardia* is *Giardia lamblia*; and the parvovirus is feline parvovirus or canine parvovirus.

21. The method of claim 18, wherein step (c) diagnosing further comprises:
   (iv) a roundworm infection if a roundworm antibody-coproantigen complex is present;
   (v) a whipworm infection if a whipworm antibody-coproantigen complex is present;
   (vi) a hookworm infection if a hookworm antibody-coproantigen complex is present;
   (vii) a *Giardia* infection if a *Giardia* antibody-coproantigen complex is present; and
   (viii) a parvovirus infection if a parvovirus antibody-coproantigen complex is present.

22. The method of claim 1, wherein the fecal sample is contacted with at two or more antibodies.

23. The method of claim 1, wherein the step (b) of detecting the presence or absence of the complexes further includes a step of providing at least one secondary antibody that binds to the one or more complexes.

24. The method of claim 23, wherein the secondary antibody is labeled or attached to a solid support.

25. The method of claim 1, wherein one or more of the first, second and third antibodies are labeled.

26. The method of claim 1, wherein the first, second and third antibodies are immobilized on a solid support.

27. The method of claim 21, wherein one or more of the antibody capable of specifically binding a roundworm coproantigen, the antibody capable of specifically binding a whipworm coproantigen, the antibody capable of specifically binding a hookworm coproantigen, the antibody capable of specifically binding *Giardia* coproantigen, and the antibody capable of specifically binding parvovirus coproantigen are labeled.

28. The method of claim 21, wherein the antibody capable of specifically binding a roundworm coproantigen, the antibody capable of specifically binding a whipworm coproantigen, the antibody capable of specifically binding a hookworm coproantigen, the antibody capable of specifically binding *Giardia* coproantigen, and the antibody capable of specifically binding parvovirus coproantigen are immobilized on a solid support.

29. The method of claim 26, wherein the solid support forms part of an enzyme-linked immunosorbent assay device.

30. The method of claim 29, further comprising a step of contacting the sample with one or more reagents to detect one or more of the group consisting of: one or more helminthic worm parasites, one or more non-worm parasites, one or more viruses, one or more fungi, one or more protozoa, and one or more bacteria.

31. The method of claim 29, wherein the enzyme-linked immunosorbent assay device is a lateral flow immunoassay device.

32. The method of claim 30, wherein the reagents comprise one or more antibodies or one or more antigens recognized by antibodies specific for one or more helminthic worm parasites, non-worm parasites, one or more viruses, one or more fungi, one or more protozoa, or one or more bacteria.

33. The method of claim 31, wherein the one or more helminthic worm parasites comprise at least one of roundworm, whipworm, hookworm and heartworm.

34. The method of claim 32, wherein the one or more reagents is an antibody that specifically binds to a non-worm parasite *Giardia* coproantigen.

35. The method of claim 34, wherein the *Giardia* is *Giardia lamblia*.

36. The method of claim 35, wherein the antibody does not bind to coproantigen derived from *T. pisiformi*, *T taeniaeformis*, *D. caninum*, *A. caninum* infected dog, *A. tubaeforme*, *T. canis*, *T. cati*, *T. vulpis*, *T. felis* and Parvovirus.

37. The method of claim 1, further comprising a step of determining the presence or absence of a nucleic acid from a roundworm, whipworm, or hookworm.

38. The method of claim 37, wherein the step of determining presence or absence of the nucleic acid is carried out by using a polymerase chain reaction (PCR)-based assay.

39. The method of claim 1, wherein at least one of the coproantigens is glycosylated.

40. The method of claim 39, wherein step (b) of detecting the presence or absence of the complexes further includes the step of providing one or more lectins that binds to at least one of the complexes.

41. The method of claim 40, wherein the lectin is delectably labeled or immobilized onto a solid support.

* * * * *